United States Patent
McDonald et al.

(10) Patent No.: US 8,426,587 B2
(45) Date of Patent: Apr. 23, 2013

(54) HALOALLYLAMINE INHIBITORS OF SSAO/VAP-1 AND USES THEREFOR

(75) Inventors: Ian A. McDonald, Killarney Heights (AU); Craig Ivan Turner, Stanmore (AU); Mandar Deodhar, Ashfield (AU); Jonathan Stuart Foot, Glasgow (GB)

(73) Assignee: Pharmaxis Ltd. (AU)

( * ) Notice: Subject to any disclaimer, the term of this patent is extended or adjusted under 35 U.S.C. 154(b) by 161 days.

(21) Appl. No.: 12/742,915

(22) PCT Filed: Nov. 19, 2008

(86) PCT No.: PCT/IB2008/003124
§ 371 (c)(1),
(2), (4) Date: Aug. 13, 2010

(87) PCT Pub. No.: WO2009/066152
PCT Pub. Date: May 28, 2009

(65) Prior Publication Data
US 2010/0298330 A1    Nov. 25, 2010

Related U.S. Application Data

(60) Provisional application No. 60/989,634, filed on Nov. 21, 2007.

(51) Int. Cl.
C07D 295/092  (2006.01)
C07D 211/00  (2006.01)
C07D 207/00  (2006.01)
C07D 277/28  (2006.01)
C07D 233/00  (2006.01)
C07D 263/02  (2006.01)
C07D 213/56  (2006.01)
C07C 211/00  (2006.01)
A61K 31/41  (2006.01)
A61K 31/403  (2006.01)
A61K 31/365  (2006.01)
A61K 31/435  (2006.01)
A61K 31/381  (2006.01)

(52) U.S. Cl.
USPC ........... 544/162; 546/184; 548/400; 548/203; 548/348.1; 548/215; 564/336; 514/237.8; 514/227; 514/438

(58) Field of Classification Search ........................ None
See application file for complete search history.

(56) References Cited

U.S. PATENT DOCUMENTS

| | | |
|---|---|---|
| 3,710,795 A | 1/1973 | Higuchi et al. |
| RE28,819 E | 5/1976 | Thompson |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,454,158 A | 6/1984 | Bey |
| 4,522,811 A | 6/1985 | Eppstein et al. |
| 4,650,907 A | 3/1987 | Bey et al. |
| 5,709,874 A | 1/1998 | Hanson et al. |
| 5,759,542 A | 6/1998 | Gurewich |
| 5,840,674 A | 11/1998 | Yatvin et al. |
| 5,860,957 A | 1/1999 | Jacobsen et al. |
| 5,900,252 A | 5/1999 | Calanchi et al. |
| 5,948,433 A | 9/1999 | Burton et al. |
| 5,972,366 A | 10/1999 | Haynes et al. |
| 5,983,134 A | 11/1999 | Ostrow |
| 5,984,433 A | 11/1999 | Stumpe et al. |
| 5,985,307 A | 11/1999 | Hanson et al. |
| 5,985,317 A | 11/1999 | Venkateshwaran et al. |
| 6,004,534 A | 12/1999 | Langer et al. |
| 6,010,715 A | 1/2000 | Wick et al. |
| 6,024,975 A | 2/2000 | D'Angelo et al. |
| 6,039,975 A | 3/2000 | Shah et al. |
| 6,048,736 A | 4/2000 | Kosak |

(Continued)

FOREIGN PATENT DOCUMENTS

| | | |
|---|---|---|
| NZ | 228068 | 11/1991 |
| WO | WO-93/17707 | 9/1993 |
| WO | WO-2004/016997 | 3/2004 |
| WO | WO-2006/094201 | 9/2006 |
| WO | WO-2007/005737 | 1/2007 |
| WO | WO-2007/120526 | 10/2007 |
| WO | WO-2007/126457 | 11/2007 |

OTHER PUBLICATIONS

Aktas et al., Neuronal damage in brain inflammation, Arch Neurol 2007, 64(2):185-189.

(Continued)

*Primary Examiner* — Jason M Nolan
*Assistant Examiner* — Ana Z Muresan
(74) *Attorney, Agent, or Firm* — Kilpatrick Townsend & Stockton LLP

(57) ABSTRACT

The present invention is related to the preparation and pharmaceutical use of novel haloallylamine derivatives as SSAO/VAP-1 inhibitors having the structure of Formula I, as defined in the specification: (I). The invention also relates to methods of using invention compounds, or pharmaceutically acceptable salt or derivatives thereof, for the treatment of a variety of indications, e.g., inflammatory diseases.

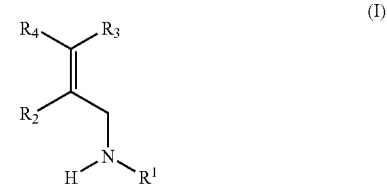

(I)

11 Claims, No Drawings

U.S. PATENT DOCUMENTS

| | | | |
|---|---|---|---|
| 6,060,082 | A | 5/2000 | Chen et al. |
| 6,071,495 | A | 6/2000 | Unger et al. |
| 6,120,751 | A | 9/2000 | Unger |
| 6,131,570 | A | 10/2000 | Schuster et al. |
| 6,139,865 | A | 10/2000 | Friend et al. |
| 6,167,301 | A | 12/2000 | Flower et al. |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,267,983 | B1 | 7/2001 | Fujii et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,624,202 | B2 | 9/2003 | Smith et al. |
| 2006/0025438 | A1 | 2/2006 | Salter-Cid et al. |
| 2006/0229346 | A1 | 10/2006 | Ueno et al. |
| 2007/0078157 | A1 | 4/2007 | Salter-Cid et al. |
| 2007/0093646 | A1 | 4/2007 | Salminen et al. |

OTHER PUBLICATIONS

Bodkin et al., Transdermal Selegiline in Major Depression: A Double-Blind, Placebo-Controlled, Parallel-Group Study in Outpatients, Am J. Psychiatry, 159(11):1869-1875 (2002).

Chebib et al., Analogues of gamma-aminobutyric acid (GABA) and trans-4-aminocrotonic acid (TACA) substituted in the 2 position as GABAC receptor antagonists, Br J Pharmacol., 1997, 122(8):1551-1560.

Elliott et al, In-vivo effects of (E)-2-(3'-,4'-dimethoxyphenyl)-3-fluorallylamine (MDL 72145) on amine oxidase activities in the rat. Selective inhibition of semicarbazide-sensitive amine oxidase in vascular and brown adipose tissues, J Pharm Pharmacol, 1989, 41(1):37-41.

International Preliminary Report on Patentability dated Jun. 3, 2010 for PCT Application No. PCT/IB2008/003124.

International Search Report and the Written Opinion dated Mar. 26, 2009 for PCT Application No. PCT/IB2008/003124.

Jalkanen et al., The oxidase activity of vascular adhesion protein-1 (VAP-1) induces endothelial E- and P-selectins and leukocyte binding, Blood, 110:1564-1870 (2007).

Jeon et al, Highly potent propargylamine and allylamine inhibitors of bovine plasma amine oxidase, Biochem Biophys Res Commun, 2003, 304(4):788-794.

Kamal et al., Synthesis of C-8 Alkylamino, Substituted Pyrrolo[2,1-c][1,4]-benzodiazepines as Potential Anti-Cancer Agents, Bioorganic and Medicinal Chemistry Letters 2002, 12(15):1917-1919.

Kim et al., Inactivation of bovine plasma amine oxidase by haloallylamines. Bioorg med Chem., 2006, 14(5):1444-1453.

Lalor et al., Vascular adhesion protein-1 as a potential therapeutic target in liver disease, Ann NY Acad Sci, 1110:485-496 (2007).

Lee et al., 3-pyrrolines are mechanism-based inactivators of the quinone-dependent amine oxidases but only substrates of the flavin-dependent amine oxidases, J Am Chem Soc., 2002, 124(41):12135-12143.

Lyles et al, Aminoacetone metabolism by semicarbazide-sensitive amine oxidase in rat aorta, Biochem Pharmacol, 1995, 49(3):416-419.

Lyles et al, Inhibition of rat aorta semicarbazide-sensitive amine oxidase by 2-phenyl-3-haioallylamines and related compounds, Abstract, 1987, 36(17):2847-2853.

Lyles et al, Mammalian plasma and tissue-bound semicarbazide-sensitive amine oxidases: biochemical, pharmacological and toxicological aspects, 1996, Int J Biochem Cell Biol, 1996, 28(3):259-274.

McDonald et al, Enzyme-activated irreversible inhibitors of monoamine oxidase: phenylallylamine structure-activity relationships, J Med Chem, 28:186-193.

McDonald et al., Chapter 15: Semicarbazide Sensitive Amine Oxidase and Vascular Adhesion Protein-1: One Protein Being Validated as a Therapeutic Target for Inflammatory Diseases, Annual Reports in Medicinal Chemistry, 2008, 42:229-243.

Mitsunobu, O., The use of diethyl azodicarboxylate and triphenylphosphine in synthesis and transformation of natural products, Synthesis, 1981, 1-28.

Noda et al., A Vascular adhesion protein-1 blockade suppresses choroidal neovascularization, Faseb J 2008, 22:2928-2935.

Noda et al., Inhibition of vascular adhesion protein-1 suppresses endotoxin-induced uveitis, Faseb J (2008), 22:1094-1103.

O'Connell et al., Differential inhibition of six copper amine oxidases by a family of 4-(aryloxy)-2-butynamines: Evidence for a new mode of inactivation. Biochemistry, 2004, 43(34):10965-10978.

Saimi et al., VAP-1: an adhesin and an enzyme, Trends Immunol, 2001. 22:211-216.

Shepard et al, Towards the development of selective amine oxidase inhibitors, Mechanism-based inhibition of six copper containing amine oxidases, Eur J Biochem, 2002, 269(15):3645-3658.

Silverman et al., Inactivation of gamma-aminobutyric acid aminotransferase by (Z)-4-amino-2-fluorobut-2-enoic acid, Biochemistry, 1986, 27(9):3285-3289.

Smith et al., Targeting Vascular Adhesion Protein-1 to Treat Autoimmune and Inflammatory Diseases, Ann. N.Y. Acad. Sci., 2007, 1110:382-388.

Vashkevich et al., Synthesis of surfactants derived from adamantane, Russian J Applied Chem., 2001, 74:1892-1898.

Vidrio et al, 2-bromoethylamine, a suicide inhibitor of semicarbazide-sensitive amine oxidase, increases hydralazine hypotension in rats, J Cardiovasc Pharmacol, 2005, 46(3)316-324.

World Wide Web at en.wikipedia.org/wiki/Mitsunobu_reaction.

Xu et al., Vascular Adhesien Protein-1 Plays an Important Role in Postischemic Inflammation and Neuropathology in Diabetic, Estrogen-Treated Ovariectomized Female Rats Subjected to Transiet Forebrain Ischemia, J Pharmacol Exp Ther., 2006, 317(1):19-29.

Youdim et al., Multi-functional drugs for various CNS targets in the treatment of neurodegenerative disorders, Trends Pharmacol Sci,, 2005, 26(1):27-35.

Yu et al., Inhibition of a type B monoamine oxidase inhibitor, (E)-2-(4-fluorophenethyl)-3-fluoroallylamine (MDL-72974A), on semicarbazide-sensitive amine oxidases isolated from vascular tissues and sera of different species, Biochem Pharmacol, 1992, 43(2):307-312.

Yu et al., Involvement of Semicarbazide-Sensitive Amine Oxidase-Mediated Deamination in Lipopolysaccharide-Induced Pulmonary Inflammation, Am J Pathol 2006, 168:718-726.

Zhang et al., Highly potent 3-pyrroline mechanism-based inhibitors of bovine plasma amine oxidase and mass spectrometric confirmation of cofactor derivatization, Bioorg Med Chem., 2007, 10(4):1868-1877.

Extended European Search Report dated Jan. 13, 2011 in application EP 08851514.

HALOALLYLAMINE INHIBITORS OF SSAO/VAP-1 AND USES THEREFOR

FIELD OF THE INVENTION

The present invention relates to novel compounds which are capable of inhibiting certain amine oxidase enzymes. Invention compounds are useful for treatment of a variety of indications, e.g., the symptoms of inflammation in human subjects as well as in pets and livestock, the treatment of psychological diseases, neurodegenerative disorders, and the like. In addition, the present invention relates to pharmaceutical compositions containing these compounds, as well as various uses therefor.

BACKGROUND OF THE INVENTION

Semicarbazide-sensitive amine oxidase (SSAO), also known as plasma amine oxidase and benzylamine oxidase, is identical in structure to vascular adhesion protein-1 (VAP-1). In the following discussion, SSAO/VAP-1 is used to describe this protein. The role of this protein in inflammatory diseases has been reviewed (see, for example, Smith D. J. and Vaino P. J., Targeting Vascular Adhesion Protein-1 to Treat Autoimmune and Inflammatory Diseases. *Ann. N.Y. Acad. Sci.* 2007, Vol 1110, pages 382-388; and McDonald I. A. et al., Semicarbazide Sensitive Amine Oxidase and Vascular Adhesion Protein-1: One Protein Being Validated as a Therapeutic Target for Inflammatory Diseases. *Annual Reports in Medicinal Chemistry*, 2008, Vol 43).

In most organisms, including humans, two families of mammalian amine oxidases metabolize various mono-, di-, and polyamines produced endogenously or absorbed from exogenous sources. These include the monoamine oxidases (MAO-A and MAO-B) which are present in the mitochondria of most cell types and use covalently bound flavin adenine dinucleotide (FAD) as the cofactor. Polyamine oxidase is another FAD-dependent amine oxidase which oxidatively deaminates spermine and spermidine. SSAO/VAP-1 belongs to the second family which is dependent on copper and uses other co-factors apart from FAD, such as an oxidized tyrosine residue (abbreviated as TPQ). MAO and SSAO/VAP-1 oxidatively deaminate some common substrates which includes the monoamines such dopamine, tyramine and benzylamine.

Some of these enzymes were originally defined by the ability of certain compounds to inhibit the enzymatic activity thereof For example MAO-A is selectively inhibited by clorgyline, MAO-B by L-deprenyl, while neither clorgyline nor L-deprenyl can inhibit the amine oxidase activity of SSAO/VAP-1. SSAO/VAP-1 can be inhibited by semicarbazide, hence the name semicarbazide sensitive amine oxidase.

SSAO/VAP-1 is an ectoenzyme containing a very short cytoplasmic tail, a single transmembrane domain, and a large, highly glycosylated extracellular domain which contains the active center for the amine oxidase activity. SSAO/VAP-1 is also present in a soluble form circulating in the plasma of some animals. It has been shown that this form is a cleaved product of membrane-bound SSAO/VAP-1. It is currently unclear if there are distinct functions for the membrane and soluble form of SSAO/VAP-1.

SSAO/VAP-1 appears to have two physiological functions: the first is the amine oxidase activity mentioned above and the second is cell adhesion activity. Both activities are associated with inflammatory processes. SSAO/VAP-1 was shown to play an important role in extravasation of inflammatory cells from the circulation to sites of inflammation (Salmi M. and Jalkanen S., VAP-1: an adhesin and an enzyme. Trends Immunol 2001, 22, 211-216). VAP-1 antibodies have been demonstrated to attenuate inflammatory processes by blocking the adhesion site of the SSAO/VAP-1 protein, and, together with a substantial body of evidence of in vitro and in vivo knockouts, it is now clear that SSAO/VAP-1 is an important cellular mediator of inflammation. Transgenic mice lacking SSAO/VAP-1 show reduced adhesion of leukocytes to endothelial cells, reduced lymphocyte homing to the lymph nodes and a concomitant attenuated inflammatory response in a peritonitis model. These animals were otherwise healthy, grew normally, were fertile, and examination of various organs and tissues showed the normal phenotype. Furthermore, inhibitors of the amine oxidase activity of SSAO/VAP-1 have been found to interfere with leukocyte rolling, adhesion and extravasation and, similar to SSAO/VAP-1 antibodies, exhibit anti-inflammatory properties.

Inflammation is the first response of the immune system to infection or irritation. The migration of leukocytes from the circulation into tissues is essential for this process. Inappropriate inflammatory responses can result in local inflammation of otherwise healthy tissue which can lead to disorders such as rheumatoid arthritis, inflammatory bowel disease, multiple sclerosis and respiratory diseases. Leukocytes first adhere to the endothelium via binding to adhesion molecules before they can start the process of passing through the walls of the blood vessels. Membrane bound SSAO/VAP-1 is abundantly expressed in vascular endothelial cells such as high venule endothelial cells (HVE) of lymphatic organs and is also expressed in hepatic sinusoidal endothelial cells (HSEC), smooth muscle cells and adipocytes. The expression of SSAO/VAP-1 on the cell surface of endothelial cells is tightly regulated and is increased during inflammation. In the presence of an SSAO/VAP-1 substrate (benzylamine), NFκB was activated in HSECs together with up regulation of other adhesion molecules, E-selectin and chemokine CXCL8 (IL-8) in vitro. A recent study confirms this result by showing by mutagenesis that the transcription and translation of E-selectin and P-selectin is induced by the enzyme activity of SSAO/VAP-1. These results suggest an important role of the amine oxidase activity of SSAO/VAP-1 in the inflammatory response. It has been reported that the oxidase activity of SSAO/VAP-1 induces endothelial E- and P-selectins and leukocyte binding (Jalkanen S, et al., The oxidase activity of vascular adhesion protein-1 (VAP-1) induces endothelial E- and P-selectins and leukocyte binding. Blood 2007, 110, 1864-1870).

Excessive and chronic inflammatory responses have been associated with the symptoms of many chronic diseases, such as rheumatoid arthritis, multiple sclerosis, asthma, bronchitis and chronic obstructive pulmonary disease (COPD). Patients suffering from either atopic eczema or psoriasis (both chronic inflammatory skin disorders) have higher levels of SSAO/VAP-1 positive cells in their skin compared to skin from healthy controls.

SSAO/VAP-1 is also highly expressed in adipocytes where it plays a role in glucose transport independent of the presence of insulin. It has been observed that levels of plasma SSAO/VAP-1 are increased in patients suffering from diabetes. Elevated levels of plasma SSAO/VAP-1 have been found in patients suffering from other illnesses, such as congestive heart failure and liver cirrhosis. It is believed that SSAO/VAP-1 is associated with most, if not all, inflammatory diseases whether the inflammation is in response to an immune response or subsequent to other events such as occlusion and reperfusion of blood vessels.

It has been reported that inhibition of vascular adhesion protein-1 (VAP-1) suppresses endotoxin-induced uveitis (EIU). In the retina, SSAO/VAP-1 is exclusively expressed in the vasculature, and its expression level was found to be elevated during EIU. SSAO/VAP-1 inhibition in animal models of EIU significantly suppressed leukocyte recruitment to the anterior chamber, vitreous, and retina. The data suggest an important role for SSAO/VAP-1 in the recruitment of leukocytes to the immune-privileged ocular tissues during acute inflammation (see, for example, Noda K. et al., Inhibition of vascular adhesion protein-1 suppresses endotoxin-induced uveitis. *Faseb J* 22, 1094-1103 (2008)) and Noda K. et al., A Vascular adhesion protein-1 blockade suppresses choroidal neovascularization. *Faseb J* (2008)).

In a mouse overexpressing human SSAO/VAP-1, the SSAO inhibitor Mofegiline significantly attentuates the LPS-induced increase in TNF-a. This inhibitor also significantly reduces BAL cell counts. These results demonstrate that SSAO/VAP-1 is involved in LPS-induced pulmonary inflammation (see, for example, P. Yu et al American Journal of Pathology, 168, 718-726 (2006)). Acute lung injury (ALI) and acute respiratory distress syndrome (ARDS) are serious inflammatory disorders of the lung. These disorders are thought to develop when pulmonary or systemic inflammation leads to systemic release of cytokines and other proinflammatory molecules, which recruit neutrophils to the lungs, which in turn release leukotrienes, oxidants, platelet-activating factor, and proteases (see, for example, the Merck Manuals Online Medical Library on the World Wide Web at merck.com/mmpe/sec06/ch066/ch066a.html).

SSAO/VAP-1 is upregulated in the liver and serum of patients with inflammatory liver disease; inhibition of SSAO/VAP-1 activity decreases migration of normal lymphocytes across hepatic sinusoidal endothelial cells and has significant effects on the migration of peripheral blood lymphocytes. It has been suggested that the restricted expression of SSAO/VAP-1 and increased production of secreted SSAO/VAP-1 in inflammatory liver disease indicates utility of this protein as a therapeutic target for diseases associated with liver inflammation (see, for example, P. Lalor et al., Ann. N.Y. Acad. Sci. 1110: 485-496 (2007)).

During the SSAO/VAP-1 amine oxidase catalytic cycle, the covalently bound cofactor, TPQ, is first reduced, and then re-oxidized by oxygen in the presence of copper with the generation of hydrogen peroxide as a by-product. It has been speculated that excessive amounts of hydrogen peroxide concentrations can be deleterious and may contribute to the pathology of various inflammatory and neurodegenerative processes (Götz M. E., et al., Oxidative stress: free radical production in neural degeneration. *Pharmacol Ther* 1994; 63: 37-122).

Monoamine oxidase inhibitors have been used as therapeutic agents for many years (see Tipton, K. F. et al., *Monoamine Oxidase and Disease*, Academic Press, 1984). Monoamine oxidase-B (MAO-B) is an enzyme present on outer mitochondrial membranes. In man MAO-B oxidatively deaminates dopamine, N-methylhistamine and some trace amines. Monoamine oxidase inhibitors have been known for many years and some are clinically prescribed medications for the treatment of Parkinson's disease and more recently for the treatment of CNS disorders such as bipolar depression and attention deficit hyperactivity disorder (ADHD), where dopamine is likely to play an important role in the pathophysiology. The most well known MAO-B inhibitor is Selegiline (L-deprenyl, Eldepryl® or Anipryl® for veterinary use) which is used to treat Parkinson's disease and senile dementia. A transdermal patch formulation of Selegiline (Emsam Patch) has been shown to be effective treatment for major depression (Bodkin, J. A. and Amsterdam, J. D., Transdermal Selegiline in Major Depression: A Double-Blind, Placebo-Controlled, Parallel-Group Study in Outpatients. *Am J Psychiatry* 2002; 159:1869-1875), and is currently being evaluated in ADHD patients. The drug is also being evaluated to help people stop smoking tobacco and marijuana.

Inflammation is believed to be an important feature of neurodegenerative diseases such as Parkinson's disease, Alzheimer's disease and multiple sclerosis, and similarly is a feature of the pathophysiology that occurs after a cerebral occlusion/reperfusion event (Aktas, O. et al., Neuronal damage in brain inflammation. *Arch Neurol* 2007, 64:185-9). Excessive activity of MAO-B and SSAO/VAP-1 has been independently implicated in these processes (Xu, H-L. et al., Vascular Adhesion Protein-1 plays an important role in postischemic inflammation and neuropathology in diabetic, estrogen-treated ovariectomized female rats subjected to transient forebrain ischemia. *Journal Pharmacology and Experimental Therapeutics*, 2006, 317: 19-26 and Youdim, M. B., Buccafusco, J. J., Multi-functional drugs for various CNS targets in the treatment of neurodegenerative disorders. *Trends Pharmacol Sci*, 2005 26:27-35).

Some known MAO inhibitors also inhibit SSAO/VAP-1 (e.g., the MAO-B inhibitor Mofegiline illustrated below). Mofegiline has been reported to inhibit experimental autoimmune encephalomyelitis (US 2006/0025438A1). This inhibitor is a member of the haloallylamine family of MAO inhibitors; the halogen in Mofegiline is fluorine. Fluorallylamine inhibitors are described in Bey P., U.S. Pat. No. 4,454,158 (Allyl amine MAO inhibitors). There have been reports of a chloroallylamine, MDL72274 (illustrated below), selectively inhibiting rat SSAO/VAP-1 compared to MAO-A and MAO-B.

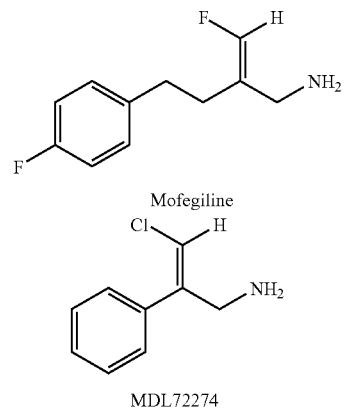

Other examples structurally related to Mofegiline can be found in LJPC WO 2007/120528 A2.

References to the following examples of SSAO/VAP-1 inhibitors, and to the effects of such inhibitors in various animal models of disease, can be found in the review publication by McDonald I. A. et al., Semicarbazide Sensitive Amine Oxidase and Vascular Adhesion Protein-1: One Protein Being Validated as a Therapeutic Target for Inflammatory Diseases. *Annual Reports in Medicinal Chemistry*, 2008, Vol 43.

A family of modestly potent propargylamine compounds was reported to inhibit SSAO/VAP-1 from a number of diverse species (O'Connell, K. M. et al., Differential inhibition of six copper amine oxidases by a family of 4-(aryloxy)-2-butynamines: Evidence for a new mode of inactivation. *Biochemistry* 2004, 43, 10965-10978 and WO2007/005737)

with activity in the micromolar range. Other SSAO/VAP-1 inhibitors have appeared in the patent literature in recent times. Many of these compounds, like semicarbazide, rely upon a hydrazine functional group to form a covalent imine bond with the TPQ cofactor. Two examples are presented below and can be found in the patent publications from La Jolla Pharmaceutical Company (LJPC, WO 2006/094201) and Biotie Therapies Corporation (U.S. Pat. No. 6,624,202). Examples from these series of inhibitors were shown to be effective in a number of in vivo inflammation models, such as mouse ulcerative colitis, mouse LPS-induced septic shock, rat carrageenan foot models, in a mouse model that resembles human multiple sclerosis, in various rodent models of arthritis, and in a transient forebrain ischemia model in estrogen-treated ovariectomized female rats. Some of these hydrazine-based inhibitors were reported to show selective inhibition of SSAO/VAP-1 compared to MAO. However, these compounds are not necessarily desirable therapeutic compounds since the hydrazine functional group is frequently associated with undesirable side effects.

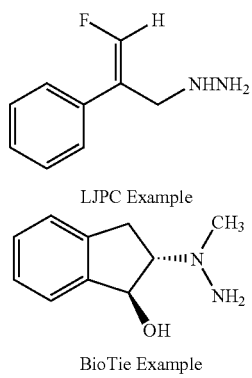

LJPC Example

BioTie Example

Other families of SSAO/VAP-1 inhibitors have appeared recently in the scientific and patent literature and these are also described in the review cited previously (McDonald I. A. et al.). Some of these compounds, such as the thiazole heterocylic series from Astellas, are reported to be very potent against the rat and human enzyme. One example is shown below. It is reported that these did not inhibit MAO. Another compound was claimed to inhibit damage to vascular permeability in the eyes of streptozotocin-induced diabetic rats.

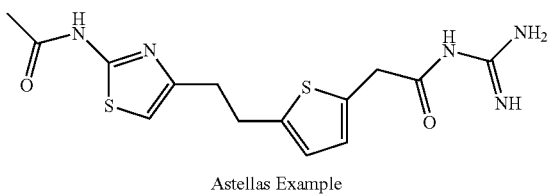 [SMILES: CC(=O)Nc1nc(CCc2ccc(CC(=O)NC(=N)N)s2)cs1]

Astellas Example

Haloallylamine compounds that differ from Mofegiline in core structure have been synthesized and were shown to inhibit the amine oxidase activity from copper-dependent amine oxidases from a number of species (see Kim J. et al., Inactivation of bovine plasma amine oxidase by haloallylamines. *Bioorg Med Chem* 2006, 14, 1444-1453). These compounds have been included in a patent application (Sayre, L. WO 2007/005737).

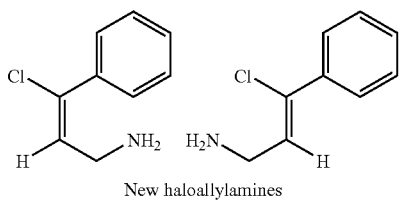 [SMILES: NC/C=C(/Cl)c1ccccc1 ; NC/C=C(\Cl)c1ccccc1]

New haloallylamines

A number of publications discuss these and other amine oxidase inhibitors, but none of these inhibitors were tested as inhibitors of human SSAO/VAP-1 (see Lee Y et al., 3-Pyrrolines are mechanism-based inactivators of the quinone-dependent amine oxidases but only substrates of the flavin-dependent amine oxidases. *J Am Chem Soc* 2002, 124, 12135-12143; Zhang Y. et al., Highly potent 3-pyrroline mechanism-based inhibitors of bovine plasma amine oxidase and mass spectrometric confirmation of cofactor derivatization. *Bioorg Med Chem* 2007, 15, 1868-1877).

2-Halo-substituted-4-amino-2-butenoic acid and ester derivatives are known in the literature (see, for example, Chebib M., et al., Analogs of γ-aminobutyric acid (GABA) and trans-4-aminocrotonic acid (TACA) substituted in the 2 position as GABAC receptor antagonists. *Brit J Pharmacol*, 1997, 122, 1551-1560; Silverman R. B. and George C., Inactivation of γ-aminobutyric acid aminotransaminase by (Z)-4-amino-2-fluorobut-2-enoic acid. Biochemistry, 1988, 27, 3285-3289). These compounds are described in the patent application WO2007/005737 (Amine oxidase inhibitors) where they are claimed to inhibit copper-dependent amine oxidases and methods of using such inhibitors for therapeutic applications. There was no recognition, however, of the inhibitory effects of these compounds against human SSAO/VAP-1.

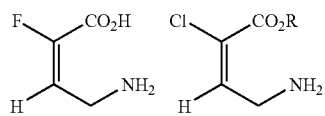

3-Adamantyl-substituted 3-chloroallyamine has been reported in the literature, but there is no indication, however, of whether this compound inhibits SSAO/VAP-1 or any other amine oxidase enzyme (Vashkevich E. V. et al., Synthesis of trichloronitrodienamino adamantine derivatives. *Russian J Applied Chem*, 1999, 35, 1773-1776; Vashkevich E. V. et al., Synthesis of surfactants derived from adamantane. *Russian J Applied Chem*, 2001, 74, 1892-1989).

SUMMARY OF THE INVENTION

In one aspect, the present invention provides substituted haloallylamine compounds that inhibit SSAO/VAP-1. Surprisingly, modification of 3-substituted-3-haloallylamine structures described in the prior art has led to the discovery of novel compounds that are potent inhibitors of the human SSAO/VAP-1 enzyme. Furthermore, certain of these novel compounds are also inhibitors of MAO-B.

Invention compounds are useful for a variety of applications, e.g., for the treatment of the symptoms of inflammation in human subjects as well as in pets and livestock. Human inflammatory diseases include arthritis, Crohn's disease, irritable bowel disease, psoriasis, asthma, chronic pulmonary obstructive disease, bronchiectasis, artherosclerosis, inflammation due to diabetes, and inflammatory cell-mediated tissue destruction following stroke. Another aspect of the present invention provides substituted haloallylamine compounds that inhibit SSAO/VAP-1 and MAO-B with similar efficacy. Certain of these SSAO/VAP-1/MAO-B inhibitors are useful for the treatment of psychological diseases (such as major depression, bipolar depression, and attention deficit hyperactivity disorder), neurodegenerative disorders (such as Parkinson's disease and Alzheimer's disease), and the like.

In another aspect, the present invention describes the synthesis and use of compounds which inhibit the amine oxidase activity of SSAO/VAP-1, and describes the use of such inhibitors to treat patients suffering inflammatory diseases.

In another aspect, the present invention describes the synthesis and use of compounds which inhibit both MAO-B and SSAO/VAP-1 at the same time, and describes the use of such inhibitors to treat patients suffering from neurodegenerative processes.

DETAILED DESCRIPTION OF THE INVENTION

In accordance with the present invention, there are provided compounds having the structure (Formula I):

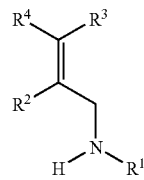

Formula I or stereoisomers, enantiomers, diastereoisomers, polymorphic forms, or pharmaceutically acceptable derivatives thereof; wherein:

$R^1$ is hydrogen or lower alkyl;

$R^2$ is hydrogen, substituted or unsubstituted lower alkyl, bromine, chlorine or fluorine;

$R^3$ and $R^4$ are independently hydrogen, bromine, chlorine, fluorine, substituted or unsubstituted -alkyl-B—$R^5$—$R^6$, substituted or unsubstituted -alkenyl-B—$R^5$—$R^6$, substituted or unsubstituted -alkynyl-B—$R^5$—$R^6$, substituted or unsubstituted -cycloalkyl-B—$R^5$—$R^6$, substituted or unsubstituted -cycloalkenyl-B—$R^5$—$R^6$, or substituted or unsubstituted -heterocyclyl-B—$R^5$—$R^6$; provided, however, that one of $R^3$ and $R^4$ is bromine, chlorine or fluorine, but both $R^3$ and $R^4$ are not bromine, chlorine or fluorine at the same time;

B is selected from oxygen, sulfur, —S(O)$_2$—, —S(O)NH—, —S(O)$_2$NH— or —NHC(O)NH—, $R^5$ is substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkylaryl, substituted or unsubstituted alkylheteroaryl, substituted or unsubstituted alkenylaryl, substituted or unsubstituted alkenylheteroaryl, substituted or unsubstituted alkynylaryl, or substituted or unsubstituted alkynylheteroaryl; and $R^6$ is hydrogen or a functional group which improves the performance properties of the resulting compounds, e.g., potency, selectivity against MAOB, as well as the solubility and/or drug-like properties of said compound.

Functional groups which improve the performance properties of the resulting compounds, e.g., potency, selectivity against MAOB, as well as the solubility and/or drug-like properties of invention compounds include radicals bearing such functionalities as morpholines, piperidines, sulfones, sulfonamides, carboxamides, and the like. Examples of $R^6$ include:

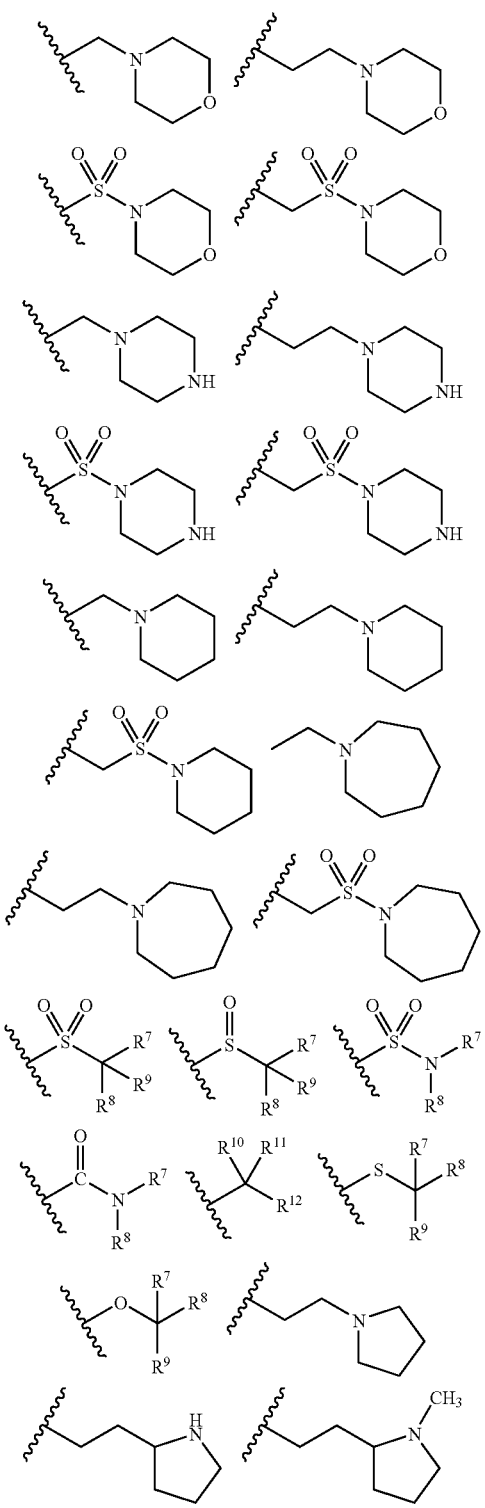

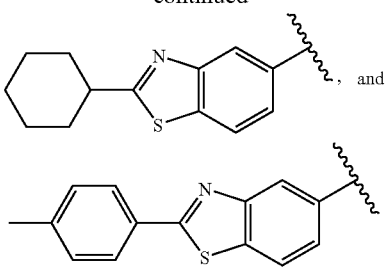

wherein:
each of $R^7$ and $R^8$ are independently hydrogen, substituted or unsubstituted aryl, substituted or unsubstituted heteroaryl, substituted or unsubstituted heterocyclyl, substituted or unsubstituted alkyl, substituted or unsubstituted cycloalkyl, substituted or unsubstituted alkenyl, substituted or unsubstituted cycloalkenyl, substituted or unsubstituted alkynyl, substituted or unsubstituted alkylaryl, or substituted or unsubstituted alkylheteroaryl; or $R^7$ and $R^8$ may cooperate to form a substituted or unsubstituted cycloalkyl, cycloalkenyl, heterocycloalkyl, or heterocycloalkenyl ring system;

$R^9$ is hydrogen, amido, carboximido, lower alkylamido, cycloalkylamido, lower alkylcarboximido, or cycloalkylcarboximido;

each of $R^{10}$ and $R^{11}$ are independently hydrogen, substituted or unsubstituted alkyl, substituted or unsubstituted alkenyl, or substituted or unsubstituted alkynyl; and $R^{12}$ is selected from substituted or unsubstituted alkyl, substituted or unsubstituted alkenyl, substituted or unsubstituted alkynyl, substituted or unsubstituted alkylaryl, alkylheteroaryl, substituted or unsubstituted alkylheteroaryl, amido, carboximido, lower alkylamido, cycloalkylamido, lower alkylcarboximido, or cycloalkylcarboximido.

Presently preferred examples of $R^6$ include:

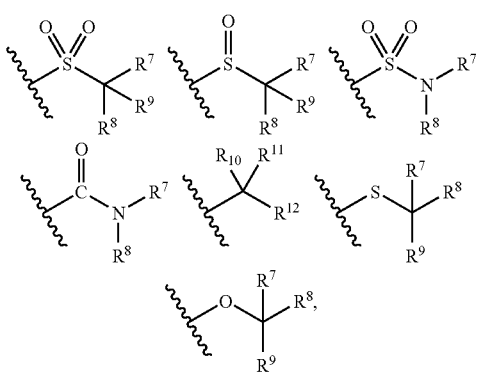

wherein $R^7$, $R^8$, $R^9$, $R^{10}$, $R^{11}$ and $R^{12}$ are as defined above.

In the above structural formulae and throughout the present specification, the following terms have the indicated meaning:

"Lower alkyl" alone or in combination means an alkane-derived radical containing from 1 to 6 carbon atoms (unless specifically defined) that includes a straight chain alkyl or branched alkyl. The straight chain or branched alkyl group is attached at any available point to produce a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like. "Optionally substituted lower alkyl" denotes lower alkyl that is independently substituted, with one or more, preferably 1, 2, 3, 4 or 5, also 1, 2, or 3 substituents, attached at any available atom to produce a stable compound. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. While it is understood that substitutions are attached at any available atom to produce a stable compound, when optionally substituted alkyl is an R group of a moiety such as —OR, —NHR, —C(O)NHR, and the like, substitution of the alkyl R group is such that substitution of the alkyl carbon bound to any —O—, —S—, or —N— of the moiety (except where —N— is a heteroaryl ring atom) excludes substituents that would result in any —O—, —S—, or —N— of the substituent (except where —N— is a heteroaryl ring atom) being bound to the alkyl carbon bound to any —O—, —S—, or —N— of the moiety.

In general, "substituted" refers to an organic group as defined herein (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sufides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitriles (i.e. CN); and the like.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined herein.

The phrase "alkyl" refers to hydrocarbyl chains comprising from 1 to 20 carbon atoms. The phrase "alkyl" includes straight chain alkyl groups, such as methyl, ethyl, propyl, butyl, pentyl, hexyl, heptyl, octyl, nonyl, decyl, undecyl, dodecyl, and the like. The phrase also includes branched chain isomers of straight chain alkyl groups, including but not limited to, the following which are provided by way of example: —CH(CH₃)₂, —CH(CH₃)(CH₂CH₃), —CH(CH₂CH₃)₂, —C(CH₃)₃, —C(CH₂CH₃)₃, —CH₂CH(CH₃)₂, —CH₂CH(CH₃)(CH₂CH₃), —CH₂CH(CH₂CH₃)₂, —CH₂C(CH₃)₃, —CH₂C(CH₂CH₃)₃, —CH(CH₃)CH(CH₃)(CH₂CH₃), —CH₂CH₂CH(CH₃)₂, —CH₂CH₂CH(CH₃)(CH₂CH₃), —CH₂CH₂CH(CH₂CH₃)₂, —CH₂CH₂C(CH₃)₃, —CH₂CH₂C(CH₂CH₃)₃, —CH(CH₃)CH₂CH(CH₃)₂, —CH(CH₃)CH(CH₃)CH(CH₃)₂, and —CH(CH₂CH₃)CH(CH₃)CH(CH₃)(CH₂CH₃). Thus, alkyl groups include primary alkyl groups, secondary alkyl groups, and tertiary alkyl groups. Preferred alkyl groups include alkyl groups having from 1 to 16 carbon atoms, or from 1 to 3 carbon atoms, such as methyl, ethyl, propyl, and —CH(CH₃)₂.

The phrase "alkenyl" refers to hydrocarbyl chains comprising from 2 to 20 carbon atoms and comprising at least one carbon-carbon double bond (—C=C—). The phrase "alkenyl" includes straight chain alkenyl groups, as well as branched chain isomers of straight chain alkenyl groups. Preferably, alkenyl groups comprise from 1 to 8 double bond(s). The phrase "substituted alkenyl" refers to an alkenyl group that is substituted according to the definition provided above.

The phrase "alkynyl" refers to hydrocarbyl chains comprising from 2 to 20 carbon atoms and comprising at least one carbon-carbon triple bond (—C≡C—). The phrase "alkynyl" includes straight chain alkynyl groups, as well as branched chain isomers of straight chain alkynyl groups. Preferably, alkynyl groups comprise from 1 to 8 triple bond(s). The phrase "substituted alkynyl" refers to an alkynyl group that is substituted according to the definition provided above.

"Aryl" alone or in combination refers to a monocyclic or bicyclic ring system containing aromatic hydrocarbons such as phenyl or naphthyl, which may be optionally fused with a cycloalkyl of preferably 5-7, more preferably 5-6, ring members. A "substituted aryl" is an aryl that is independently substituted, with one or more, preferably 1, 2, 3, 4 or 5, also 1, 2, or 3 substituents, attached at any available atom to produce a stable compound.

"Heteroaryl" alone or in combination refers to a monocyclic aromatic ring structure containing 5 or 6 ring atoms, or a bicyclic aromatic group having 8 to 10 atoms, or a tricyclic aromatic group having 13-15 atoms, wherein heteroaryl contains one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, benzothiazole, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, and indolyl. "Nitrogen containing heteroaryl" refers to heteroaryl wherein any heteroatoms are N. A "substituted heteroaryl" is a heteroaryl that is independently substituted, with one or more, preferably 1, 2, 3, 4 or 5, also 1, 2, or 3 substituents, attached at any available atom to produce a stable compound.

"Alkylaryl" alone or in combination refers to an alkyl moiety as defined herein, bearing an aryl substituent (as defined herein) appended thereto, and a "substituted alkylaryl" is an alkylaryl that is independently substituted, with one or more, preferably 1, 2, 3, 4 or 5, also 1, 2, or 3 substituents, attached at any available atom to produce a stable compound.

"Alkylheteroaryl" alone or in combination refers to an alkyl moiety as defined herein, bearing a heteroaryl substituent (as defined herein) appended thereto, and a "substituted alkylheteroaryl" is an alkylheteroaryl that is independently substituted, with one or more, preferably 1, 2, 3, 4 or 5, also 1, 2, or 3 substituents, attached at any available atom to produce a stable compound.

"Alkenylaryl" alone or in combination refers to an alkenyl moiety as defined herein, bearing an aryl substituent (as defined herein) appended thereto, and a "substituted alkenylaryl" is an alkenylaryl that is independently substituted, with one or more, preferably 1, 2, 3, 4 or 5, also 1, 2, or 3 substituents, attached at any available atom to produce a stable compound.

"Alkenyheteroaryl" alone or in combination refers to an alkenyl moiety as defined herein, bearing a heteroaryl substituent (as defined herein) appended thereto, and a "substituted alkenylheteroaryl" is an alkenylheteroaryl that is independently substituted, with one or more, preferably 1, 2, 3, 4 or 5, also 1, 2, or 3 substituents, attached at any available atom to produce a stable compound.

"Alkynylaryl" alone or in combination refers to an alkynyl moiety as defined herein, bearing an aryl substituent (as defined herein) appended thereto, and a "substituted alkynylaryl" is an alkynylaryl that is independently substituted, with one or more, preferably 1, 2, 3, 4 or 5, also 1, 2, or 3 substituents, attached at any available atom to produce a stable compound.

"Alkynylheteroaryl" alone or in combination refers to an alkynyl moiety as defined herein, bearing a heteroaryl substituent (as defined herein) appended thereto, and "substituted alkynylheteroaryl" is an alkynylheteroaryl that is independently substituted, with one or more, preferably 1, 2, 3, 4 or 5, also 1, 2, or 3 substituents, attached at any available atom to produce a stable compound.

"Cycloalkyl" refers to saturated, non-aromatic monocyclic, bicyclic or tricyclic carbon ring systems of 3-10, also 3-8, more preferably 3-6, ring members per ring, such as cyclopropyl, cyclopentyl, cyclohexyl, adamantyl, and the like. A "substituted cycloalkyl" is a cycloalkyl that is independently substituted, with one or more, preferably 1, 2, 3, 4 or 5, also 1, 2, or 3 substituents, attached at any available atom to produce a stable compound.

"Cycloalkenyl" refers to unsaturated, non-aromatic monocyclic, bicyclic or tricyclic carbon ring systems of 3-10, also 3-8, more preferably 3-6, ring members per ring, and comprising at least one carbon-carbon double bond (—C=C—). Examples of cycloalkenyl groups include cyclopropenyl, cyclopentenyl, cyclohexenyl, adamantenyl, and the like. A "substituted cycloalkenyl" is a cycloalkenyl that is independently substituted, with one or more, preferably 1, 2, 3, 4 or 5, also 1, 2, or 3 substituents, attached at any available atom to produce a stable compound.

"Heterocyclyl" refers to saturated, or unsaturated, but non-aromatic monocyclic, bicyclic or tricyclic carbon ring systems of 3-10, also 3-8, more preferably 3-6, ring members per ring, wherein one or more of the ring members, preferably 1-4, more preferably 1-3, even more preferably 1-2, are heteroatoms independently selected from the group consisting of O, S, and N. When the ring system is saturated, "heterocyclyl" may also be referred to as "cycloheteroalkyl", and when the ring system is unsaturated, "heterocyclyl" may also be referred to as "cycloheteroalkenyl" or "cycloheteroalkadienyl", depending on the presence of one or more sites of unsaturation in the ring.

A "substituted heterocyclyl" is a heterocyclyl that is independently substituted, with one or more, preferably 1, 2, 3, 4 or 5, also 1, 2, or 3 substituents, attached at any available atom to produce a stable compound.

"Alkylheterocyclyl" refers to an alkyl moiety as defined herein, bearing a heterocyclyl substituent (as defined herein) appended thereto, and a "substituted alkylheterocyclyl" is an alkylheterocyclyl that is independently substituted, with one or more, preferably 1, 2, 3, 4 or 5, also 1, 2, or 3 substituents, attached at any available atom to produce a stable compound.

"Alkenylheterocyclyl" refers to an alkenyl moiety as defined herein, bearing a heterocyclyl substituent (as defined herein) appended thereto, and a "substituted alkenylheterocyclyl" is an alkenylheterocyclyl that is independently substituted, with one or more, preferably 1, 2, 3, 4 or 5, also 1, 2, or 3 substituents, attached at any available atom to produce a stable compound.

"Alkynylheterocyclyl" refers to an alkynyl moiety as defined herein, bearing a heterocyclyl substituent (as defined herein) appended thereto, and a "substituted alkynylheterocyclyl" is an alkynylheterocyclyl that is independently substituted, with one or more, preferably 1, 2, 3, 4 or 5, also 1, 2, or 3 substituents, attached at any available atom to produce a stable compound.

In a particular embodiment of the present invention, there are provided compounds of Formula (Ia):

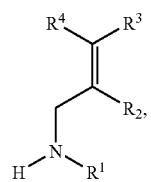

Formula Ia or pharmaceutically acceptable derivatives thereof, wherein:
$R^1$ is hydrogen,
$R^2$ is hydrogen, substituted or unsubstituted lower alkyl, bromine, chlorine or fluorine;
$R^3$ is bromine, chlorine or fluorine;
$R^4$ is substituted or unsubstituted -alkyl-B—$R^5$—$R^6$, substituted or unsubstituted -alkenyl-B—$R^5$—$R^6$, substituted or unsubstituted -alkynyl-B—$R^5$—$R^6$, substituted or unsubstituted -cycloalkyl-B—$R^5$—$R^6$, substituted or unsubstituted -cycloalkenyl-B—$R^5$—$R^6$, or substituted or unsubstituted -heterocyclyl-B—$R^5$—$R^6$;
B is oxygen, sulfur, —S(O$_2$)—, —S(O)NH—, —S(O$_2$)NH— or —NHC(O)NH—;
$R^5$ is substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkylaryl, substituted or unsubstituted alkylheteroaryl, substituted or unsubstituted alkenylaryl, substituted or unsubstituted alkenylheteroaryl, substituted or unsubstituted alkynylaryl, or substituted or unsubstituted alkynyheteroaryl; and
$R^6$ is hydrogen or a functional group which improves the performance properties of the resulting compounds, e.g., potency, selectivity against MAOB, as well as the solubility and/or drug-like properties of said compound.

Functional groups which improve the performance properties of the resulting compounds, e.g., potency, selectivity against MAOB, as well as the solubility and/or drug-like properties of compounds of Formula I include radicals bearing such functionalities as morpholines, piperidines, sulfones, sulfonamides, carboxamides, and the like. Examples of $R^6$ include:

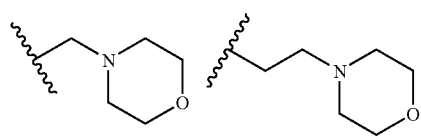

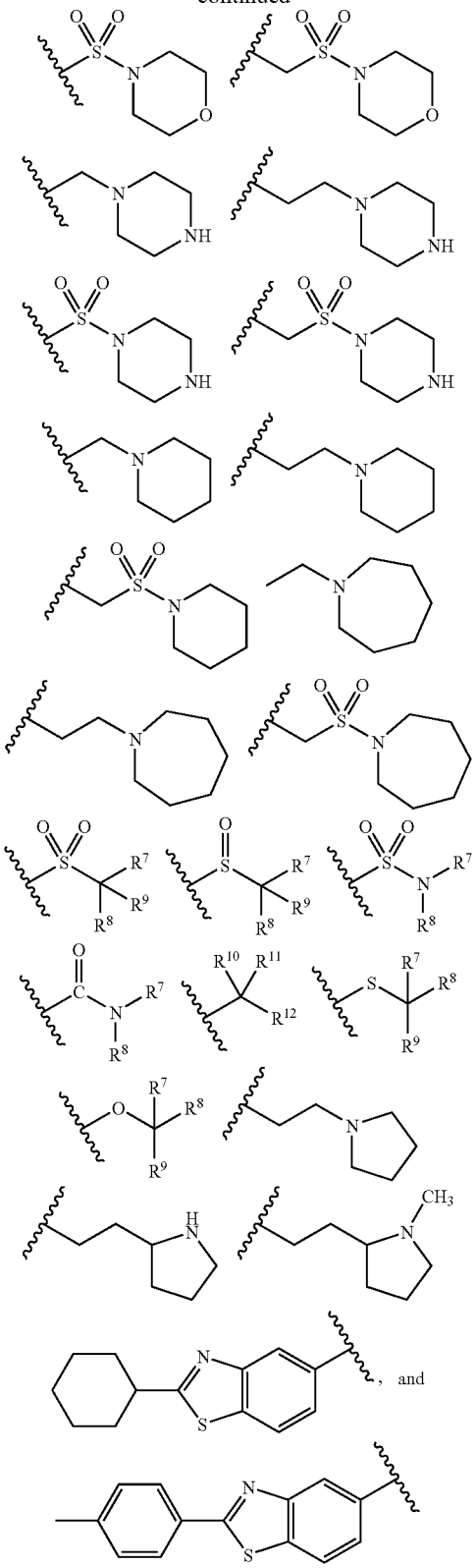

wherein:
each of $R^7$ and $R^8$ are independently hydrogen, substituted or unsubstituted aryl, substituted or unsubstituted heteroaryl, substituted or unsubstituted heterocyclyl, substituted or unsubstituted alkyl, substituted or unsubstituted cycloalkyl, substituted or unsubstituted alkenyl, substituted or unsubstituted cycloalkenyl, substituted or unsubstituted alkynyl, substituted or unsubstituted alkylaryl, or substituted or unsubstituted alkylheteroaryl; or $R^7$ and $R^8$ may cooperate to form a substituted or unsubstituted cycloalkyl, cycloalkenyl, or heterocyclyl ring system;

$R^9$ is hydrogen, amido, carboximido, lower alkylamido, cycloalkylamido, lower alkylcarboximido, or cycloalkylcarboximido;

each of $R^{10}$ and $R^{11}$ are independently hydrogen, substituted or unsubstituted alkyl, substituted or unsubstituted alkenyl, or substituted or unsubstituted alkynyl; and $R^{12}$ is selected from substituted or unsubstituted alkyl, substituted or unsubstituted alkenyl, substituted or unsubstituted alkynyl, substituted or unsubstituted alkylaryl, substituted or unsubstituted alkylheteroaryl, amido, carboximido, lower alkylamido, cycloalkylamido, lower alkylcarboximido, or cycloalkylcarboximido.

Presently preferred examples of $R^6$ include:

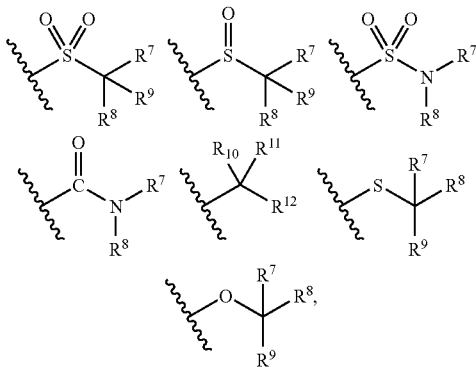

wherein $R^7$, $R^8$, $R^9$, $R^{10}$, $R^{11}$ and $R^{12}$ are as defined above.

In accordance with one embodiment of the present invention, presently preferred compounds include compounds of Formula I wherein $R^3$ is fluorine and B is oxygen.

In accordance with another embodiment of the present invention, presently preferred compounds include compounds of Formula I wherein $R^3$ is chlorine and B is oxygen.

In accordance with yet another embodiment of the present invention, presently preferred compounds include compounds of Formula I wherein $R^4$ is methylene; $R^5$ is substituted aryl; and $R^6$ is selected from the group consisting of:

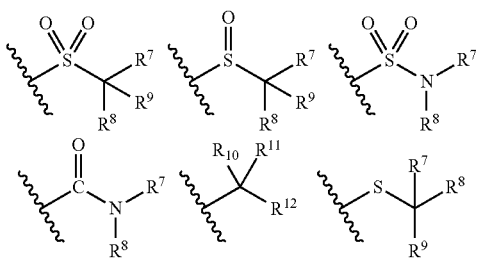

-continued

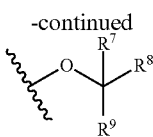

wherein:

each of $R^7$ and $R^8$ are independently hydrogen, substituted or unsubstituted aryl, substituted or unsubstituted heteroaryl, substituted or unsubstituted heterocyclyl, substituted or unsubstituted alkyl, substituted or unsubstituted cycloalkyl, substituted or unsubstituted alkenyl, substituted or unsubstituted cycloalkenyl, substituted or unsubstituted alkynyl, substituted or unsubstituted alkylaryl, or substituted or unsubstituted alkylheteroaryl; or $R^7$ and $R^8$ may cooperate to form a substituted or unsubstituted cycloalkyl, cycloalkenyl, or heterocyclyl ring system;

$R^9$ is hydrogen, amido, carboximido, lower alkylamido, cycloalkylamido, lower alkylcarboximido, or cycloalkylcarboximido;

each of $R^{10}$ and $R^{11}$ are independently hydrogen, substituted or unsubstituted alkyl, substituted or unsubstituted alkenyl, or or unsubstituted alkynyl; and $R^{12}$ is selected from substituted or unsubstituted alkyl, substituted or unsubstituted alkenyl, substituted or unsubstituted alkynyl, substituted or unsubstituted alkylaryl, substituted or unsubstituted alkylheteroaryl, amido, carboximido, lower alkylamido, cycloalkylamido, lower alkylcarboximido, or cycloalkylcarboximido.

In accordance with a still further embodiment of the present invention, presently preferred compounds include compounds of Formula I wherein $R^4$ is methylene; $R^5$ is substituted aryl or benzothiazole; and the remaining R groups are as defined above. In accordance with one preferred aspect of this embodiment of the present invention, compounds include the above-described compounds of Formula I wherein $R^3$ is fluorine and B is oxygen. In accordance with another preferred aspect of this embodiment of the present invention, compounds include the above-described compounds of Formula I wherein $R^3$ is chlorine and B is oxygen.

It is understood that compounds described by Formula I may be administered in a prodrug form wherein the substituent $R^1$ can be selected from such functional groups as —C(O)alkyl, —C(O)aryl, —C(O)-arylalkyl, C(O)heteroaryl, —C(O)-heteroarylalkyl.

The phrase "prodrug" refers to a compound that, upon in vivo administration, is metabolized by one or more steps or processes or otherwise converted to the biologically, pharmaceutically or therapeutically active form of the compound. Prodrugs can be prepared by modifying functional groups present in the compound in such a way that the modifications are cleaved, either in routine manipulation or in vivo, to a compound described herein. For example, prodrugs include compounds of the present invention wherein a hydroxy, amino, or sulfhydryl group is bonded to any group that, when administered to a mammalian subject, can be cleaved to form a free hydroxyl, free amino, or free sulthydryl group, respectively. Representative prodrugs include, for example, amides, esters, enol ethers, enol esters, acetates, formates, benzoate derivatives, and the like of alcohol and amine functional groups in the compounds of the present invention. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

It is also understood that the inventive compounds described by Formula I may be present as E and Z isomers, also known as cis and trans isomers. Compounds of the present invention may have asymmetric centers and may occur, except when specifically noted, as mixtures of stereoisomers or as individual diastereomers, or enantiomers, with all isomeric forms being included in the present invention. Compounds of the present invention embrace all conformational isomers. Compounds of the present invention may also exist in one or more tautomeric forms, including both single tautomers and mixtures of tautomers.

The inventive compounds described by Formula I may exist as acid addition salts when a basic amino group is present, or as metal salts when an acidic group is present.

The phrase "pharmaceutically acceptable salt" refers to any salt preparation that is appropriate for use in a pharmaceutical application. Pharmaceutically-acceptable salts include amine salts of mineral acids (e.g., hydrochlorides, hydrobromides, sulfates, and the like); and amine salts of organic acids (e.g., formates, acetates, lactates, malates, tartrates, citrates, ascorbates, succinates, maleates, butyrates, valerates, fumarates, alkylsulfonates, arylsulfonates, and the like).

The phrase "pharmaceutically acceptable solvates" refers to an aggregation of a molecule and one or more molecules of solvent. Some compounds have a tendency to associate with a fixed molar ratio of solvent molecules in the solid state. The solvent molecules may interact with the non-solvent molecule by dipole-dipole interactions, ion-dipole interactions, coordinate bonds, and the like. When the solvent is water, the solvate is referred to as a hydrate. Many organic solvents can also form solvates, including, e.g., ethers such as diethyl ether and tetrahydrofuran, alcohols such as methanol and ethanol, ketones such as acetone, DMF, DMSO and others. Solvates may be identified by various methods known in the art. For example, solvates in which the solvent molecules contain hydrogen may be observable by $^1$H NMR. Additional methods useful in identifying solvates include thermogravimetric analysis, differential scanning calorimetry, X-ray analysis and elemental analysis. Solvates are readily formed simply by dissolving a compound in a solvent and removing the unassociated solvent by suitable techniques, e.g., evaporation, freeze drying or crystallization techniques. It is therefore well within the skill in the art to produce such solvates. Indeed, it is often the case that careful drying of a compound is necessary to remove the residual solvent that is part of a solvate. Compounds described herein may form solvates and all such solvates are within the scope of the invention.

Exemplary compounds according to the present invention include compounds having the following structures:

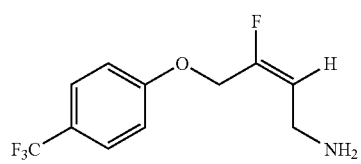

-continued

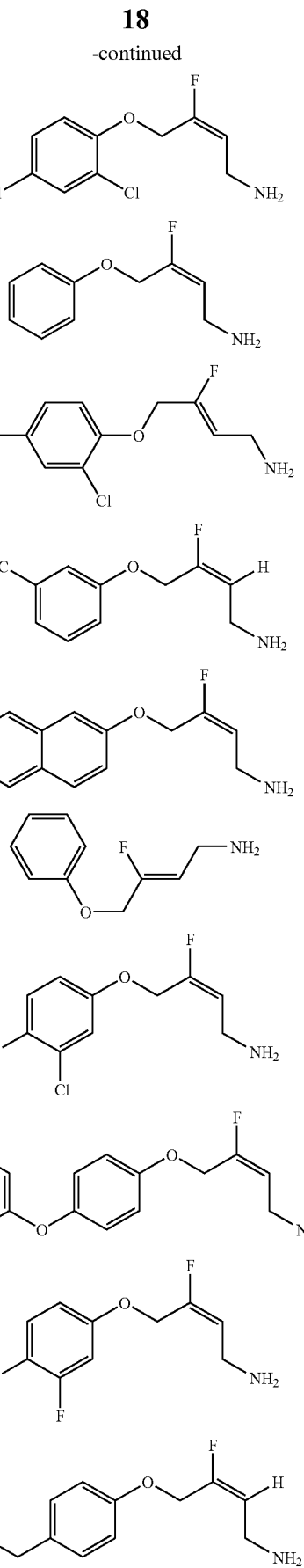

-continued
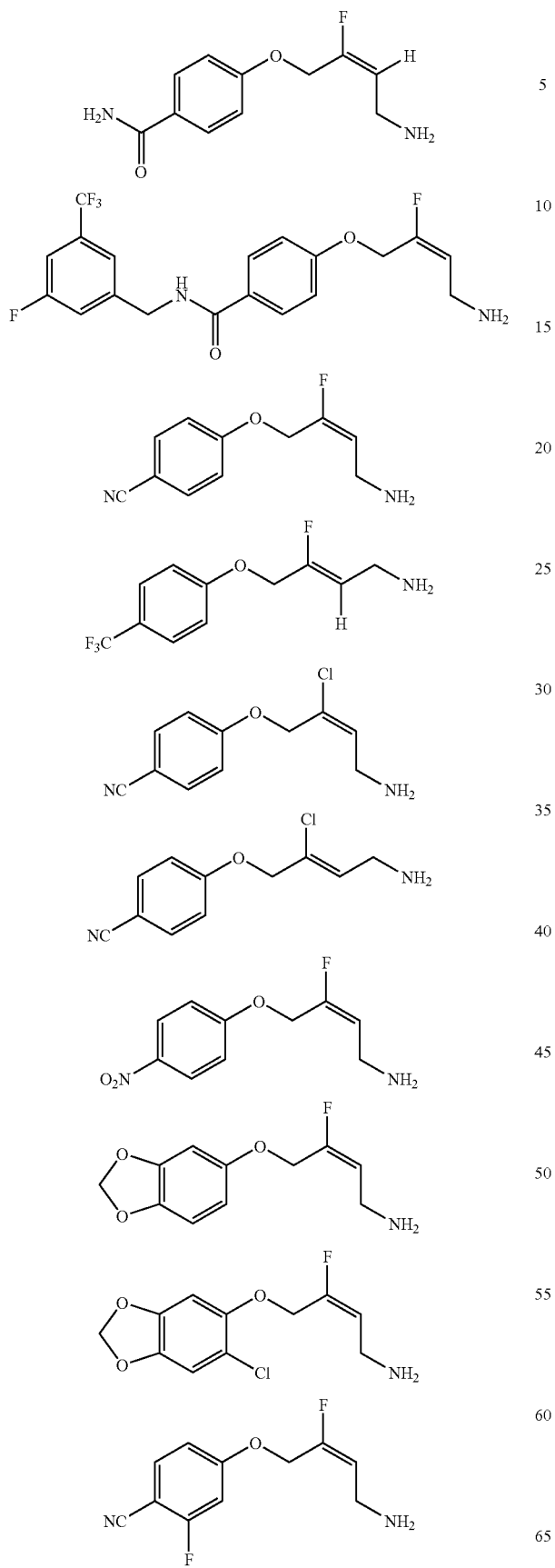
-continued
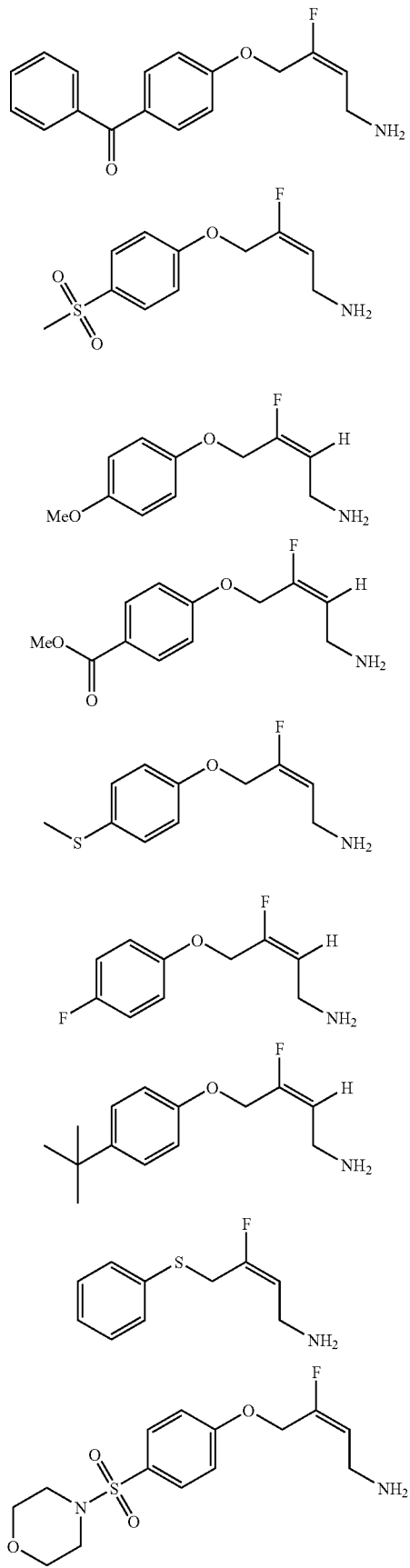

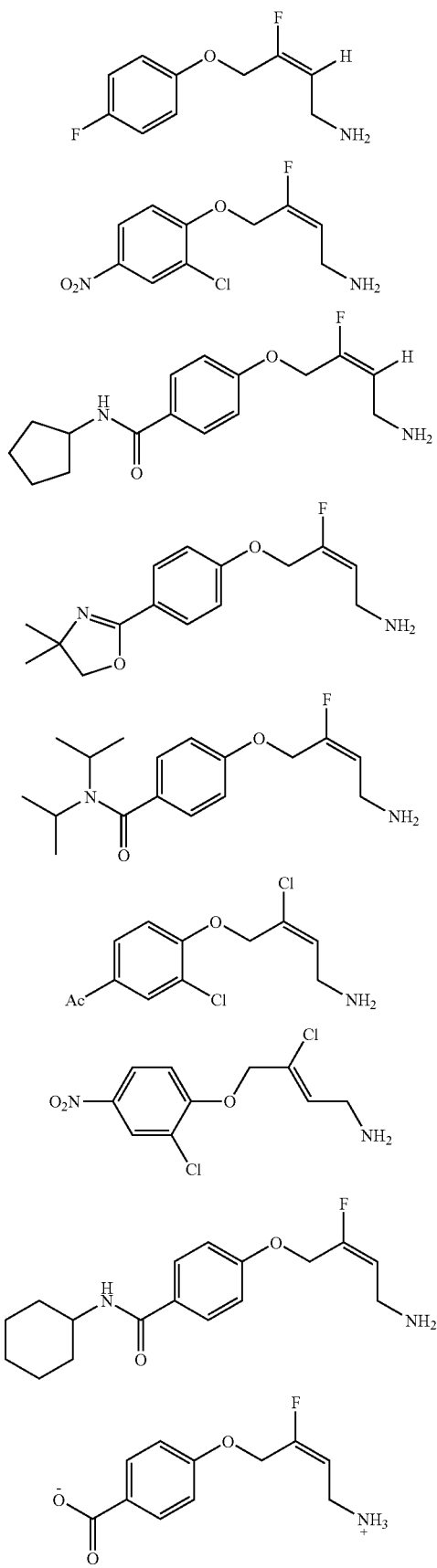
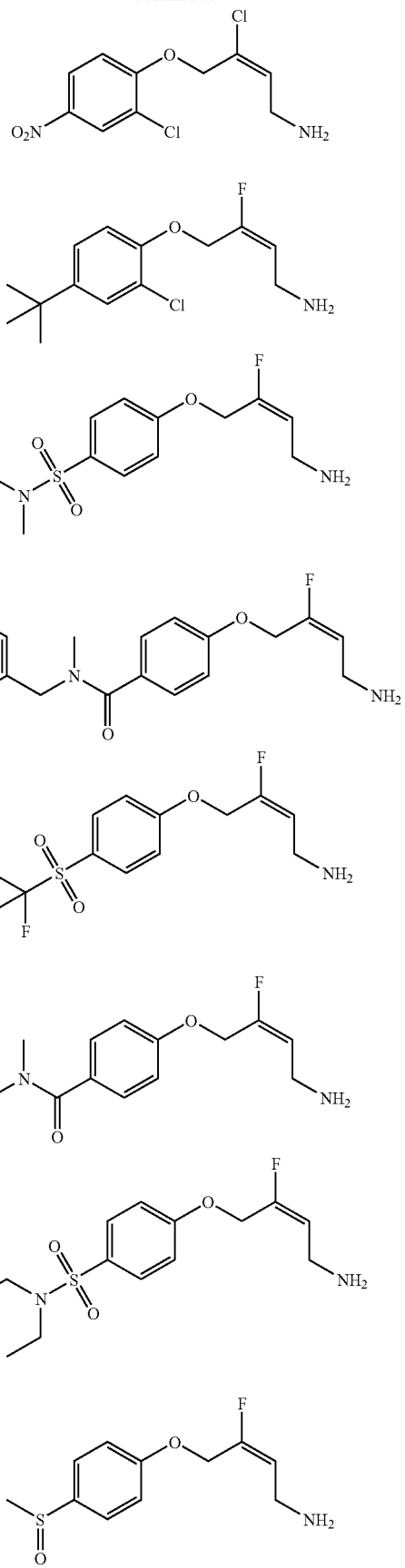

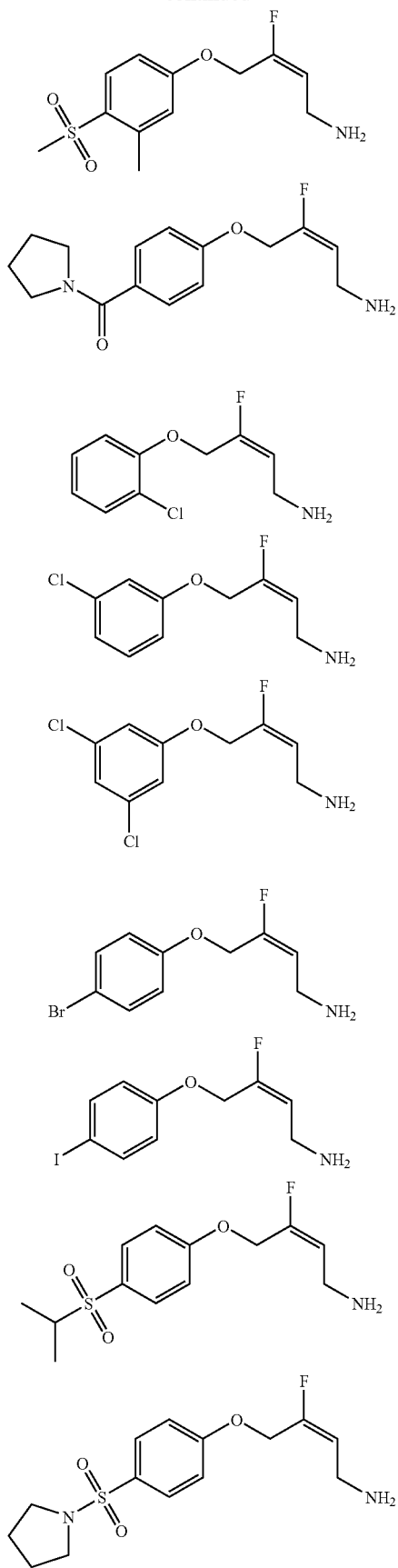
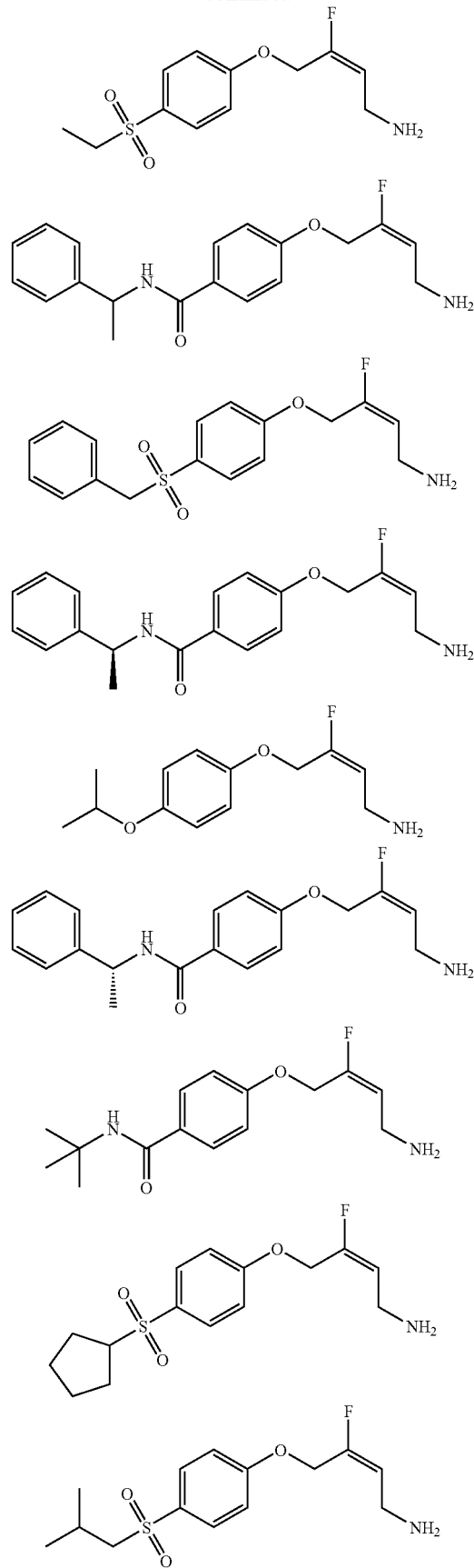

25
-continued
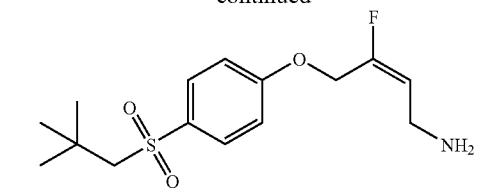
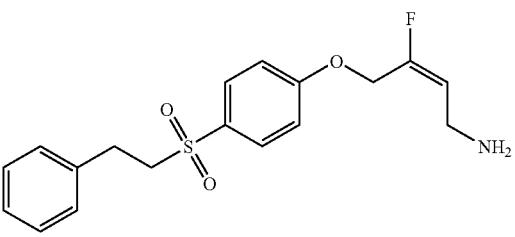
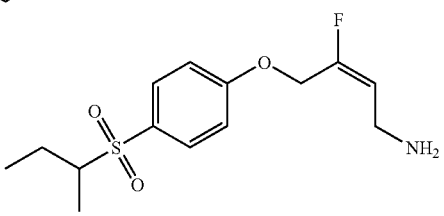
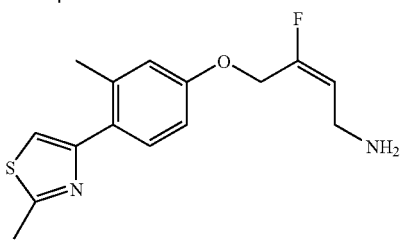
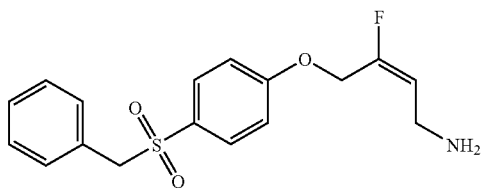
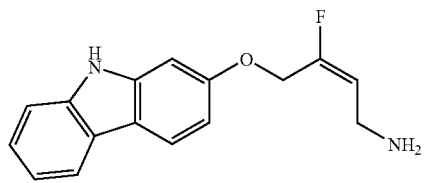
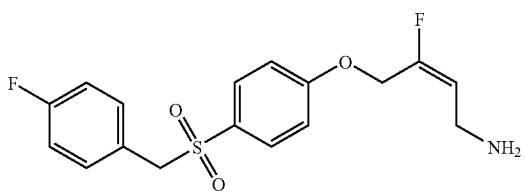
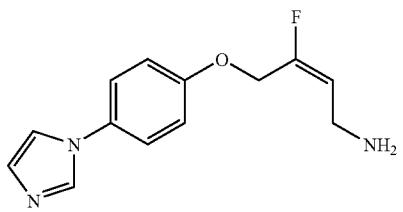
26
-continued
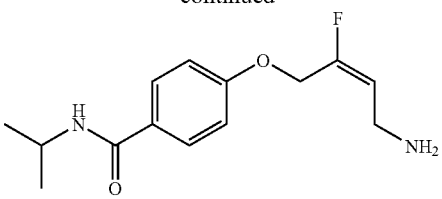
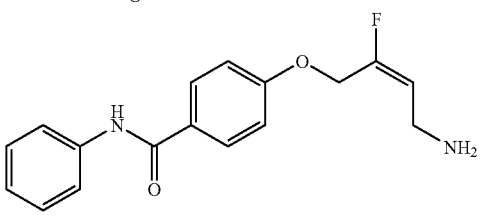
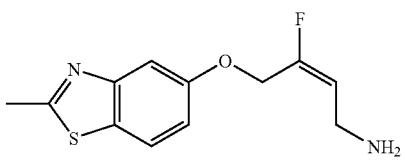
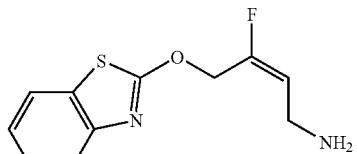
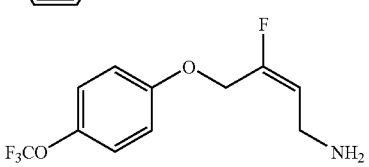
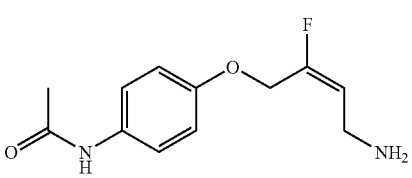
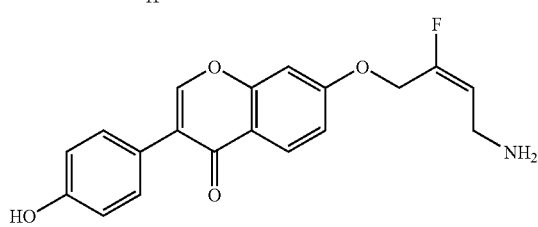
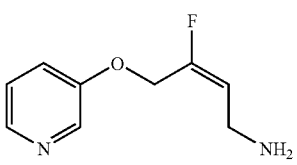
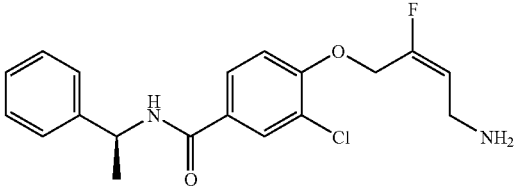

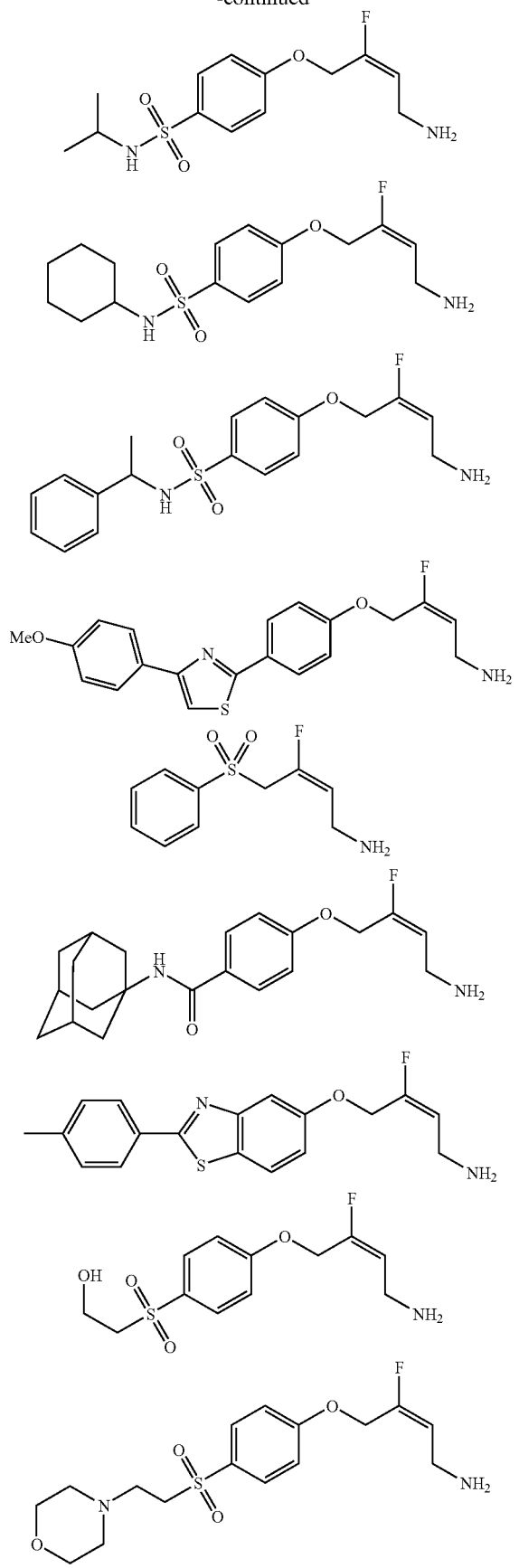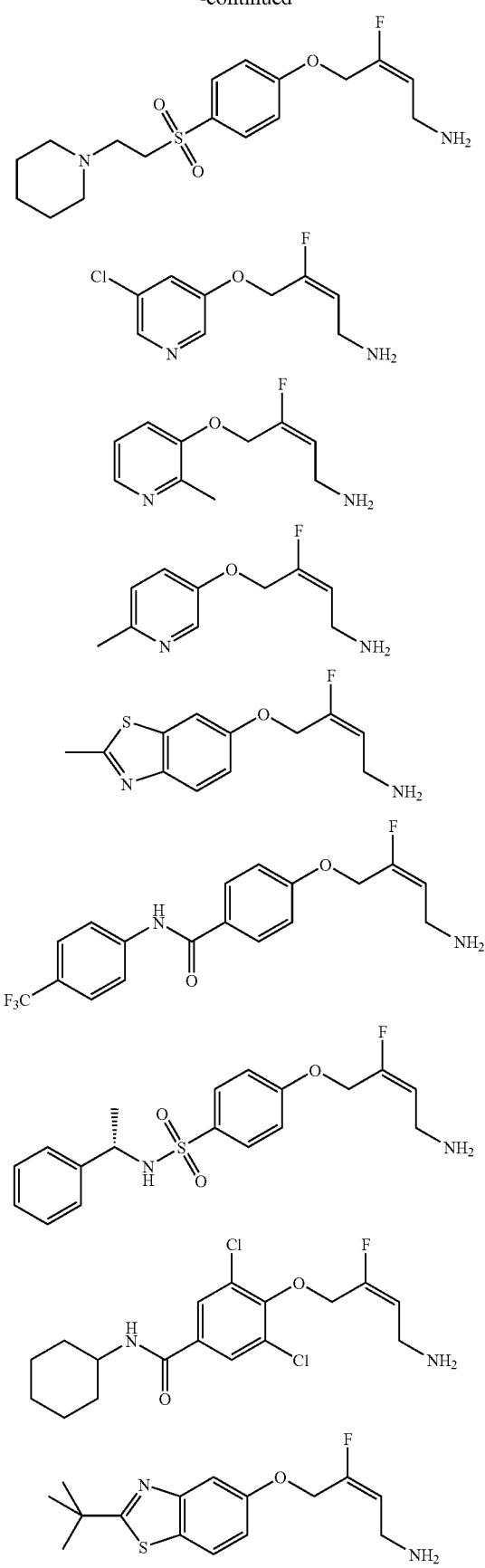

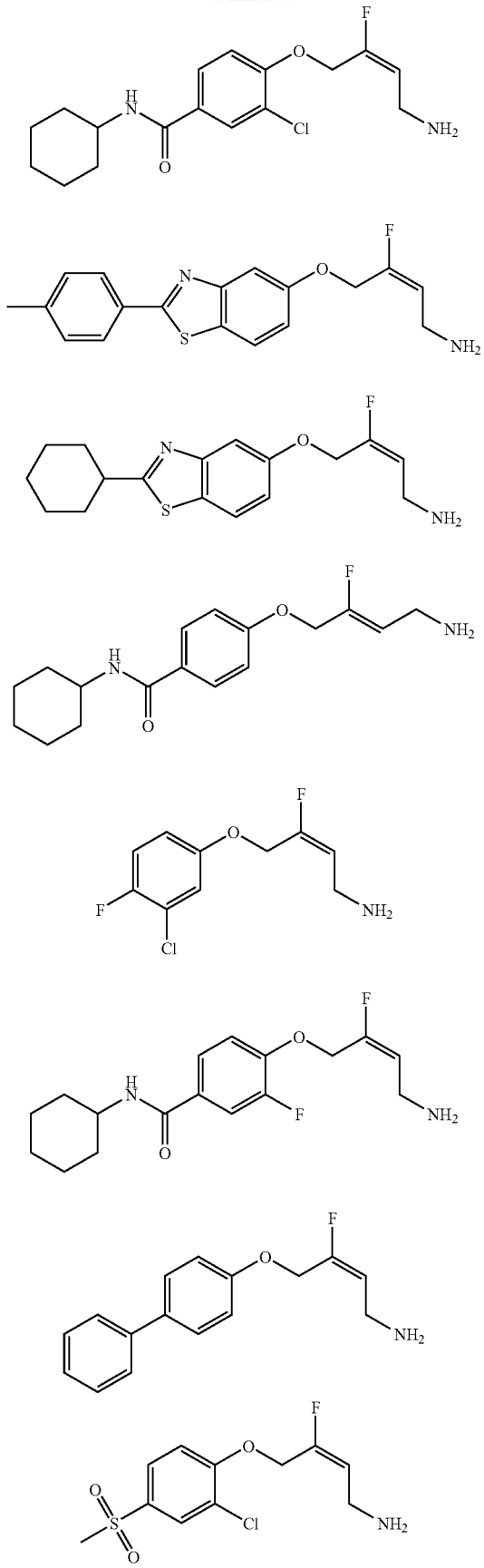
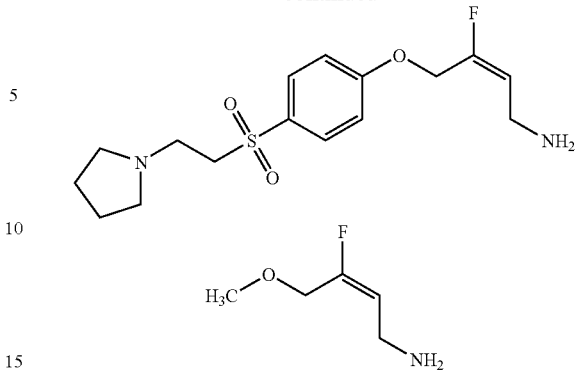

Exemplary compounds according to the present invention include:
(E)-3-Fluoro-4-phenoxybut-2-en-1-amine,
(E)-3-Fluoro-4-(4-(trifluoromethyl)phenoxy)but-2-en-1-amine,
(E)-4-(2,4-Dichlorophenoxy)-3-fluorobut-2-en-1-amine,
(E)-3-Fluoro-4-(4-methoxyphenoxy)but-2-en-1-amine,
(E)-4-(4-Amino-2-fluorobut-2-enyloxy)benzamide,
(E)-4-(3,4-Difluorophenoxy)-3-fluorobut-2-en-1-amine,
(E)-3-Fluoro-4-(4-nitrophenoxy)but-2-en-1-amine,
(E)-4-(4-tert-Butylphenoxy)-3-fluorobut-2-en-1-amine,
(Z)-3-Fluoro-4-(4-(trifluoromethyl)phenoxy)but-2-en-1-amine,
(E)-3-Fluoro-4-(3-(trifluoromethyl)phenoxy)but-2-en-1-amine,
(E)-3-Fluoro-4-(4-fluorophenoxy)but-2-en-1-amine,
(E)-3-Fluoro-4-(4-(methylsulfonyl)phenoxy)but-2-en-1-amine,
(E)-3-Fluoro-4-(4-(morpholinosulfonyl)phenoxy)but-2-en-1-amine,
(E)-4-(4-Amino-2-fluorobut-2-enyloxy)-N,N-diisopropylbenzamide,
(E)-4-(4-Amino-2-fluorobut-2-enyloxy)-N-benzylbenzamide,
(Z)-3-Fluoro-4-phenoxybut-2-en-1-amine,
(Z)-4-(2,4-Dichlorophenoxy)-3-fluorobut-2-en-1-amine,
(E)-4-(3-Chloro-4-fluorophenoxy)-3-fluorobut-2-en-1-amine,
(E)-3-Fluoro-4-(4-phenoxyphenoxy)but-2-en-1-amine,
(E)-4-(4-Amino-2-fluorobut-2-enyloxy)benzonitrile,
(E)-4-(4-Amino-2-fluorobut-2-enyloxy)-2-fluorobenzonitrile,
(E)-4-(Benzo[d][1,3]dioxol-5-yloxy)-3-fluorobut-2-en-1-amine,
(E)-3-Fluoro-4-(naphthalen-2-yloxy)but-2-en-1-amine,
(E)-(4-(4-Amino-2-fluorobut-2-enyloxy)phenyl)(phenyl)methanone,
(E)-4-(2-Chloro-4-nitrophenoxy)-3-fluorobut-2-en-1-amine,
(E)-4-(6-Chlorobenzo[d][1,3]dioxol-5-yloxy)-3-fluorobut-2-en-1-amine,
(E)-4-(4-Amino-2-fluorobut-2-enyloxy)-N-(3-fluoro-5-(trifluoromethyl)benzyl)benzamide,
(E)-3-Fluoro-4-(4-(morpholinosulfonyl)phenoxy)but-2-en-1-amine,
(E)-4-(4-(4,4-Dimethyl-4,5-dihydrooxazol-2-yl)phenoxy)-3-fluorobut-2-en-1-amine,
(E)-3-Fluoro-4-(4-(methylsulfonyl)phenoxy)but-2-en-1-amine,
(Z)-3-Chloro-4-(2-chloro-4-nitrophenoxy)but-2-en-1-amine, (E)-3-Chloro-4-(2-chloro-4-nitrophenoxy)but-2-en-1-amine,
(E)-3-Fluoro-4-(4-(methylthio)phenoxy)but-2-en-1-amine,
(E)-4-(4-tert-Butyl-2-chlorophenoxy)-3-fluorobut-2-en-1-amine,
(E)-3-Fluoro-4-(2-chloro-4-(methylsulfonyl)phenoxy)but-2-en-1-amine,
(E)-4-(4-Amino-2-fluorobut-2-enyloxy)-N-cyclopentylbenzamide,
(E)-4-(4-Amino-2-fluorobut-2-enyloxy)-N,N-dimethylbenzenesulfonamide,
(E)-4-(4-Amino-2-fluorobut-2-enyloxy)-N-benzyl-N-methylbenzamide,
(E)-3-Fluoro-4-(4-(trifluoromethylsulfonyl)phenoxy)but-2-en-1-amine,
(E)-4-(4-Amino-2-fluorobut-2-enyloxy)-N,N-dimethylbenzamide,
(E)-4-(4-Amino-2-fluorobut-2-enyloxy)-N,N-diethylbenzenesulfonamide,
(E)-3-Fluoro-4-(4-(methylsulfinyl)phenoxy)but-2-en-1-amine,
(E)-3-Fluoro-4-(3-methyl-4-(methylsulfonyl)phenoxy)but-2-en-1-amine,
(E)-(4-(4-Amino-2-fluorobut-2-enyloxy)phenyl)(pyrrolidin-1-yl)methanone,
(E)-4-(2-Chlorophenoxy)-3-fluorobut-2-en-1-amine,
(E)-4-(3,5-Dichlorophenoxy)-3-fluorobut-2-en-1-amine,
(E)-4-(4-Bromophenoxy)-3-fluorobut-2-en-1-amine,
(E)-3-Fluoro-4-(4-iodophenoxy)but-2-en-1-amine,
(E)-3-Fluoro-4-(4-(isopropylsulfonyl)phenoxy)but-2-en-1-amine,
(E)-3-Fluoro-4-(4-(pyrrolidin-1-ylsulfonyl)phenoxy)but-2-en-1-amine,
(E)-4-(4-(Ethylsulfonyl)phenoxy)-3-fluorobut-2-en-1-amine,
R/S-(E)-4-(4-Amino-2-fluorobut-2-enyloxy)-N-(1-phenylethyl)benzamide,
(E)-4-(4-(Benzylsulfonyl)phenoxy)-3-fluorobut-2-en-1-amine,
(E)-4-(Biphenyl-4-yloxy)-3-fluorobut-2-en-1-amine,
(E)-4-(4-amino-2-fluorobut-2-enyloxy)-N-cyclohexylbenzamide,
S-(E)-4-(4-Amino-2-fluorobut-2-enyloxy)-N-(1-phenylethyl)benzamide,
R-(E)-4-(4-Amino-2-fluorobut-2-enyloxy)-N-(1-phenylethyl)benzamide,
(E)-3-Fluoro-4-(phenylthio)but-2-en-1-amine,
(E)-3-Fluoro-4-(4-isopropoxyphenoxy)but-2-en-1-amine,
(E)-4-(4-Amino-2-fluorobut-2-enyloxy)-N-tert-butylbenzamide,
(E)-4-(4-(Cyclopentylsulfonyl)phenoxy)-3-fluorobut-2-en-1-amine,
(E)-3-Fluoro-4-(4-(isobutylsulfonyl)phenoxy)but-2-en-1-amine,
(E)-3-Fluoro-4-(4-(neopentylsulfonyl)phenoxy)but-2-en-1-amine,
(E)-3-Fluoro-4-(4-(phenethylsulfonyl)phenoxy)but-2-en-1-amine,
(E)-4-(4-(sec-Butylsulfonyl)phenoxy)-3-fluorobut-2-en-1-amine,
(E)-3-Fluoro-4-(4-(1-phenylethylsulfonyl)phenoxy)but-2-en-1-amine,
(E)-3-Fluoro-4-(4-(4-fluorobenzylsulfonyl)phenoxy)but-2-en-1-amine,
(E)-4-(9H-Carbazol-2-yloxy)-3-fluorobut-2-en-1-amine,
(E)-4-(4-(1H-Imidazol-1-yl)phenoxy)-3-fluorobut-2-en-1-amine,
(E)-4-(4-Amino-2-fluorobut-2-enyloxy)-N-isopropylbenzamide,
(E)-4-(4-Amino-2-fluorobut-2-enyloxy)-N-phenylbenzamide,
(E)-3-Fluoro-4-(2-methylbenzo[d]thiazol-5-yloxy)but-2-en-1-amine,
(E)-4-(Benzo[d]thiazol-2-yloxy)-3-fluorobut-2-en-1-amine,
(E)-N-(4-(4-Amino-2-fluorobut-2-enyloxy)phenyl)acetamide,
(E)-7-(4-Amino-2-fluorobut-2-enyloxy)-3-(4-hydroxyphenyl)-4H-chromen-4-one,
(E)-3-Fluoro-4-(pyridin-3-yloxy)but-2-en-1-amine,
(E)-3-Fluoro-4-(2-p-tolylbenzo[d]thiazol-6-yloxy)but-2-en-1-amine,
(E)-2-(4-(4-Amino-2-fluorobut-2-enyloxy)phenylsulfonyl)ethanol,
(E)-3-Fluoro-4-(4-(2-morpholinoethylsulfonyl)phenoxy)but-2-en-1-amine,
(E)-3-Fluoro-4-(4-(2-(pyrrolidin-1-yl)ethylsulfonyl)phenoxy)but-2-en-1-amine,
(E)-3-Fluoro-4-(4-(2-(piperidin-1-yl)ethylsulfonyl)phenoxy)but-2-en-1-amine,
(E)-3-Fluoro-4-(2-methylpyridin-3-yloxy)but-2-en-1-amine,
(E)-3-Fluoro-4-(6-methylpyridin-3-yloxy)but-2-en-1-amine,
(E)-3-Fluoro-4-(2-methylbenzo[d]thiazol-6-yloxy)but-2-en-1-amine,
(E)-4-(4-Amino-2-fluorobut-2-enyloxy)-N-isopropylbenzenesulfonamide,
(E)-4-(4-Amino-2-fluorobut-2-enyloxy)-N-cyclohexylbenzenesulfonamide,
(E)-4-(4-Amino-2-fluorobut-2-enyloxy)-N-(1-phenylethyl)benzenesulfonamide,
(E)-3-Fluoro-4-(4-(4-(4-methoxyphenyl)thiazol-2-yl)phenoxy)but-2-en-1-amine,
(E)-3-Fluoro-4-(phenylsulfonyl)but-2-en-1-amine,
S-(E)-4-(4-Amino-2-fluorobut-2-enyloxy)-N-(1-phenylethyl)benzenesulfonamide,
(E)-4-(2-tert-Butylbenzo[d]thiazol-5-yloxy)-3-fluorobut-2-en-1-amine,
(E)-3-Fluoro-4-(2-p-tolylbenzo[d]thiazol-5-yloxy)but-2-en-1-amine,
(E)-4-(2-Cyclohexylbenzo[d]thiazol-5-yloxy)-3-fluorobut-2-en-1-amine,
(E)-3-Fluoro-4-methoxybut-2-en-1-amine,
(Z)-4-(4-Amino-2-fluorobut-2-enyloxy)-N-cyclohexylbenzamide,
(E)-3-Fluoro-4-(4-(trifluoromethoxy)phenoxy)but-2-en-1-amine,
S-(E)-4-(4-Amino-2-fluorobut-2-enyloxy)-3-chloro-N-(1-phenylethyl)benzamide,
(E)-4-(4-Amino-2-fluorobut-2-enyloxy)-N-(adamantyl)benzamide,
(E)-4-(4-Amino-2-fluorobut-2-enyloxy)-N-(4-(trifluoromethyl)phenyl)benzamide,
(E)-4-(4-Amino-2-fluorobut-2-enyloxy)-3,5-dichloro-N-cyclohexylbenzamide,
(E)-4-(4-Amino-2-fluorobut-2-enyloxy)-3-chloro-N-cyclohexylbenzamide,
(E)-4-(4-Amino-2-fluorobut-2-enyloxy)-N-cyclohexyl-3-fluorobenzamide,
(E)-4-(4-Amino-2-fluoro-3-methylbut-2-enyloxy)-N-cyclohexylbenzamide, and
(Z)-4-(4-Amino-2-fluoro-3-methylbut-2-enyloxy)-N-cyclohexylbenzamide.

The compounds of the invention can be prepared in a variety of ways, such as, for example, employing the synthetic protocol described in Scheme 1, below:

Scheme 1

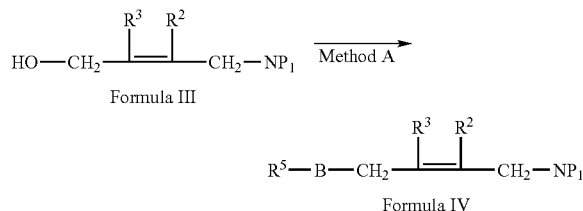

wherein $R^2$, $R^3$, B and $R^5$ are as defined herein; and $P_1$ is a functional group used to protect a nitrogen functionality. Examples of $P_1$ are the tert-butyloxycarbonyl group (BOC) and the phthalimido group.

Compounds represented by Formula III are known in the literature; where specific compounds are not described, these can be prepared by those skilled in the art of organic synthesis by standard procedures.

A compound represented by Formula III is either directly used in a displacement reaction, such as a Mitsunobu reaction, to yield the compound represented by Formula IV, or is first converted to a bromide, chloride or iodide by procedures well known in the art, then treated with a nucleophilic reagent or organometallic reagent to furnish the compound represented by Formula IV (Method A).

The Mitsunobu reaction conditions are well described in the scientific and patent literature (see, for example, the World Wide Web at en.wikipedia.org/wiki/Mitsunobu_reaction, and Mitsunobu, O., The use of diethyl azodicarboxylate and triphenylphosphine in synthesis and transformation of natural products. *Synthesis* 1981, 1-28) and proceed by contacting an alcohol with an appropriately substituted phenolic or thiophenolic group, or a substituted phthalimide in the presence of a dialkyl azodicarboxylate and triphenylphosphine in an organic solvent such as tetrahydrofuran (THF) or CH2Cl2 ($CH_2Cl_2$).

Conversion of the alcohol group in Formula III to the corresponding bromide, chloride or iodide is accomplished by any number of commonly used procedures (See, for example, March J. Advanced Organic Synthesis, John Wiley & Sons, Third Edition 1985), including treatment with $PBr_3$ in toluene or $CBr_4$ and triphenylphosphine in an organic solvent such as $CH_2Cl_2$. The resulting halide can be treated with nucleophiles such as substituted alcohols, phenols, amines, or thiols to afford the compound represented by Formula N. One well known procedure is the Gabriel reaction which introduces the amino group protected at the phthalimide (See March J. Advanced Organic Synthesis, John Wiley & Sons, Third Edition 1985).

There are many well established chemical procedures for the deprotection of the compounds described by Formula IV to the inventive compounds described by Formula I (Method B; see Scheme 2). For example if $P_1$ is a BOC protecting group, compounds described by Formula IV can be treated with an acidic substance such as dry hydrogen chloride in a solvent such as diethyl ether to furnish the compounds described by Formula I as the hydrochloride salt. If $P_1$ is a phthalimido protecting group, this can be removed in a two-step process by contacting compounds described by Formula IV with a reagent such as hydrazine in a warm solvent such as ethanol, followed by extraction of the free amine by standard procedures to afford the compounds of Formula I as free amino compounds. In general, the free amino compounds are converted to acid addition salts for ease of handling and for improved chemical stability. Examples of acid addition salts include but are not limited to hydrochloride, hydrobromide and methanesulfonate salts.

Scheme 2

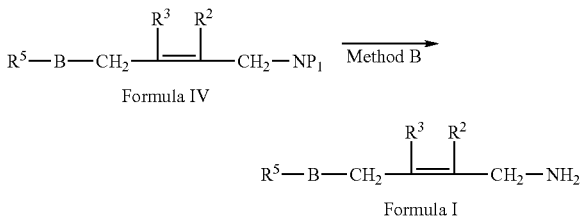

As readily recognized by those of skill in the art, numerous additional methods for the preparation of invention compounds can be employed by those of skill in the art of organic synthesis (see, for example, Scheme 3). Two additional exemplary procedures are described herein. In the first procedure, compounds described by Formula IV can be elaborated to the compounds Formula V wherein $R^5$ is aryl, heteroaryl, substituted aryl, substituted heteroaryl, cycloalkyl, cycloalkenyl, heterocyclyl (e.g., cycloheteroalkyl or cycloheteroalkenyl), aryl-$R^6$, heteroaryl-$R^6$, substituted aryl-$R^6$, substituted heteroaryl-$R^6$, alkylaryl, alkyheteroaryl, substituted alkylaryl, substituted alkylheteroaryl, alkylaryl-$R^6$, alkylheteroaryl-$R^6$, substituted alkylaryl-$R^6$, substituted alkylheteroaryl-$R^6$, alkenylaryl, alkenyheteroaryl, substituted alkenylaryl, substituted alkenylheteroaryl, alkenylaryl-$R^6$, alkenylheteroaryl-$R^6$, substituted alkenylaryl-$R^6$, substituted alkenylheteroaryl-$R^6$, alkynylaryl, alkynylheteroaryl, substituted alkynylaryl, substituted alkynylheteroaryl, alkynylaryl-$R^6$, alkynylheteroaryl-$R^6$, substituted alkynylaryl-$R^6$, or substituted alkynylheteroaryl-$R^6$.

Scheme 3

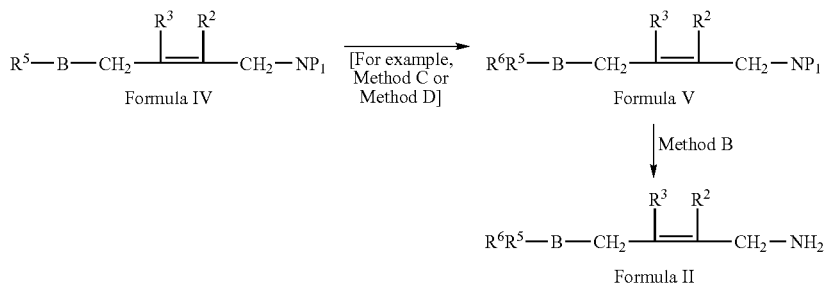

For example, phenolic compounds described by Formula V, such as Formula VI (see Scheme 4), can be converted through an alkylation reaction to compounds described by Formula VII.

Treatment of the phenolic compound Formula VI with Reagent 1 and a base, such as triethylamine, in a solvent such as THF for 30 min to 24 hours at temperatures from 4° C. to reflux temperature affords the nitrogen protected compound described by Formula VII (Method C; see Scheme 4). Deprotection to the primary amine can be achieved by one of the methods described above (Method B).

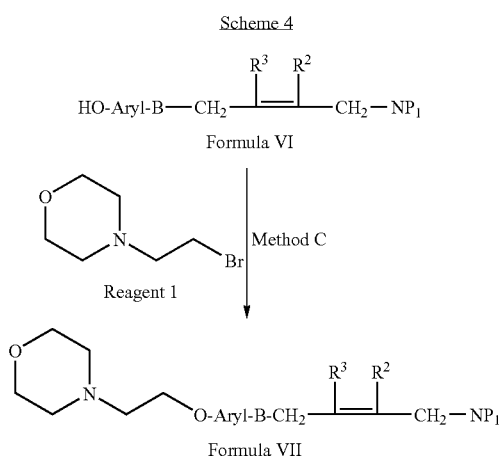

In another procedure, well known chemical synthetic methods can be applied for the elaboration of aryl bromides to compounds described by Formula IX (Method D; see Scheme 5). The benzylic bromide described by Formula VIII is contacted with the amino Reagent 2 in a solvent such as THF in the presence of a base, such as triethylamine, and at temperatures ranging from 4° C. to reflux temperature. The reaction is allowed to proceed from 30 min to 24 hours, then worked up by standard methods to yield the nitrogen protected compound described by Formula IX. Deprotection to the primary amine can be achieved by one of the methods described above (Method B).

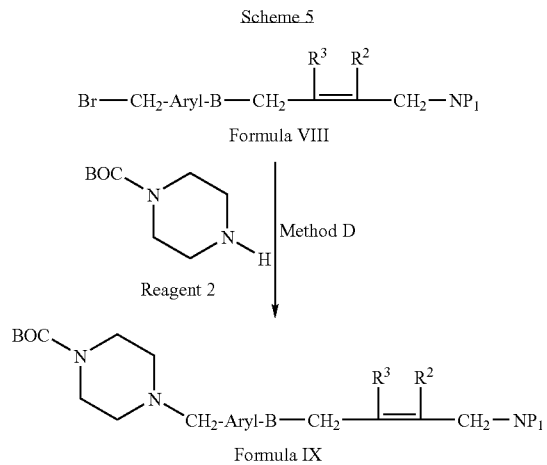

Compounds described by Formula V can be also prepared from compounds of Formula III by procedures in which $R^6R^5$ is introduced as a preformed functional entity; see Scheme 6 and Method A; these compounds can be deprotected to the primary amine by the Method B procedures described above to afford the compounds described by Formula 1. If B is oxygen, the preformed functional entities are generally phenol derivatives. Many such phenolic compounds are known in the chemical literature, while others can readily be synthesized by methods well known in the art of synthetic chemistry.

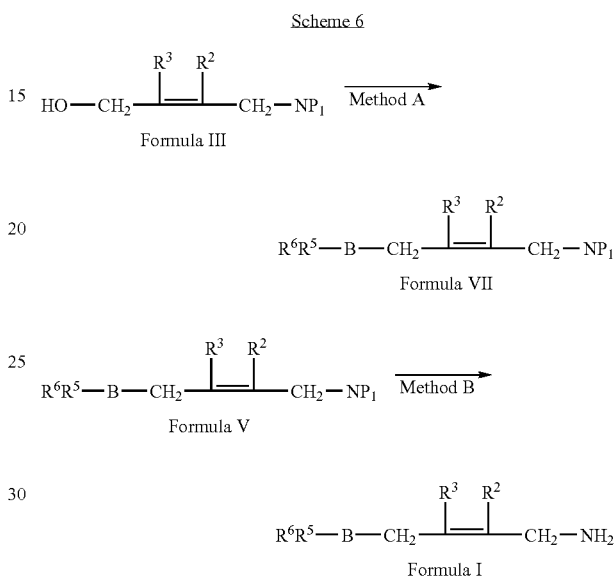

An example of how this can be accomplished is described by the reaction of Reagent 3 and the compounds described by Formula III to furnish the protected amino compounds described by Formula VII (see Scheme 7).

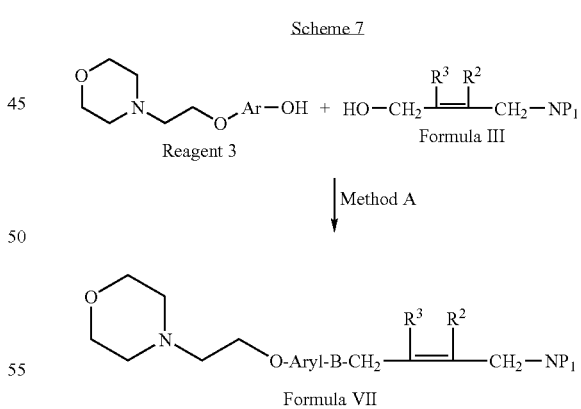

Reagent 3 can be readily prepared by methods in the art of organic synthesis. See, for example, Scheme 8, wherein the bromide Reagent 1 can be condensed with a mono-protected dihydroxyphenyl compound shown by Reagent 4 according to the Method C described above, followed by deprotection of Intermediate 1 to yield Reagent 3. The choice of deprotection methods will depend on the nature of the phenolic protecting group $P_2$.

Scheme 8

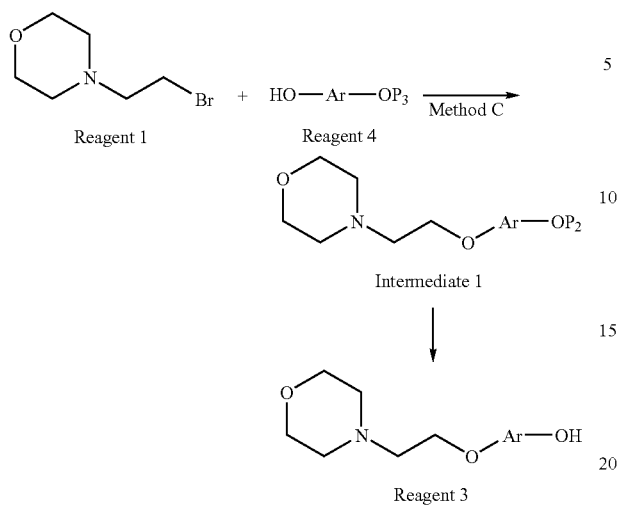

The synthesis of the starting material described by Formula III can be prepared by a Wittig-Emmons-Horner olefination reaction from the reaction of Reagent 4 with Reagent 5 (see Scheme 9). According to Method E, the Wittig-Emmons-Horner Reagent 5 is dissolved in a solvent such as THF, cooled to between −40° C. and 0° C., and then treated slowly with a strong base such as n-butyllithium in hexanes. When the anion derived from Reagent 5 was formed, a solution of the aldehyde Reagent 4 in a solvent such as THF is added quickly, then the reaction is allowed to proceed at ambient temperature for 4 to 24 hours. The reaction mixture is then quenched with water and the product Intermediate 2 is isolated in the normal way. The ester in Intermediate 1 can be reduced to the alcohol in Formula III by Method F, which is exemplary of many methods known in the art of organic synthesis suitable to accomplish such conversion. For example, diisobutylaluminum hydride in a solvent such as $CH_2Cl_2$ can be added to a cold (—40° C. to 0° C.) solution of Intermediate 1, then the reaction mixture is stirred for 1 to 24 hours and the product (described by Formula III) extracted and purified in the normal way.

Scheme 9

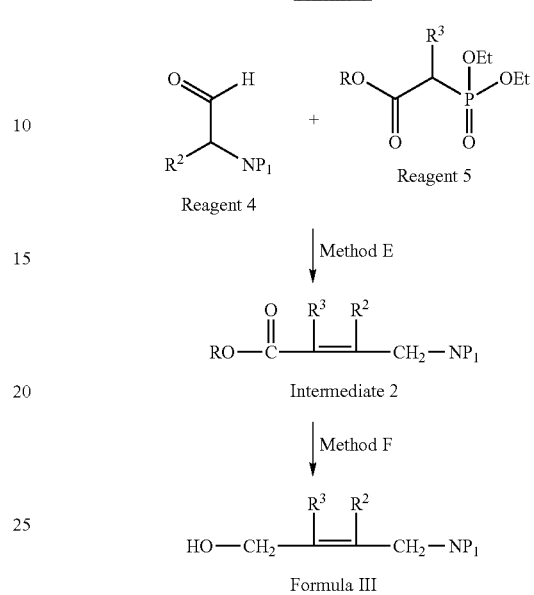

The present invention describes methods for the use of compounds described by Formula I to inhibit membrane-bound SSAO/VAP-1 and soluble SSAO/VAP-1. The relative inhibitory potencies of the compounds can be determined by the amount needed to inhibit the amine oxidase activity of SSAO/VAP-1 in a variety of ways, e.g., in an in vitro assay with recombinant human protein or with recombinant non-human enzyme, in cellular assays expressing normal rodent enzyme, in cellular assays which have been transfected with human protein, in in vivo tests in rodent and other mammalian species, and the like. The relative potencies of examples of compounds described by Formula I are listed in Table 1.

TABLE 1

SSAO/VAP-1 and MAO-B inhibitory activities of examples of inventive compounds and comparative compounds

| Name (Using the Cambridge Soft proprietary naming algorithm) | Mouse SSAO/VAP-1 Activity $IC_{50}$ (micromolar) | Human SSAO/VAP-1 Activity $IC_{50}$ (micromolar) | Human MAO-B Activity $IC_{50}$ (micromolar) |
|---|---|---|---|
| (Z)-3-Chloro-4-(3,5-difluorophenyl)but-2-en-1-amine hydrochloride | <1 | <10 | NT |
| (Z)-3-Chloro-5-phenylpent-2-en-1-amine hydrochloride | <10 | <10 | NT |
| (E)-3-Fluoro-4-phenoxybut-2-en-1-amine hydrochloride | <10 | <1 | <1 |
| (E)-4-(2,4-Dichlorophenoxy)-3-fluorobut-2-en-1-amine hydrochloride | <10 | <1 | <1 |
| (E)-3-Fluoro-4-(4-nitrophenoxy)but-2-en-1-amine hydrochloride | <10 | <1 | <1 |
| (E)-3-Fluoro-4-(3-(trifluoromethyl)phenoxy)but-2-en-1-amine hydrochloride | <100 | <1 | <1 |
| (E)-3-Fluoro-4-(4-(methylsulfonyl)phenoxy)but-2-en-1-amine hydrochloride | <1 | <1 | <100 |
| (E)-3-Fluoro-4-(4-(morpholinosulfonyl)phenoxy)but-2-en-1-amine hydrochloride | <10 | <1 | <10 |
| (E)-4-(4-Amino-2-fluorobut-2-enyloxy)-N,N-diisopropylbenzamide hydrochloride | <100 | <1 | <100 |

TABLE 1-continued

SSAO/VAP-1 and MAO-B inhibitory activities of examples of inventive compounds and comparative compounds

| Name (Using the Cambridge Soft proprietary naming algorithm) | Mouse SSAO/VAP-1 Activity $IC_{50}$ (micromolar) | Human SSAO/VAP-1 Activity $IC_{50}$ (micromolar) | Human MAO-B Activity $IC_{50}$ (micromolar) |
|---|---|---|---|
| (E)-4-(4-Amino-2-fluorobut-2-enyloxy)-N-benzylbenzamide hydrochloride | <1 | <1 | <1 |
| (E)-4-(4-Amino-2-fluorobut-2-enyloxy)-N-cyclohexylbenzamide hydrochloride | <1 | <1 | <1 |
| (E)-3-Fluoro-4-(2-methylbenzo[d]thiazol-5-yloxy)but-2-en-1-amine hydrochloride | <1 | <1 | <100 |
| (S,E)-4-(4-Amino-2-fluorobut-2-enyloxy)-N-(1-phenylethyl)benzenesulfonamide hydrochloride | <1 | <1 | <1 |
| Mofegiline | 1 nM | 21 nM | 4 nM |

In another embodiment of the present invention, there are provided compositions comprising a compound having Formula I and at least one pharmaceutically acceptable excipient, carrier or diluent therefor.

The phrase "pharmaceutically acceptable carrier" refers to any carrier known to those skilled in the art to be suitable for the particular mode of administration. In addition, the compounds may be formulated as the sole pharmaceutically active ingredient in the composition or may be combined with other active ingredients.

Compositions herein comprise one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel *Introduction to Pharmaceutical Dosage Forms, Fourth Edition* 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders to be treated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in PCT publication WO 04/018997, and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art.

In one embodiment, a therapeutically effective dosage should produce a serum concentration of active ingredient of from about 0.1 ng/mL to about 50-100 µg/mL. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, dissolution in aqueous sodium bicarbonate, formulating the compounds of interest as nanoparticles, and the like. Derivatives of the compounds, such as salts, solvates, prodrugs, and the like, of invention compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof The pharmaceutically therapeutically active compounds and derivatives thereof (e.g., salts, solvates, or prodrugs thereof, and the like) are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% (wt %) with the balance made up from non-toxic carrier may be prepared. Methods for preparation of these compositions are known to those skilled in the art. The contemplated compositions may contain 0.001%-100% (wt %) active ingredient, in one embodiment 0.1-95% (wt %), in another embodiment 75-85% (wt %).

A. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

1. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

B. Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

C. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

D. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% (vol %) isotonic solutions, pH about 5-7, with appropriate salts.

E. Compositions for other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point.

Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

F. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The present invention also discloses methods to use the compounds described by Formula I to inhibit SSAO/VAP-1 in patients suffering from an inflammatory disease, and methods to treat inflammatory diseases. Human inflammatory diseases include inflammation associated with liver disease, arthritis, Crohn's disease, irritable bowel disease, psoriasis, inflammation associated with respiratory disease (e.g., asthma, bronchitis, chronic pulmonary obstructive disease, bronchiectasis, and the like), artherosclerosis, inflammation due to diabetes, inflammation associated with ocular disease, and tissue destruction by inflammatory cells following stroke.

Thus, in one aspect, the present invention is directed to methods of inhibiting an amine oxidase enzyme in a subject in need thereof, said methods comprising administering to said subject an effective amount of a compound of Formula Ito effect a positive therapeutic response.

In another aspect, the present invention is directed to methods of treating a disease associated with an amine oxidase enzyme, said methods comprising administering to a subject in need thereof a therapeutically effective amount of a compound of Formula I.

In still another aspect, the present invention is directed to methods of treating a disease modulated by SSAO/VAP-1 and/or MAO, said methods comprising administering to a subject in need thereof a therapeutically effective amount of a compound of Formula I.

The above-described methods are applicable wherein the disease is inflammation. As employed herein, "inflammation" embraces a wide variety of indications, including arthritis (including juvenile rheumatoid arthritis), Crohn's disease, ulcerative colitis, inflammatory bowel diseases (e.g., irritable bowel disease), psoriasis, inflammation associated with respiratory disease (e.g., asthma, pulmonary inflammation, chronic pulmonary obstructive disease, bronchitis, bronchiectasis, and the like), skin inflammation, ocular disease (e.g., uveitis), contact dermatitis, liver inflammation, liver autoimmune diseases, autoimmune hepatitis, primary biliary cirrhosis, sclerosing cholangitis, autoimmune cholangitis, alcoholic liver disease, artherosclerosis, chronic heart failure, congestive heart failure, ischemic diseases, stroke and complications thereof, myocardial infarction and complications thereof, tissue destruction by inflammatory cells following stroke, synovitis, systemic inflammatory response syndrome, sepsis, and the like.

A particular form of inflammation which is beneficially treated employing invention compounds is ocular disease, especially inflammation of the eye, including uveitis, iritis, retinitis, autoimmune eye inflammation, inflammation driven angiogenesis and lymphogenesis, macular degeneration, and the like.

The above-described methods are also applicable wherein the disease is Type I diabetes and complications thereof, Type II diabetes and complications thereof, metabolic syndrome, organ and/or tissue transplant rejection, and the like.

The above-described methods are also applicable wherein the disease is a neuroinflammatory disease. As employed herein, "neuroinflammatory diseases" embrace a variety of indications, including stroke, Parkinson's disease, Alzheimer's disease, vascular dimentia, multiple sclerosis, chronic multiple sclerosis, and the like.

The above-described methods are also applicable wherein the disease is a psychiatric disorder. As employed herein, "psychiatric disorder" embraces a wide variety of indications, including major depression, bipolar depression, attention deficit hyperactivity disorder, and the like.

The invention will now be described in greater detail with reference to the following non-limiting examples.

EXAMPLE 1

Preparation of
(E)-3-fluoro-4-phenoxybut-2-en-1-amine
hydrochloride

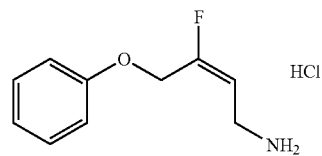 [SMILES: NC/C=C(/F)COc1ccccc1 ; Cl]

Preparation of (E)-ethyl 4-(tert-butoxycarbonylamino)-2-fluorobut-2-enoate

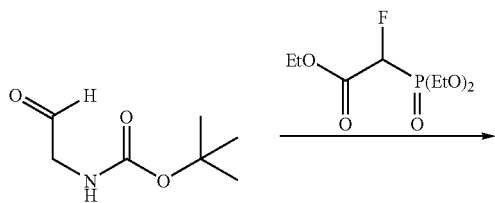

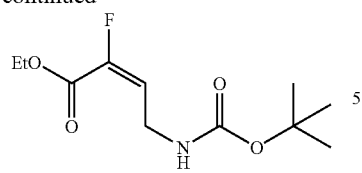

To a stirred solution of triethyl 2-fluoro-2-phosphonoacetate (0.61 mL, 3 mmol) in dry THF (40 mL) at −10° C. under nitrogen was added n-butyllithium (2.5 M solution in hexanes; 1.16 mL, 2.9 mmol) dropwise. The contents of the vessel were allowed to stir for 5 mins at −10° C. before addition of N-Boc-aminoacetaldehyde (0.378 g, 2.5 mmol, in 5 mL THF). The reaction mixture was then allowed to warm to room temperature and stirred for 16 hours. Water (50 mL) was added to the mixture and the organic layer extracted with diethyl ether (50 mL) and washed with brine (20 mL), dried over MgSO$_4$, filtered and the solvent removed under reduced pressure to afford the crude product as a clear oil (0.850 g). Purification by flash chromatography (silica, ~4 g) eluting in 5-15% EtOAc in n-hexane afforded (E)-ethyl 4-(tert-butoxycarbonylamino)-2-fluorobut-2-enoate (0.525 g, 85%) as a clear oil and a mixture of 10:1 E:Z; E(major)-isomer $^1$H-NMR (200 MHz, CDCl$_3$): δppm: 1.36 (3H, t, J 7.0 Hz), 1.45 (9H, s), 4.17 (2H, m), 4.32 (2H, q, J 7.0 Hz), 4.88 (1H, br s), 6.01 (1H, dt, J 19.5, 7.2).

Preparation of (E)-tertbutyl 3-fluoro-4-hydroxybut-2-enylcarbamate

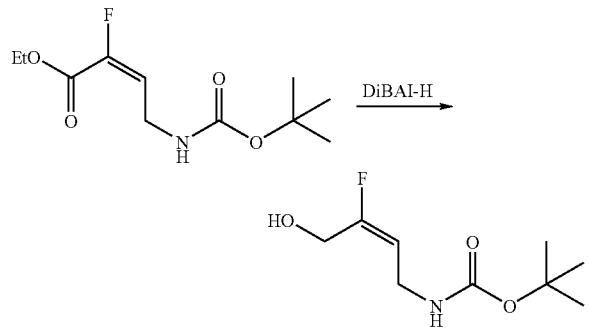

To a stirring, cold (−10° C.) solution of ethyl 4-(tert-butoxycarbonylamino)-2-fluorobut-2-enoate (a 10:1 mixture of E/Z isomers; 6.33 g, 25.6 mmol) in CH$_2$Cl$_2$ (200 mL) under Ar was added dropwise Diisobutylaluminium hydride solution (1M solution in hexanes, 70.5 mL, 70.49 mmol). After addition was complete the reaction was left to stir at this temperature for a further 2 h. The reaction was then quenched carefully by dropwise addition of cold water. The resulting slurry was poured into a flask containing a saturated aqueous solution of sodium potassium tartrate (400 mL) and the biphasic mixture was stirred vigorously for 2 h. After transferring the mixture to a separatory funnel the aqueous phase was extracted with CH$_2$Cl$_2$ (3×100 mL). The combined organics were washed with brine (100 mL), dried over anhydrous MgSO$_4$ and concentrated in vacuo to give tert-butyl-3-fluoro-4-hydroxybut-2-enylcarbamate as a 10:1 mixture of E/Z isomers. Purification and separation of the desired E isomer was performed using silica gel chromatography eluting with 30% ethyl acetate in hexanes affording (E)-tert butyl-3-fluoro-4-hydroxybut-2-enylcarbamate (4.25 g, 20.7 mmol, 81%) as a colourless oil that solidified upon cooling, $^1$H-NMR (200 MHz, CDCl$_3$): δppm: 1.43 (9H, s), 3.72 (2H, dd, J 7.5, 5.4 Hz), 4.25 (2H, d, J 21.5 Hz), 4.85 (1H, br s), 5.18 (1H, dt, 19.2, 8.5 Hz).

Preparation of (Z)-tert-butyl 3-fluoro-4-hydroxybut-2-enylcarbamate

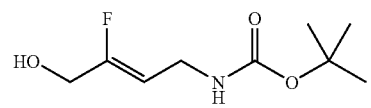

This compound was isolated in a small quantity when purifying the E-isomer; clear oil, $^1$H-NMR (200 MHz, CDCl$_3$): δppm: 1.45 (9H, s), 3.83 (2H, t, J 6.1 Hz), 4.12 (2H, d, J 13.7 Hz), 4.67 (1H, br s), 5.03 (1H, dt, J 35.6, 7.0 Hz).

Procedure A: Preparation of (E)-tert-butyl 3-fluoro-4-phenoxybut-2-enylcarbamate

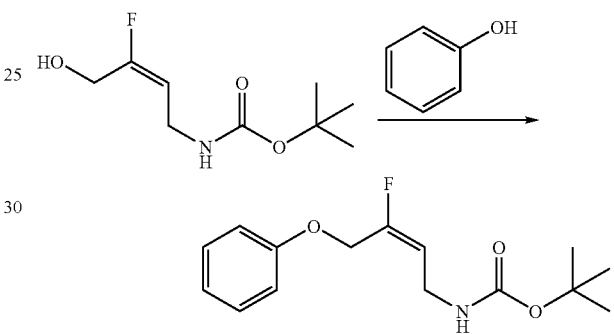

To a stirred solution of (E)-tert-butyl 3-fluoro-4-hydroxybut-2-enylcarbamate (0.044 g, 0.21 mmol), triphenylphosphine (0.079 g, 0.3 mmol) and phenol (0.028 g, 0.3 mmol) in dry THF (2 mL) at 0° C. under nitrogen was added diisopropyl azodicarboxylate (59 μL, 0.3 mmol) dropwise. The reaction mixture was allowed to warm to room temperature and stirred for 16 hours. Silica (~1 g) was then added to the reaction mixture and the solvent removed under reduced pressure. The resultant solid was purified by flash chromatography eluting in 15% EtOAc in n-hexane to afford a 1:1 mixture of the title compound: phenol (0.036 g). This mixture was taken up into diethyl ether (10 mL), washed with 2 M NaOH solution (5 mL) and brine (5 mL), dried over MgSO$_4$, filtered and the solvent removed under reduced pressure to afford (E)-tert-butyl 3-fluoro-4-phenoxybut-2-enylcarbamate (0.026 g, 43%) as a clear oil; $^1$H-NMR (200 MHz, CDCl$_3$): δppm: 1.43 (9H, s), 3.78 (2H, t, J 7.2 Hz), 4.53 (1H, br s), 4.68 (2H, d, J 19.0 Hz), 5.43 (1H, dt, J 18.8, 8.3 Hz), 6.61-6.79 (3H, m), 7.17-7.31 (2H, m).

Procedure B: Preparation of (E)-3-fluoro-4-phenoxybut-2-en-1-amine hydrochloride

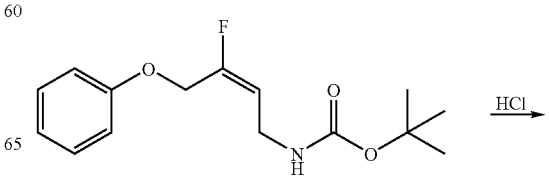

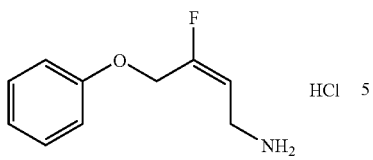

To a solution of (E)-tert-butyl 3-fluoro-4-phenoxybut-2-enylcarbamate (0.026 g, 0.09 mmol) in diethyl ether (3 mL) was added HCl (2 M solution in diethyl ether; 0.23 mL) dropwise. The reaction mixture was then sealed and allowed to stand for 68 hours. The solvent was removed under reduced pressure, dissolved in methanol (2 mL), filtered, and the methanol removed. The resultant gum was dried at 60° C. to afford (E)-3-fluoro-4-phenoxybut-2-en-1-amine hydrochloride (0.009 g, 46%) as an off-white solid; m.p.=113-116° C.; $^1$H-NMR (200 MHz, CD$_3$OD): δppm: 3.69 (2H, d, J 8.2 Hz), 4.75 (2H, d, J 17.8 Hz), 5.51 (1H, dt, J 18.2, 8.6 Hz), 6.91-7.03 (3H, m), 7.22-7.35 (2H, m).

EXAMPLE 2

The following compounds were prepared according to procedures A and B described above:

(E)-3-Fluoro-4-(4-(trifluoromethyl)phenoxy)but-2-en-1-amine hydrochloride was synthesized from (E)-tert-butyl 3-fluoro-4-hydroxybut-2-enylcarbamate and 4-trifluoromethylphenol.

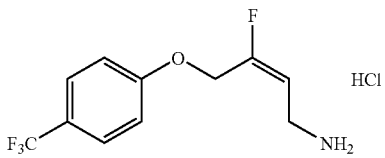 [SMILES: NC/C=C(/F)COc1ccc(C(F)(F)F)cc1 ; Cl]

The product was obtained as an off-white solid; m.p.=58-62° C.; $^1$H-NMR (200 MHz, CD$_3$OD): δppm: 3.71 (2H, d, J 7.7 Hz), 4.85 (2H, d, 18.1 Hz), 5.54 (1H, dt, J 18.4, 8.3), 7.13 (2H, d, J 9.0 Hz), 7.61 (2H, d, J 8.7 Hz).

(E)-4-(2,4-Dichlorophenoxy)-3-fluorobut-2-en-1-amine hydrochloride was synthesized from (E)-tert-butyl 3-fluoro-4-hydroxybut-2-enylcarbamate and 2,4-dichlorophenol.

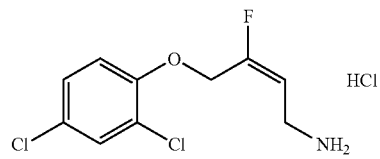 [SMILES: NC/C=C(/F)COc1ccc(Cl)cc1Cl ; Cl]

The product was obtained as a light brown solid; m.p.=134-137° C.; $^1$H-NMR (200 MHz, CD$_3$OD): δppm: 3.77 (2H, d, J 8.6 Hz), 4.86 (2H, d, J 16.1 Hz), 5.55 (1H, dt, J 18.4, 8.6 Hz), 7.13 (1H, d, J 8.9 Hz), 7.26-7.34 (1H, m), 7.45 (1H, m).

(E)-3-Fluoro-4-(4-methoxyphenoxy)but-2-en-1-amine hydrochloride was synthesized from (E)-tert-butyl 3-fluoro-4-hydroxybut-2-enylcarbamate and 4-methoxyphenol.

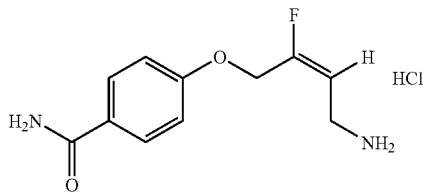 [SMILES: NC/C=C(/F)COc1ccc(C(N)=O)cc1 ; Cl]

The product was obtained as a dark solid; m.p.=89-92° C.; $^1$H-NMR (200 MHz, CD$_3$OD): δppm: 3.67 (2H, d, J 7.9 Hz), 3.71 (3H, s), 4.69 (2H, d, J 17.5 Hz), 5.47 (1H, dt, J 18.4, 8.3 Hz), 6.78-6.85 (4H, m).

(E)-4-(4-Amino-2-fluorobut-2-enyloxy)benzamide hydrochloride was synthesized from (E)-tert-butyl 3-fluoro-4-hydroxybut-2-enylcarbamate and 4-hydroxybenzamide.

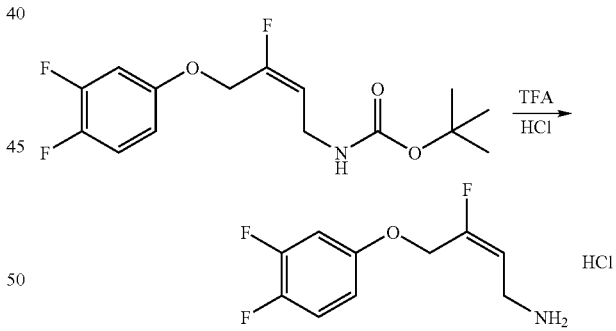

The product was obtained as a grey solid contaminated with ~10% of the phenol precursor; m.p. (<90% pure)=138-145° C.; $^1$H-NMR (200 MHz, D$_2$O): δppm: 3.76 (2H, d, J 8.3 Hz), 4.88 (2H, d, J 19.1 Hz), 5.64 (1H, dt, J 18.8, 7.8 Hz), 7.09 (2H, d, J 8.6 Hz), 7.81 (2H, d, J 8.7 Hz).

EXAMPLE 3

Procedure C: Preparation of (E)-4-(3,4-difluorophenoxy)-3-fluorobut-2-en-1-amine hydrochloride To a stirred solution of (E)-tert-butyl 4-(3,4-difluorophenoxy)-3-fluorobut-2-enylcarbamate (0.061 g, 0.19 mmol [synthesized from (E)-tert-butyl 3-fluoro-4-hydroxybut-2-enylcarbamate and 3,4-difluorophenol following procedure F]) in CH$_2$Cl$_2$ (4.5 mL) at room temperature was added trifluoroacetic acid (0.5 mL). The reaction mixture was allowed to stir for 2 h until no further starting material remained by thin layer chromatography analysis. The solvent was then removed under reduced pressure and the residue taken up in diethyl ether (20 mL) and water (30 mL), and the pH adjusted to ~pH 1 by addition of 0.1 M HCl (aq.). The aqueous layer was extracted with a further portion of diethyl ether (10 mL) before addition of 2 M NaOH solution to bring the pH up to ~pH 12. The alkaline layer was extracted with diethyl ether (2×20 mL) and the organics combined and washed with brine (10 mL), dried over MgSO₄, filtered and solvent removed under reduced pressure to afford the amine as a clear oil (0.061 g). This product was dissolved in diethyl ether and treated dropwise with HCl (2 M solution in diethyl ether; 0.4 mL) which resulted in the formation of a colorless precipitate. After standing for 20 minutes the precipitate was filtered, washed with diethyl ether (2×2 mL) and dried under vacuum to yield (E)-4-(3,4-difluorophenoxy)-3-fluorobut-2-en-1-amine hydrochloride (0.030 g, 62%) as a fine colorless powder; m.p.=139-140° C.; ¹H-NMR (200 MHz, CD₃OD): δppm: 3.70 (2H, d, J 7.4 Hz), 4.76 (2H, d, J 18.2 Hz), 5.54 (1H, dt, J 18.1, 8.3 Hz), 6.74-6.83 (1H, m), 6.90-7.01 (1H, m), 7.20 (1H, q, J 19.2).

EXAMPLE 4

The following compounds were prepared according to procedures A and C described above.

(E)-3-Fluoro-4-(4-nitrophenoxy)but-2-en-1-amine hydrochloride was synthesized from (E)-tert-butyl 3-fluoro-4-hydroxybut-2-enylcarbamate and 4-nitrophenol.

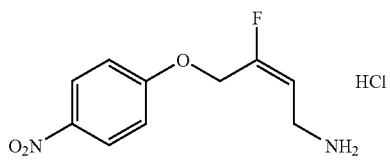 [SMILES: NC/C=C(/F)COc1ccc([N+](=O)[O-])cc1 ; Cl]

The product was obtained as a fine colorless powder; m.p.=226-227° C.; ¹H-NMR (200 MHz, CD₃OD): δppm: 3.74 (2H, d, J 8.6 Hz), 4.93 (2H, d, J 18.8 Hz), 5.58 (1H, dt, J 18.1, 8.2 Hz), 7.15 (2H, d, J 9.2 Hz), 8.25 (2H, d, J 9.3 Hz).

(E)-4-(4-tert-Butylphenoxy)-3-fluorobut-2-en-1-amine hydrochloride was synthesized from (E)-tert-butyl 3-fluoro-4-hydroxybut-2-enylcarbamate and 4-tert-butylphenol.

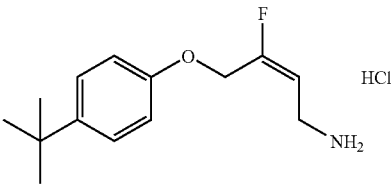 [SMILES: CC(C)(C)c1ccc(OC/C(F)=C\CN)cc1 ; Cl]

The product was obtained as colorless flakes; m.p.=128-130° C.; ¹H-NMR (200 MHz, CD₃OD): δppm: 1.28 (9H, s), 3.70 (2H, d, J 8.4 Hz), 4.75 (2H, d, J 17.5 Hz), 5.54 (1H, dt, J 18.5, 8.4 Hz), 6.90 (2H, d, J 8.5 Hz), 7.33 (2H, d, J 8.7 Hz).

(Z)-3-Fluoro-4-(4-(trifluoromethyl)phenoxy)but-2-en-1-amine hydrochloride was synthesized from (Z)-tert-butyl 3-fluoro-4-hydroxybut-2-enylcarbamate and 4-trifluoromethylphenol.

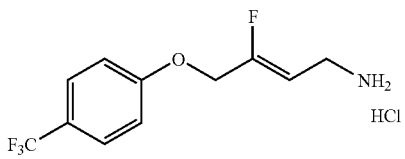 [SMILES: NC/C=C(\F)COc1ccc(C(F)(F)F)cc1 ; Cl]

The product was obtained as a fine colorless powder; m.p.=135-138° C.; ¹H-NMR (200 MHz, CD₃OD): δppm: 3.69 (2H, d, J 6.9 Hz), 4.77 (2H, d, J 12.5 Hz), 5.37 (1H, dt, J 33.5, 6.3 Hz), 7.13 (2H, d, J 7.0 Hz), 7.61 (2H, d, J 6.5 Hz).

(E)-3-Fluoro-4-(3-(trifluoromethyl)phenoxy)but-2-en-1-amine hydrochloride was synthesized from (E)-tert-butyl 3-fluoro-4-hydroxybut-2-enylcarbamate and 3-trifluoromethylphenol.

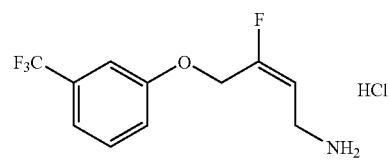 [SMILES: NC/C=C(/F)COc1cccc(C(F)(F)F)c1 ; Cl]

The product was obtained as fluffy colorless needles; m.p.=104-106° C.; ¹H-NMR (200 MHz, CD₃OD): δppm: 3.72 (2H, d, J 8.3 Hz), 4.85 (2H, d, J 18.4 Hz), 5.55 (1H, dt, J 18.2, 8.2 Hz), 7.20-7.35 (3H, m), 7.43-7.59 (1H, m).

(E)-Methyl 4-(4-amino-2-fluorobut-2-enyloxy)benzoate hydrochloride was synthesized from (E)-tert-butyl 3-fluoro-4-hydroxybut-2-enylcarbamate and methyl 4-hydroxybenzoate.

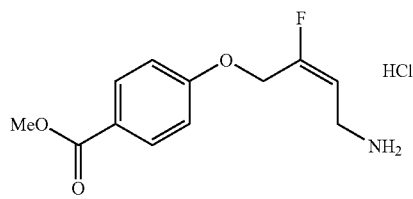 [SMILES: COC(=O)c1ccc(OC/C(F)=C\CN)cc1 ; Cl]

The product was obtained as a fine colorless powder; m.p.=139-140° C.; ¹H-NMR (200 MHz, CD₃OD): δppm: 3.73 (2H, d, J 8.1 Hz), 3.86 (3H, s), 4.85 (2H, d, J 18.1 Hz), 5.55 (1H, dt, J 18.2, 8.3 Hz), 7.05 (2H, d, J 9.0 Hz), 7.98 (2H, d, J 9.0 Hz).

(E)-3-Fluoro-4-(4-fluorophenoxy)but-2-en-1-amine hydrochloride was synthesized from (E)-tert-butyl 3-fluoro-4-hydroxybut-2-enylcarbamate and 4-fluorophenol.

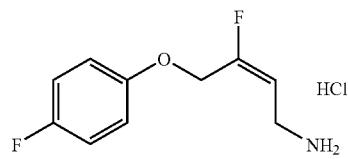 [SMILES: NC/C=C(/F)COc1ccc(F)cc1 ; Cl]

The product was obtained as a fine colorless powder; m.p.=133-134° C.; ¹H-NMR (200 MHz, CD₃OD): δppm: 3.69 (2H, d, J 8.3 Hz), 4.74 (2H, d, J 17.7 Hz), 5.50 (1H, dt, J 18.3, 8.3 Hz), 6.92-7.09 (4H, m).

(E)-3-Fluoro-4-(4-(methylsulfonyl)phenoxy)but-2-en-1-amine hydrochloride was synthesized from (E)-tert-butyl 3-fluoro-4-hydroxybut-2-enylcarbamate and 4-methylsulfonylphenol.

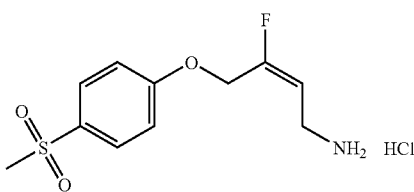 [SMILES: CS(=O)(=O)c1ccc(OC/C(F)=C\CN)cc1 ; Cl]

The product was obtained as an off-white solid; m.p.=196-198° C.; $^1$H-NMR (400 MHz, CD$_3$OD): δppm: 3.11 (3H, s), 3.76 (2H, d, J 8.2 Hz), 4.93 (2H, d, J 18.2 Hz), 5.55 (1H, dt, J 18.2, 8.2 Hz), 7.23 (2H, d, J 9.2 Hz), 7.94 (2H, d, J 9.2 Hz).

(E)-3-Fluoro-4-(4-(morpholinosulfonyl)phenoxy)but-2-en-1-amine hydrochloride was synthesized from (E)-tert-butyl 3-fluoro-4-hydroxybut-2-enylcarbamate and 4-(morpholinosulfonyl)phenol.

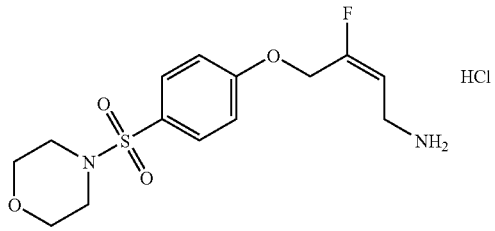 [SMILES: NC/C=C(/F)COc1ccc(S(=O)(=O)N2CCOCC2)cc1 ; Cl]

The product was obtained as a white solid; m.p.=83-85° C.; $^1$H-NMR (200 MHz, CDCl$_3$): δppm: 2.98 (4H, t, J 5.0 Hz), 3.40 (2H, d, J 7.8 Hz), 3.74 (4H, t, J 5.0 Hz), 4.72 (2H, d, J 19.4 Hz), 5.58 (1H, dt, J 19.4, 7.8 Hz), 7.06 (2H, d, J 8.8 Hz), 7.71 (2H, d, J 8.8 Hz).

(E)-4-(4-Amino-2-fluorobut-2-enyloxy)-N,N-diisopropylbenzamide hydrochloride was synthesized from (E)-tert-butyl 3-fluoro-4-hydroxybut-2-enylcarbamate and 4-hydroxy-N,N-diisopropylbenzamide.

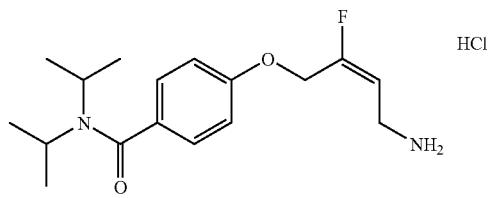 [SMILES: CC(C)N(C(=O)c1ccc(OC/C(F)=C\CN)cc1)C(C)C ; Cl]

The product was obtained as a yellow gum; $^1$H-NMR (400 MHz, CD$_3$OD): δppm: 1.09-1.72 (6H, br.s), 3.70-3.80 (2H, br.s), 3.72 (2H, d, J 8.4 Hz), 4.85 (2H, d, obscured by H$_2$O peak), 5.55 (1H, dt, J 18.4, 8.4 Hz), 7.09 (2H, d, J 8.9 Hz), 7.33 (2H, d, J 8.8 Hz).

(E)-4-(4-Amino-2-fluorobut-2-enyloxy)-N-benzylbenzamide hydrochloride was synthesized from (E)-tert-butyl 3-fluoro-4-hydroxybut-2-enylcarbamate and N-benzyl-4-hydroxybenzamide.

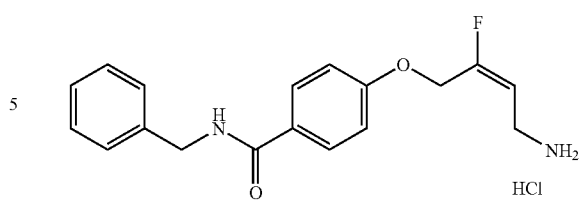

The product was obtained as a white solid; m.p.=189-191° C.; $^1$H-NMR (400 MHz, CD$_3$OD): δppm: 3.74 (2H, d, J 8.2 Hz), 4.56 (2H, s), 4.86 (2H, d, obscured by H$_2$O peak), 5.56 (1H, dt, J 18.2, 8.3 Hz), 7.08 (2H, d, J 8.8 Hz), 7.19-38 (5H, m), 7.82 (2H, d, J 8.8 Hz).

(Z)-3-Fluoro-4-phenoxybut-2-en-1-amine hydrochloride was synthesized from (Z)-tert-butyl 3-fluoro-4-hydroxybut-2-enylcarbamate and phenol.

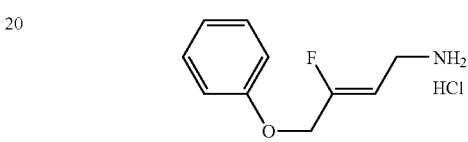

The product was obtained as a white powder; m.p.=155-157° C.; $^1$H-NMR (200 MHz, CD$_3$OD): δppm: 3.67 (2H, d, J 8.4 Hz), 4.65 (2H, d, J 12.0 Hz), 5.32 (1H, dt, J 34.0, 7.0 Hz), 6.97 (3H, m), 7.28 (2H, m).

(Z)-4-(2,4-Dichlorophenoxy)-3-fluorobut-2-en-1-amine hydrochloride was synthesized from (Z)-tert-butyl 3-fluoro-4-hydroxybut-2-enylcarbamate and 2,4-dichlorophenol.

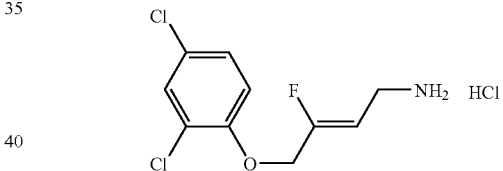

The product was obtained as a white powder; m.p.=164-166° C.; $^1$H-NMR (200 MHz, CD$_3$OD): δppm: 3.68 (2H, d, J 7.4 Hz), 4.73 (2H, d, J 12.0 Hz), 5.39 (1H, dt, J 33.6, 7.0 Hz), 7.11 (1H, d, J 9.0 Hz), 7.27 (1H, dd, J 2.8, 9.0 Hz), 7.42 (1H, d, J 2.8 Hz).

(E)-4-(3-Chloro-4-fluorophenoxy)-3-fluorobut-2-en-1-amine hydrochloride was synthesized from (E)-tert-butyl 3-fluoro-4-hydroxybut-2-enylcarbamate and 3-chloro-4-fluorophenol.

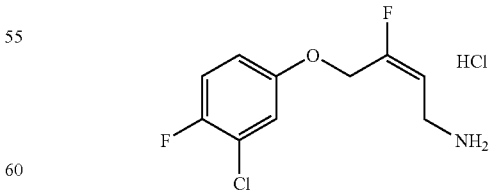

The product was obtained as a white powder; m.p.=144-145° C.; $^1$H-NMR (200 MHz, CD$_3$OD): δppm: 3.70 (2H, d, J 8.3 Hz), 4.77 (2H, d, J 18.5 Hz), 5.53 (1H, dt, J 18.2, 8.3 Hz), 6.95 (1H, dt, J 9.3, 3.2 Hz), 7.14 (1H, d, J 8.1 Hz), 7.15 (1H, q, J 28.3 Hz).

(E)-3-Fluoro-4-(4-phenoxyphenoxy)but-2-en-1-amine hydrochloride was synthesized from (E)-tert-butyl 3-fluoro-4-hydroxybut-2-enylcarbamate and 4-phenoxyphenol.

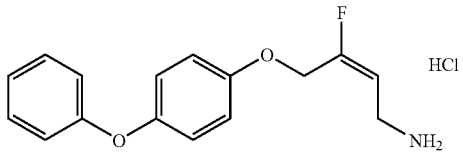 [SMILES: NC/C=C(/F)COc1ccc(Oc2ccccc2)cc1 ; Cl]

The product was obtained as a white powder; m.p.=118-120° C.; ¹H-NMR (200 MHz, CD$_3$OD): δppm: 3.71 (2H, d, J 7.2 Hz), 4.76 (2H, d, J 17.8 Hz), 5.51 (1H, dt, J 18.4, 8.2 Hz), 6.98-7.34 (9H, m).

(E)-4-(4-Amino-2-fluorobut-2-enyloxy)benzonitrile hydrochloride was synthesized from (E)-tert-butyl 3-fluoro-4-hydroxybut-2-enylcarbamate and 4-cyanophenol.

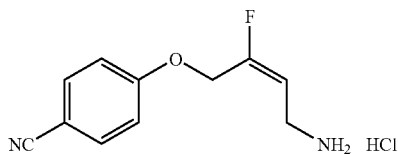

The product was obtained as an off-white powder; m.p.=240-243° C.; ¹H-NMR (200 MHz, CD$_3$OD): δppm: 3.73 (2H, d, J 7.6 Hz), 4.88 (2H, d, J 18.4 Hz), 5.56 (1H, dt, J 17.6, 8.8 Hz), 7.13 (2H, d, J 8.8 Hz), 7.70 (2H, d, J 8.8 Hz).

(E)-4-(4-Amino-2-fluorobut-2-enyloxy)-2-fluorobenzonitrile hydrochloride was synthesized from (E)-tert-butyl 3-fluoro-4-hydroxybut-2-enylcarbamate and 3-fluoro-4-cyanophenol.

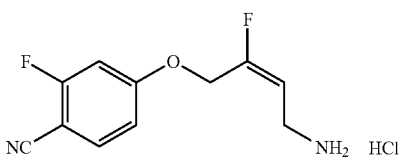

The product was obtained as an off-white powder; m.p.=228-230° C.; ¹H-NMR (200 MHz, CD$_3$OD): δppm: 3.72 (2H, d, J 8.4 Hz), 4.89 (2H, d, J 18.8 Hz), 5.58 (1H, dt, J 18.0, 8.2 Hz), 6.99 (2H, m), 7.70 (1H, m).

(E)-4-(Benzo[d][1,3]dioxol-5-yloxy)-3-fluorobut-2-en-1-amine hydrochloride was synthesized from (E)-tert-butyl 3-fluoro-4-hydroxybut-2-enylcarbamate and sesamol.

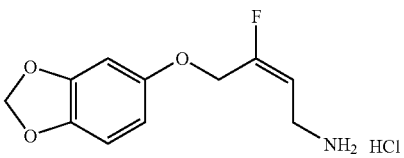 [SMILES: NC/C=C(/F)COc1ccc2c(c1)OCO2 ; Cl]

The product was obtained as an off-white powder; m.p.=0.98-100° C.; ¹H-NMR (200 MHz, CD$_3$OD): δppm: 3.68 (2H, d, J 8.2 Hz), 4.69 (2H, d, J 17.8 Hz), 5.49 (1H, dt, J 18.4, 8.4 Hz), 5.90 (2H, s), 6.42 (1H, dd, J 2.6, 8.8 Hz), 6.57 (1H, d, J 2.6 Hz), 6.72 (1H, d, J 8.8 Hz).

(E)-3-Fluoro-4-(naphthalen-2-yloxy)but-2-en-1-amine hydrochloride was synthesized from (E)-tert-butyl 3-fluoro-4-hydroxybut-2-enylcarbamate and 2-naphthol.

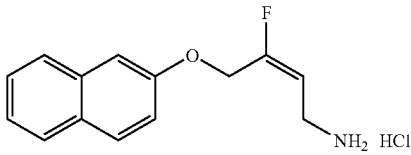 [SMILES: NC/C=C(/F)COc1ccc2ccccc2c1 ; Cl]

The product was obtained as an off-white powder; m.p.=191-193° C.; ¹H-NMR (200 MHz, CD$_3$OD): δppm: 3.75 (2H, d; J 8.2 Hz), 4.90 (2H, d, J 17.4 Hz), 5.55 (1H, dt, J 18.4, 8.2 Hz), 7.17 (1H, dd, J 2.6, 9.4 Hz), 7.39 (3H, m), 7.77 (3H, m).

(E)-(4-(4-Amino-2-fluorobut-2-enyloxy)phenyl)(phenyl)methanone hydrochloride was synthesized from (E)-tert-butyl 3-fluoro-4-hydroxybut-2-enylcarbamate and 4-benzoylphenol.

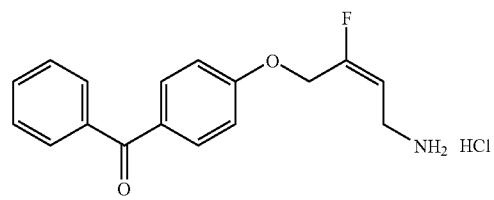 [SMILES: NC/C=C(/F)COc1ccc(C(=O)c2ccccc2)cc1 ; Cl]

The product was obtained as an off-white powder; m.p.=165-167° C.; ¹H-NMR (200 MHz, CD$_3$OD): δppm: 3.71 (2H, d, J 8.2 Hz), 4.56 (2H, d, J 18.2 Hz), 5.57 (1H, dt, J 18.2, 8.2 Hz), 7.09 (2H, d, J 9.0 Hz), 7.59 (5H, m), 7.79 (2H, d, J 9.0 Hz).

(E)-4-(2-Chloro-4-nitrophenoxy)-3-fluorobut-2-en-1-amine hydrochloride was synthesized from (E)-tert-butyl 3-fluoro-4-hydroxybut-2-enylcarbamate and 2-chloro-4-nitrophenol.

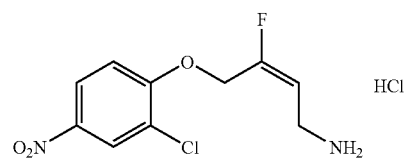 [SMILES: NC/C=C(/F)COc1ccc([N+](=O)[O-])cc1Cl ; Cl]

The product was obtained as a fine white powder; m.p.=204-205° C.; ¹H-NMR (200 MHz, CD$_3$OD): δppm: 3.81 (2H, d, J 7.9 Hz), 5.04 (2H, d, J 16.8 Hz), 5.62 (1H, dt, J 19.2, 7.2 Hz), 7.35 (1H, d, J 9.8 Hz), 8.24 (1H, d, J 11.2 Hz), 8.35 (1H, s).

(E)-4-(6-Chlorobenzo[d][1,3]dioxol-5-yloxy)-3-fluorobut-2-en-1-amine hydrochloride was synthesized from (E)-tert-butyl 3-fluoro-4-hydroxybut-2-enylcarbamate and 6-chloro-1,3-benzodioxol-5-ol.

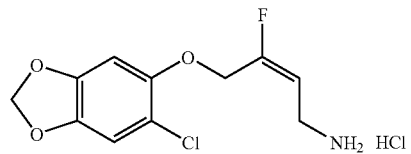 [SMILES: NC/C=C(/F)COc1cc2c(cc1Cl)OCO2 ; Cl]

The product was obtained as a pale yellow powder; m.p.=183-185° C.; ¹H-NMR (200 MHz, CD₃OD): δppm: 3.75 (2H, d, J 8.2 Hz), 4.75 (2H, d, J 16.8 Hz), 5.51 (1H, dt, J 9.0, 8.4 Hz), 5.96 (2H, s), 6.82 (1H, s), 6.90 (1H, s).

(E)-4-(4-Amino-2-fluorobut-2-enyloxy)-N-(3-fluoro-5-(trifluoromethyl)benzyl)benzamide hydrochloride was synthesized from (E)-tert-butyl 3-fluoro-4-hydroxybut-2-enylcarbamate and 4-hydroxy-N-(3-fluoro-5-(trifluoromethyl)benzyl)benzamide.

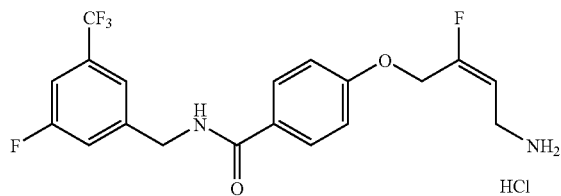 [SMILES: NC/C=C(/F)COc1ccc(C(=O)NCc2cc(F)cc(C(F)(F)F)c2)cc1 ; Cl]

The product was obtained as off white flakes; m.p.=172-175° C.; ¹H-NMR (200 MHz, CD₃OD): δppm: 3.73 (2H, d, J 8.0 Hz), 4.61 (2H, s), 4.86 (2H, d, obscured by H₂O peak), 5.56 (1H, dt, J 16.2, 9.6 Hz), 7.08 (2H, d, J 8.5 Hz), 7.34 (2H, m), 7.49 (1H, s), 7.88 (2H, d, J 8.6 Hz).

(E)-3-Fluoro-4-(4-(morpholinosulfonyl)phenoxy)but-2-en-1-amine was synthesized from (E)-tert-butyl 3-fluoro-4-hydroxybut-2-enylcarbamate and 4-(morpholin-4-ylsulfonyl)phenol.

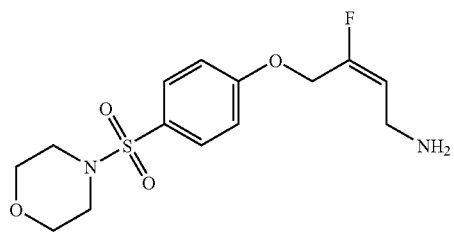 [SMILES: NC/C=C(/F)COc1ccc(S(=O)(=O)N2CCOCC2)cc1]

The product was obtained as a white powder; m.p.=83-85° C.; ¹H-NMR (200 MHz, CDCl₃): δppm: 2.98 (2H, m), 3.40 (2H, d, 8.2 Hz), 3.74 (2H, m), 4.72 (2H, d, J 19.4 Hz), 5.58 (1H, dt, J 19.4, 7.8 Hz), 7.06 (2H, d, J 8.8 Hz), 7.71 (2H, d, J 8.8 Hz).

(E)-4-(4-(4,4-Dimethyl-4,5-dihydrooxazol-2-yl)phenoxy)-3-fluorobut-2-en-1-amine hydrochloride was synthesized from (E)-tert-butyl 3-fluoro-4-hydroxybut-2-enylcarbamate and 4-(4,4-dimethyl-4,5-dihydrooxazol-2-yl)phenol.

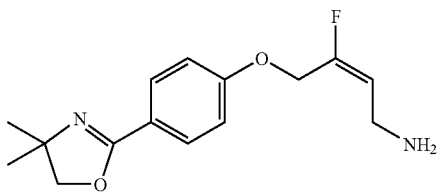 [SMILES: CC1(C)COC(c2ccc(OC/C(F)=C\CN)cc2)=N1]

The product was obtained as a sticky solid. ¹H-NMR (200 MHz, CDCl₃): δppm: 1.37 (6H, s), 3.38 (2H, m br), 4.08 (2H, s), 4.67 (2H, d, J 19.4 Hz), 5.53 (1H, dt, J 19.4, 8.0 Hz), 6.94 (2H, d, J 8.8 Hz), 7.89 (2H, d, J 9.0 Hz).

(E)-3-Fluoro-4-(4-(methylsulfonyl)phenoxy)but-2-en-1-amine hydrochloride was synthesized from (E)-tert-butyl 3-fluoro-4-hydroxybut-2-enylcarbamate and 4-(methylsulfonyl)phenol.

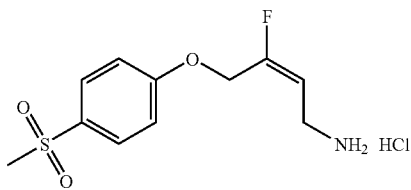 [SMILES: CS(=O)(=O)c1ccc(OC/C(F)=C\CN)cc1 ; Cl]

The product was obtained as an off-white powder; m.p.=197-199° C.; ¹H-NMR (400 MHz, CD₃OD): δppm: 3.09 (3H, s), 3.75 (2H, d, J 8.3 Hz), 4.92 (2H, d, J 18.3 Hz), 5.58 (1H, dt, J 18.2, 8.2 Hz), 7.20 (2H, d, J 8.0 Hz), 7.92 (2H, d, J 8.8 Hz).

(Z)-3-Chloro-4-(2-chloro-4-nitrophenoxy)but-2-en-1-amine hydrochloride was synthesized from (Z)-tert-butyl 3-chloro-4-hydroxybut-2-enylcarbamate and 2-chloro-4-nitrophenol.

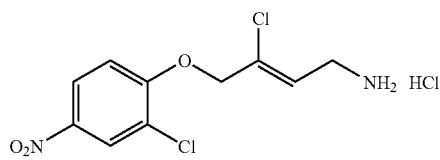 [SMILES: NC/C=C(\Cl)COc1ccc([N+](=O)[O-])cc1Cl ; Cl]

The product was obtained as an white solid; m.p.=203° C. (decomposes); ¹H-NMR (400 MHz, CD₃OD): δppm: 3.83 (2H, d, J 7.6 Hz), 4.84 (2H, s), 6.28 (1H, t, J 8.0 Hz), 7.31 (1H, d, J 8.1 Hz), 8.22 (1H, dd, J 8.0, 2.1 Hz), 8.34 (1H, d, J 1.8 Hz).

(E)-3-Chloro-4-(2-chloro-4-nitrophenoxy)but-2-en-1-amine hydrochloride was synthesized from (E)-tert-butyl 3-chloro-4-hydroxybut-2-enylcarbamate and 2-chloro-4-nitrophenol.

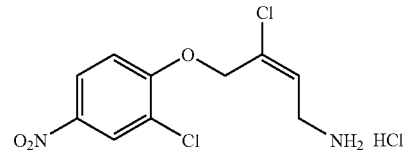 [SMILES: NC/C=C(/Cl)COc1ccc([N+](=O)[O-])cc1Cl ; Cl]

The product was obtained as an white solid; m.p.=180° C. (decomposes); ¹H-NMR (400 MHz, CD₃OD): δppm: 3.89 (2H, d, J 8.0 Hz), 5.07 (2H, s), 6.11 (1H, t, J 7.9 Hz), 7.32 (1H, d, J 8.0 Hz), 8.24 (1H, dd, J 8.0, 2.2 Hz), 8.35 (1H, d, J 2.0 Hz).

(E)-3-Fluoro-4-(4-(methylthio)phenoxy)but-2-en-1-amine hydrochloride was synthesized from (E)-tert-butyl 3-fluoro-4-hydroxybut-2-enylcarbamate and 4-(methylthio)phenol.

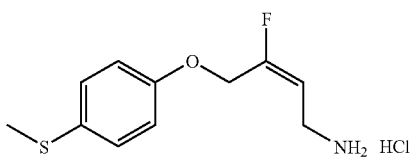

The product was obtained as a white powder; m.p.=132-134° C.; ¹H-NMR (400 MHz, CD₃OD): δppm: 2.42 (3H, s), 3.71 (2H, d, J 7.5 Hz), 4.76 (2H, d, J 17.6 Hz), 5.49 (1H, dt, J 17.6, 7.5 Hz), 6.95 (2H, d, J 8.8 Hz), 7.27 (2H, d, J 8.8 Hz).

(E)-4-(4-tert-Butyl-2-chlorophenoxy)-3-fluorobut-2-en-1-amine hydrochloride was synthesized from (E)-tert-butyl 3-fluoro-4-hydroxybut-2-enylcarbamate and 4-tert-butyl-2-chlorophenol.

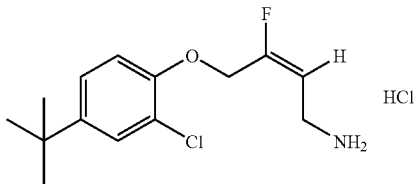 [SMILES: CC(C)(C)c1ccc(OC/C(F)=C\CN)c(Cl)c1 ; Cl]

The product was obtained as a clear oil; $^1$H-NMR (400 MHz, CD$_3$OD): δppm: 3.83 (2H, d, J 7.8 Hz), 4.88 (2H, d, obscured by H$_2$O peak), 5.59 (1H, dt, J 18.6, 7.0 Hz), 7.08 (1H, d, J 8.0 Hz), 7.32 (1H, d, J 7.9 Hz), 7.44 (1H, s).

(E)-3-Fluoro-4-(2-chloro-4-(methylsulfonyl)phenoxy)but-2-en-1-amine hydrochloride was synthesized from (E)-tert-butyl 3-fluoro-4-hydroxybut-2-enylcarbamate and 2-chloro-4-(methylsulfonyl)phenol.

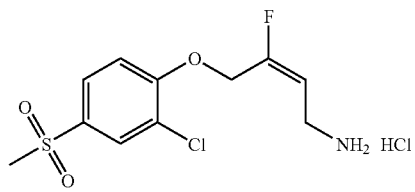 [SMILES: CS(=O)(=O)c1ccc(OC/C(F)=C\CN)c(Cl)c1 ; Cl]

The product was obtained as a white powder; m.p.=177-179° C.; $^1$H NMR (400 MHz, (CD$_3$)$_2$SO): δppm: (3.22 (3H, s), 3.64 (2H, d, J 8.5 Hz) 5.07 (2H, d, J 19.0 Hz), 5.59 (1H, dt, J 19.0, 8.2 Hz), 7.42 (1H, d, J 8.8 Hz), 7.89 (1H, dd, J 8.8, 2.3 Hz), 7.98 (1H, d, J 2.3 Hz), 8.14 (3H, br s).

(E)-4-(4-Amino-2-fluorobut-2-enyloxy)-N-cyclopentylbenzamide hydrochloride was synthesized from (E)-tert-butyl 3-fluoro-4-hydroxybut-2-enylcarbamate and 4-hydroxy-N-cyclopentylbenzamide.

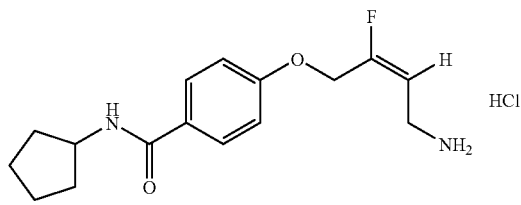 [SMILES: NC/C=C(/F)COc1ccc(C(=O)NC2CCCC2)cc1 ; Cl]

The product was obtained as an off white solid; m.p.=210-213° C.; $^1$H-NMR (400 MHz, CD$_3$OD): δppm: 1.52-1.68 (4H, m), 1.75-1.82 (2H, m), 1.95-2.08 (2H, m), 3.74 (2H, d, J 8.1 Hz), 4.30 (1H, br t, J 6.5 Hz), 4.61 (2H, s), 4.86 (2H, d, obscured by H$_2$O peak), 5.55 (1H, dt, J 18.3, 8.3 Hz), 7.04 (2H, d, J 8.3 Hz), 7.81 (2H, d, J 8.4 Hz).

(E)-4-(4-Amino-2-fluorobut-2-enyloxy)-N,N-dimethylbenzenesulfonamide hydrochloride was synthesized from (E)-tert-butyl 3-fluoro-4-hydroxybut-2-enylcarbamate and 4-hydroxy-N,N-dimethylbenzenesulfonamide.

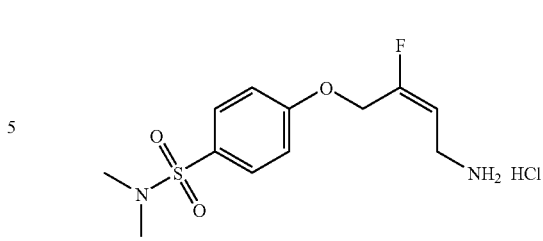

The product was obtained as a white powder; m.p.=153-154° C.; $^1$H-NMR (400 MHz, CD$_3$OD): δppm: 2.69 (6H, s), 3.76 (2H, d, J 8.3 Hz), 4.92 (2H, d, J 18.5 Hz), 5.60 (1H, dt, J 18.5, 8.3 Hz), 7.22 (2H, d, J 9.0 Hz), 7.78 (2H, d, J 9.0 Hz).

(E)-4-(4-Amino-2-fluorobut-2-enyloxy)-N-benzyl-N-methylbenzamide hydrochloride was synthesized from (E)-tert-butyl 3-fluoro-4-hydroxybut-2-enylcarbamate and 4-hydroxy-N-benzyl-N-methylbenzamide.

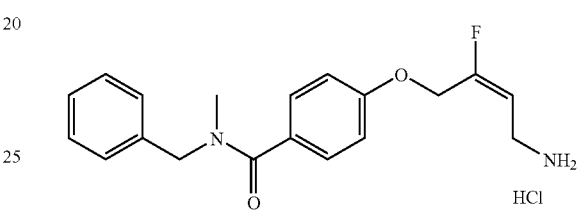

The product was obtained as a colourless oil and a mixture of E/Z-isomers across the amide bond; $^1$H-NMR (400 MHz, CD$_3$OD): δppm: 2.90-3.03 (3H, m), 3.75 (2H, d, J 7.9 Hz), 4.59-4.80 (2H, m), 4.88 (2H, d, obscured by H$_2$O peak), 5.56 (1H, dt, J 18.8, 9.8 Hz), 7.03 (7H, m), 7.49 (2H, d, J 8.4 Hz).

(E)-3-Fluoro-4-(4-(trifluoromethylsulfonyl)phenoxy)but-2-en-1-amine hydrochloride was synthesized from (E)-tert-butyl 3-fluoro-4-hydroxybut-2-enylcarbamate and 4-trifluoromethylsulfonyl)phenol.

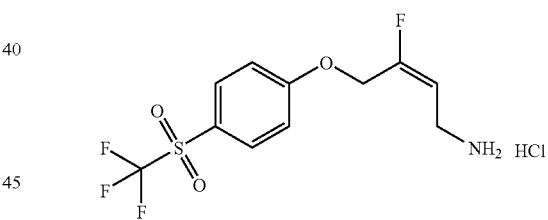

The product was obtained as an off-white powder; m.p.=151-153° C.; $^1$H-NMR (400 MHz, CD$_3$OD): δppm: 3.74 (2H, d, J 8.2 Hz), 4.97 (2H, d, J 18.7 Hz), 5.60 (1H, dt, J 18.7, 8.2 Hz), 7.33 (2H, d, J 9.0 Hz), 8.04 (2H, d, J 9.0 Hz).

(E)-4-(4-Amino-2-fluorobut-2-enyloxy)-N,N-dimethylbenzamide hydrochloride was synthesized from (E)-tert-butyl 3-fluoro-4-hydroxybut-2-enylcarbamate and 4-hydroxy-N,N-dimethylbenzamide.

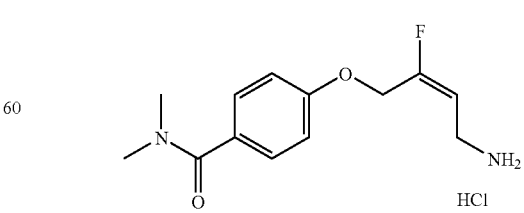

The product was obtained as a colourless oil; $^1$H-NMR (400 MHz, CD$_3$OD): δppm: 3.05 (3H, br s), 3.10 (3H, br s), 3.74

(2H, d, J 8.1 Hz), 4.86 (2H, d, obscured by H₂O peak), 5.56 (1H, m), 7.08 (2H, d, J 8.4 Hz), 7.45 (2H, d, J 8.4 Hz).

(E)-4-(4-Amino-2-fluorobut-2-enyloxy)-N,N-diethylbenzenesulfonamide hydrochloride was synthesized from (E)-tert-butyl 3-fluoro-4-hydroxybut-2-enylcarbamate and N,N-diethyl-4-hydroxybenzenesulfonamide.

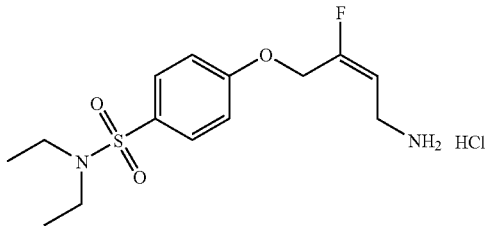 [SMILES: CCN(CC)S(=O)(=O)c1ccc(OC/C(F)=C\CN)cc1 ; Cl]

The product was obtained as a colourless oil; ¹H-NMR (400 MHz, CD₃OD): δppm: 1.11 (6H, t, J 7.2 Hz), 3.21 (4H, q, J 6.8 Hz), 3.74 (2H, d, 8.0 Hz), 4.89 (2H, d, J 20.2 Hz), 5.58 (1H, dt, J 18.4, 8.0 Hz), 7.15 (2H, d, J 8.8 Hz), 7.77 (2H, d, J 8.8 Hz).

(E)-3-Fluoro-4-(4-(methylsulfinyl)phenoxy)but-2-en-1-amine hydrochloride was synthesized from (E)-tert-butyl 3-fluoro-4-hydroxybut-2-enylcarbamate and 4-(methylsulfinyl)phenol.

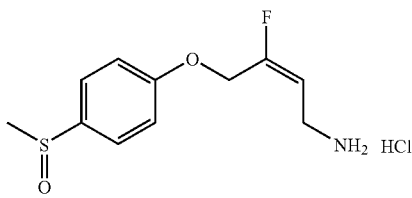 [SMILES: CS(=O)c1ccc(OC/C(F)=C\CN)cc1 ; Cl]

The product was obtained as a colourless oil; ¹H-NMR (400 MHz, CD₃OD): δppm: 2.81 (3H, s), 3.77 (2H, d, J 8.0 Hz), 4.90 (2H, d, J 18.4 Hz), 5.60 (1H, dt, J 18.0, 8.4 Hz), 7.24 (2H, dd, J 8.1, 1.6 Hz), 7.73 (2H, dd, J 7.6, 1.6 Hz).

(E)-3-Fluoro-4-(3-methyl-4-(methylsulfonyl)phenoxy)but-2-en-1-amine hydrochloride was synthesized from (E)-tert-butyl 3-fluoro-4-hydroxybut-2-enylcarbamate and 3-methyl-4-(methylsulfonyl)phenol.

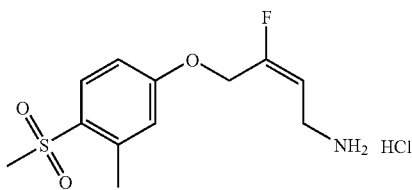 [SMILES: Cc1cc(OC/C(F)=C\CN)ccc1S(C)(=O)=O ; Cl]

The product was obtained as an off-white powder; m.p.=178-180° C.; ¹H-NMR (400 MHz, CD₃OD): δppm: 2.66 (3H, s), 3.09 (3H, s), 3.72 (2H, d, J 8.2 Hz), 4.88 (2H, d, J 18.2 Hz), 5.56 (1H, dt, J 18.2, 8.2 Hz), 7.01 (2H, m), 7.94 (1H, d, J 8.2 Hz).

(E)-(4-(4-Amino-2-fluorobut-2-enyloxy)phenyl)(pyrrolidin-1-yl)methanone hydrochloride was synthesized from (E)-tert-butyl 3-fluoro-4-hydroxybut-2-enylcarbamate and (4-hydroxyphenyl)(pyrrolidin-1-yl)methanone.

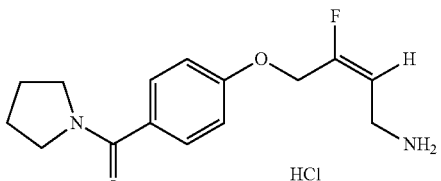

The product was obtained as a colourless oil; ¹H-NMR (400 MHz, CD₃OD): δppm: 1.93-2.01 (4H, m), 3.53 (2H, t, J 6.4 Hz), 3.61 (2H, t, J 6.9 Hz), 3.77 (2H, d, J 8.3 Hz), 4.86 (2H, d, obscured by H₂O peak), 5.57 (1H, dt, J 18.2, 9.9 Hz), 7.09 (2H, d, J 6.8 Hz), 7.57 (2H, d, J 7.4 Hz).

(E)-4-(2-Chlorophenoxy)-3-fluorobut-2-en-1-amine hydrochloride was synthesized from (E)-tert-butyl 3-fluoro-4-hydroxybut-2-enylcarbamate and 2-chlorophenol.

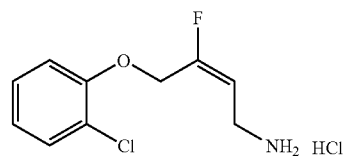 [SMILES: NC/C=C(/F)COc1ccccc1Cl ; Cl]

The product was obtained as an off-white solid; m.p. 98-101° C.; ¹H-NMR (400 MHz, CD₃OD): δppm: 3.82 (2H, d, J 8.2 Hz), 4.86 (2H, d, obscured by H₂O), 5.57 (1H, dt, J 18.8, 8.3 Hz), 7.01 (1H, dd, J 7.4, 7.6 Hz), 7.16 (1H, d, 8.2 Hz), 7.31 (1H, dd, J 8.0, 7.6 Hz), 7.41 (1H, d, 8.0 Hz).

(E)-4-(3-Chlorophenoxy)-3-fluorobut-2-en-1-amine hydrochloride was synthesized from (E)-tert-butyl 3-fluoro-4-hydroxybut-2-enylcarbamate and 3-chlorophenol.

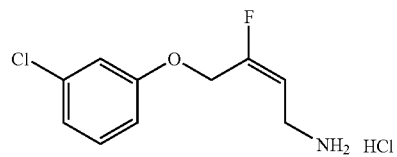 [SMILES: NC/C=C(/F)COc1cccc(Cl)c1 ; Cl]

The product was obtained as a white solid; m.p.=101-104° C.; ¹H-NMR (400 MHz, CD₃OD): δppm: 3.72 (2H, d, J 8.1 Hz), 4.80 (2H, d, J 18.0 Hz), 5.55 (1H, dt, J 17.7, 8.4 Hz), 6.94 (1H, ddd, J 8.0, 1.6, 1.6 Hz), 7.01-7.05 (2H, m), 7.30 (1H, dd, J 8.3, 8.3 Hz).

(E)-4-(3,5-Dichlorophenoxy)-3-fluorobut-2-en-1-amine hydrochloride was synthesized from (E)-tert-butyl 3-fluoro-4-hydroxybut-2-enylcarbamate and 3,5-dichlorophenol.

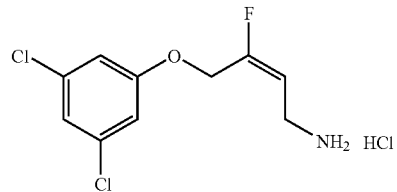 [SMILES: NC/C=C(/F)COc1cc(Cl)cc(Cl)c1 ; Cl]

The product was obtained as a white solid; m.p.=93-95° C.; ¹H-NMR (400 MHz, CD₃OD): δppm: 3.72 (2H, d, J 8.0 Hz), 4.82 (2H, d, obscured by H₂O), 5.57 (1H, dt, 18.1, 8.4 Hz), 7.02 (2H, s), 7.08 (1H, s).

(E)-4-(4-Bromophenoxy)-3-fluorobut-2-en-1-amine hydrochloride was synthesized from (E)-tert-butyl 3-fluoro-4-hydroxybut-2-enylcarbamate and 4-bromophenol.

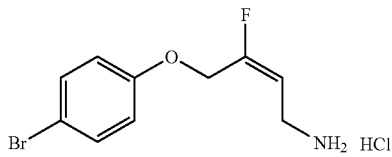 [SMILES: NC/C=C(/F)COc1ccc(Br)cc1 ; Cl]

The product was obtained as a white solid; m.p.=102-105° C.; $^1$H-NMR (400 MHz, CD$_3$OD): δppm: 3.72 (2H, d, J 8.0 Hz), 4.78 (2H, d, J 18.0 Hz), 5.54 (1H, dt, J 16.4, 8.4 Hz), 6.94 (2H, d, J 8.8 Hz), 7.44 (2H, d, J 8.8 Hz).

(E)-3-Fluoro-4-(4-iodophenoxy)but-2-en-1-amine hydrochloride was synthesized from (E)-tert-butyl 3-fluoro-4-hydroxybut-2-enylcarbamate and 4-iodophenol.

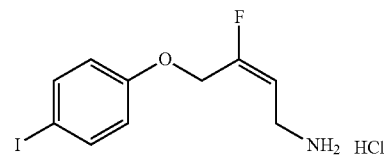 [SMILES: NC/C=C(/F)COc1ccc(I)cc1 ; Cl]

The product was obtained as a white solid; m.p.=125-127° C.; $^1$H-NMR (400 MHz, CD$_3$OD): δppm: 3.71 (2H, d, J 8.4 Hz), 4.76 (2H, d, J 18.0 Hz), 5.53 (1H, dt, J 18.4, 8.0 Hz), 6.82 (2H, d, J 8.8 Hz), 7.61 (2H, d, J 8.8 Hz).

(E)-3-Fluoro-4-(4-(isopropylsulfonyl)phenoxy)but-2-en-1-amine hydrochloride was synthesized from (E)-tert-butyl 3-fluoro-4-hydroxybut-2-enylcarbamate and 4-(isopropylsulfonyl)phenol.

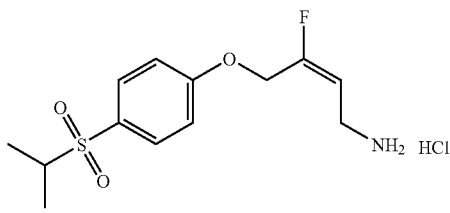 [SMILES: CC(C)S(=O)(=O)c1ccc(OC/C(F)=C\CN)cc1 ; Cl]

The product was obtained as an off-white powder; m.p.=127-129° C.; $^1$H-NMR (400 MHz, CD$_3$OD): δppm: 1.24 (6H, d, J 6.9 Hz), 3.28 (1H, hep, J 6.8 Hz), 3.75 (2H, d, J 8.2 Hz), 4.92 (2H, d, J 18.3 Hz), 5.58 (1H, dt, J 18.1, 8.3 Hz), 7.22 (2H, d, J 9.0 Hz), 7.84 (2H, d, J 9.0 Hz).

(E)-3-Fluoro-4-(4-(pyrrolidin-1-ylsulfonyl)phenoxy)but-2-en-1-amine hydrochloride was synthesized from (E)-tert-butyl 3-fluoro-4-hydroxybut-2-enylcarbamate and 4-(pyrrolidin-1-ylsulfonyl)phenol.

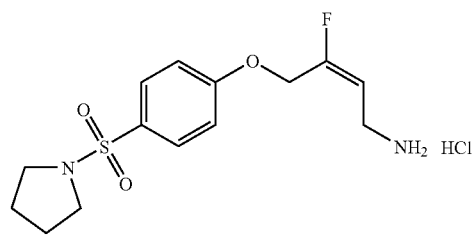 [SMILES: NC/C=C(/F)COc1ccc(S(=O)(=O)N2CCCC2)cc1 ; Cl]

The product was obtained as a colourless oil; $^1$H-NMR (400 MHz, CD$_3$OD): δppm: 1.74 (4H, m), 3.21 (4H, m), 3.76 (2H, d, J 8.1 Hz), 4.91 (2H, d, J 18.4 Hz), 5.59 (1H, dt, J 18.0, 8.5 Hz), 7.20 (2H, d, J 8.7 Hz), 7.81 (2H, d, J 8.4 Hz).

(E)-4-(4-(Ethylsulfonyl)phenoxy)-3-fluorobut-2-en-1-amine hydrochloride was synthesized from (E)-tert-butyl 3-fluoro-4-hydroxybut-2-enylcarbamate and 4-(ethylsulfonyl)phenol.

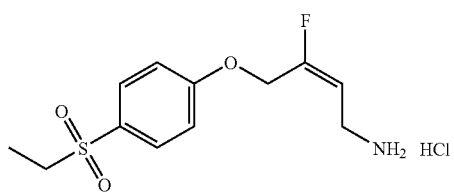 [SMILES: CCS(=O)(=O)c1ccc(OC/C(F)=C\CN)cc1 ; Cl]

The product was obtained as an off-white powder; m.p.=175-177° C.; $^1$H-NMR (400 MHz, CD$_3$OD): δppm: 1.21 (3H, t, J 7.4 Hz), 3.18 (2H, d, J 7.4 Hz), 3.74 (2H, d, J 8.3 Hz), 4.92 (2H, d, J 18.3 Hz), 5.58 (1H, dt, J 18.1, 8.3 Hz), 7.21 (2H, d, J 9.0 Hz), 7.87 (2H, d, J 9.0 Hz).

R/S-(E)-4-(4-Amino-2-fluorobut-2-enyloxy)-N-(1-phenylethyl)benzamide hydrochloride was synthesized from (E)-tert-butyl 3-fluoro-4-hydroxybut-2-enylcarbamate and 4-hydroxy-N-(1-phenylethyl)benzamide.

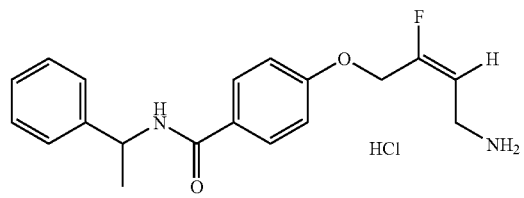 [SMILES: CC(NC(=O)c1ccc(OC/C(F)=C\CN)cc1)c1ccccc1 ; Cl]

The product was obtained as an off white solid; m.p.=175-176° C.; $^1$H-NMR (400 MHz, CD$_3$OD): δppm: 1.56 (3H, d, J 7.0 Hz), 3.74 (2H, d, J 8.2 Hz), 4.87 (2H, d, J 18.1 Hz), 5.23 (1H, q, J 7.0 Hz), 5.56 (1H, dt, J 18.2, 8.4 Hz), 7.07 (2H, d J 8.7 Hz), 7.23 (1H, t, J 7.3 Hz), 7.32 (2H, t, J 7.8 Hz), 7.39 (2H, d, J 7.6 Hz), 7.85 (2H, d J 8.6 Hz).

(E)-4-(4-(Benzylsulfonyl)phenoxy)-3-fluorobut-2-en-1-amine hydrochloride was synthesized from (E)-tert-butyl 3-fluoro-4-hydroxybut-2-enylcarbamate and 4-(benzylsulfonyl)phenol.

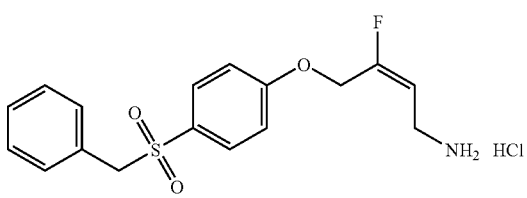 [SMILES: NC/C=C(/F)COc1ccc(S(=O)(=O)Cc2ccccc2)cc1 ; Cl]

The product was obtained as an off-white powder; m.p.=208-210° C.; $^1$H-NMR (400 MHz, CD$_3$OD): δppm: 3.74 (2H, d, J 7.8 Hz), 4.47 (2H, s), 4.88 (2H, d, J 18.3 Hz), 5.58 (1H, dt, J 18.3, 7.8 Hz), 7.11 (4H, m), 7.26 (3H, m), 7.60 (2H, d, J 8.7 Hz).

(E)-4-(Biphenyl-4-yloxy)-3-fluorobut-2-en-1-amine hydrochloride was synthesized from (E)-tert-butyl 3-fluoro-4-bromobut-2-enylcarbamate and 4-phenyl-phenol.

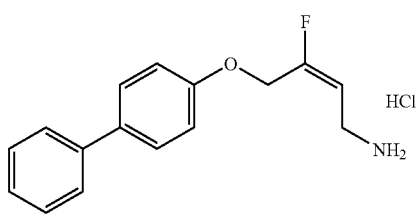 [SMILES: NC/C=C(/F)COc1ccc(-c2ccccc2)cc1 ; Cl]

The product was obtained as a fine white powder; m.p. 208-213° C.; ¹H-NMR (400 MHz, CDCl₃) δppm: 3.62 (2H, d, J 7.6 Hz), 4.901 (2H, d, J 20.0 Hz), 5.56 (1H, rdt, J 18.8, 8.4 Hz), 7.88 (2H, d, J 4.4, 2.0 Hz), 7.31 (1H, t, J 4.4, 2.0, 1.2 Hz), 7.42 (2H, t, J 6.4, 2.0, 1.6 Hz), 7.61 (4H, m), 8.24 (2H, s).

EXAMPLE 5

Procedure D: Preparation of (E)-4-(tert-butoxycarbonylamino)-2-fluorobut-2-enyl methane-sulfonate

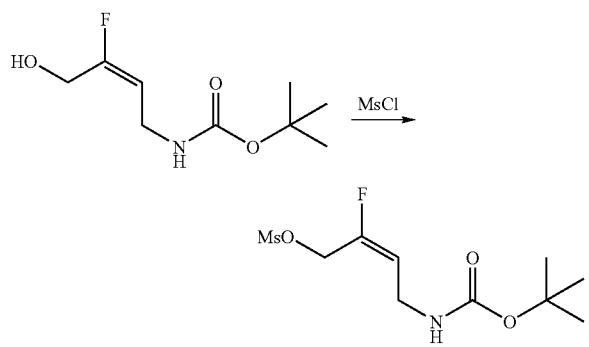

To a stirring solution of (E)-tert-butyl-N-(3-fluoro-4-hydroxybut-2-enyl)carbamate (1.65 g, 8 mmol) in CH₂Cl₂ (30 mL) at 0° C. under nitrogen was added triethylamine (1.67 mL, 12 mmol) followed by methanesulfonyl chloride (0.74 mL, 9.6 mmol). The reaction was left to stir at 0° C. for 1 hr. All volatiles were removed under reduced pressure and the crude yellow residue was taken up in acetone (30 mL). The insoluble white precipitate (triethylammonium chloride) was filtered off and washed with acetone (10 mL). The filtrate containing the crude mesylate was used immediately for Procedure E.

Procedure E: Preparation of (E)-tert-butyl-N-(3-fluoro-4-bromobut-2-enyl)carbamate

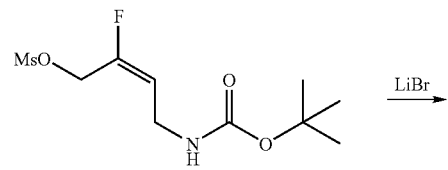

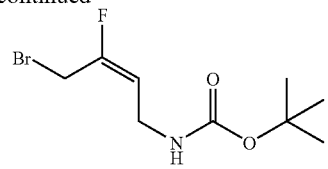

To the stirring filtrate (obtained in the previous step) under nitrogen at 0° C. was added anhydrous lithium bromide (3.48 g, 40 mmol) in five portions over ten min. After stirring at 0° C. for 15 min the reaction vessel was warmed to room temperature and stirring was continued for a further 30 min. Water (50 mL) was added to the mixture and the organic layer extracted with CH₂Cl₂ (3×20 mL), combined, and dried over MgSO₄, filtered and the solvent removed under reduced pressure to afford the crude product as a clear pale yellow oil. Purification through a short silica plug, eluting in 20% EtOAc in hexane afforded (E)-tert-butyl-N-(3-fluoro-4-bromobut-2-enyl)carbamate as a white solid (1.53 g, 71%); ¹H-NMR (200 MHz, CDCl₃): δppm: 1.45 (9H, s), 3.75 (2H, t, J 6.8 Hz), 4.12 (2H, d, J 22.3 Hz), 4.64 (1H, br s), 5.32 (1H, dt, J 17.4, 8.1 Hz).

Procedure F: Preparation of (E)-tert-butyl 4-(4-(cyclohexylcarbamoyl)phenoxy)-3-fluorobut-2-enylcarbamate

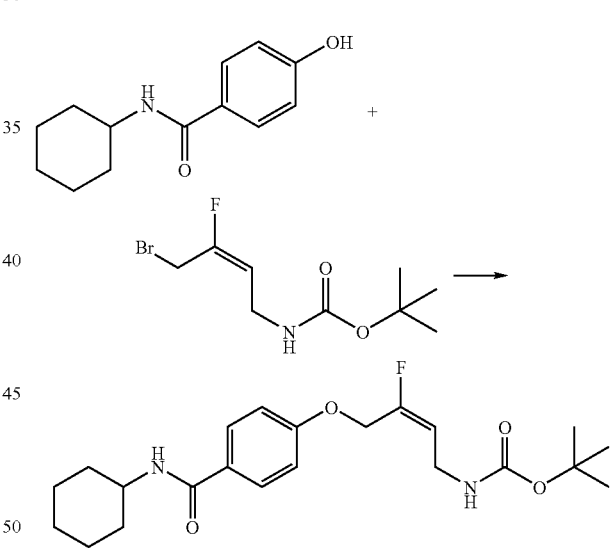

A stirred solution of (E)-tert-butyl-N-(3-fluoro-4-bromobut-2-enyl)carbamate (3.48 g, 13 mmol), N-cyclohexyl-4-hydroxybenzamide (3.55 g, 16.2 mmol) and potassium carbonate (2.76 g, 20 mmol) in DMF (10 mL) under nitrogen was heated at 60° C. for 3 hours at which time TLC analysis showed no remaining allyl bromide. The reaction mixture was allowed to cool and then water (50 mL) added, causing a white precipitate to form. Stirred for 30 minutes, then filtered, washing with water to remove any remaining DMF from the filtercake. The precipitate was then taken up into dichloromethane (150 mL), filtered to remove any insolubles and then washed with NaOH solution (2 M; 20 mL) and brine (20 mL). Dried over MgSO₄, filtered and the solvent removed under reduced pressure to afford the title compound as a white solid (4.23 g, 80%); ¹H-NMR (400 MHz, CDCl₃): δppm:

1.21-1.25 (3H, m), 1.40-1.46 (2H, m), 1.44 (9H, s), 1.61-1.69 (1H, m), 1.73-1.77 (2H, m), 2.01-2.05 (2H, m), 3.80 (2H, t, J 6.7 Hz), 3.96 (1H, m), 4.64 (1H, br s), 4.73 (2H, d, J 19.0 Hz), 5.46 (1H, dt J 18.9, 8.1 Hz), 5.81 (1H, br s), 6.96 (2H, d, J 8.3 Hz), 7.73 (2H, d, J 8.3 Hz).

Procedure G: Preparation of (E)-4-(4-Ammonio-2-fluorobut-2-enyloxy)benzoate hydrochloride

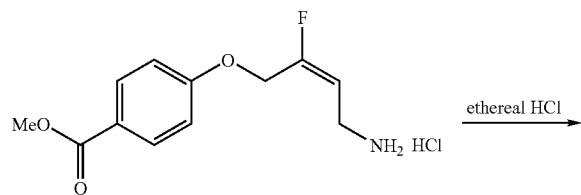

A stirred solution of (E)-Methyl 4-(4-amino-2-fluorobut-2-enyloxy)benzoate hydrochloride (0.050 g, 0.18 mmol) in ethereal HCl solution (1 M; 3 mL) was stirred at reflux for 20 hours. The reaction mixture was allowed to cool to RT and the volatiles were removed under reduced pressure to afford the title compound (0.040 g, 98%) as a fine white powder; m.p.=256-257° C.; $^1$H-NMR (200 MHz, D$_2$O): δppm: 3.77 (2H, d, J 8.4 Hz), 4.91 (2H, d, J 18.8 Hz), 5.65 (1H, dt, J 18.6, 8.0 Hz), 7.08 (2H, d, J 8.4 Hz), 8.00 (2H, d, J 8.4 Hz).

Procedure H: (E)-4-(4-amino-2-fluorobut-2-enyloxy)-N-cyclohexylbenzamide hydrochloride

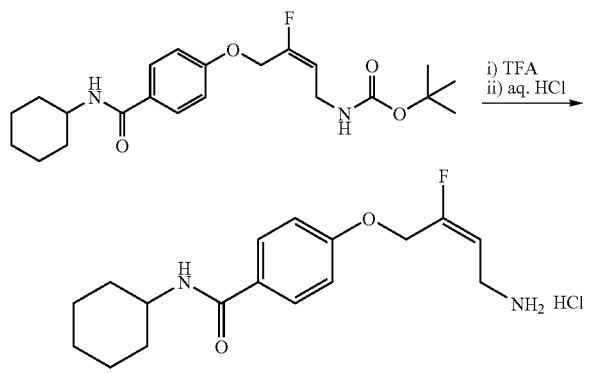

To a stirred solution of (E)-tert-butyl 4-(4-(cyclohexylcarbamoyl)phenoxy)-3-fluorobut-2-enylcarbamate (1.25 g, 3.1 mmol) in dichloromethane (54 mL) was added trifluoroacetic acid (6 mL). The reaction was then stirred at room temperature for 3 hours at which time TLC analysis showed no remaining starting material. Evaporation of the solvent and the remaining acid afforded a brown gum. Aqueous HCl (2 M; 5 mL) was then added and the reaction stirred for 40 minutes, upon which point an off-white solid had precipitated out of solution. Filtered, washing with ice cold aqueous HCl (1 M; 3 mL) and dried in a 60° C. oven to afford the title compound as an off-white powder (0.89 g, 85%); m.p.=210-212° C.; $^1$H-NMR (400 MHz, (CD$_3$)$_2$SO): δppm: 1.11 (1H, m), 1.15-1.33 (4H, m), 1.59 (1H, m), 1.70-1.77 (4H, m), 3.59 (2H, d, J 8.1 Hz), 3.71 (1H, m), 4.87 (2H, d, J 19.8 Hz), 5.52 (1H, dt, J 18.9, 7.8 Hz), 7.01 (2H, d, J 7.9 Hz), 7.83 (2H, d, J 7.9 Hz), 7.97-8.10 (3H, br s, NHs).

EXAMPLE 6

The following compounds were prepared according to procedures A and H described above.

S-(E)-4-(4-Amino-2-fluorobut-2-enyloxy)-N-(1-phenylethyl)benzamide hydrochloride was synthesized from (E)-tert-butyl 3-fluoro-4-hydroxybut-2-enylcarbamate and S-4-hydroxy-N-(1-phenylethyl)benzamide.

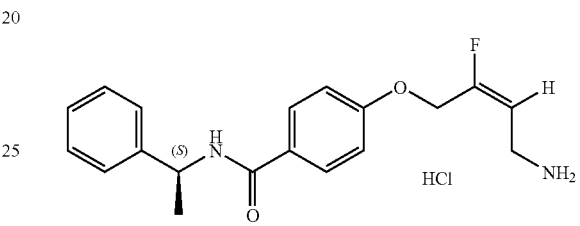

The product was obtained as an off white solid; m.p.=197-198° C.; $^1$H-NMR (400 MHz, CD$_3$OD): δppm: 1.55 (3H, d, J 7.0 Hz), 3.73 (2H, d, J 8.2 Hz), 4.86 (2H, d, obscured by H$_2$O peak), 5.21 (1H, q, J 7.0 Hz), 5.55 (1H, dt, J 18.2, 8.4 Hz), 7.05 (2H, d J 8.7 Hz), 7.22 (1H, t, J 7.3 Hz), 7.31 (2H, t, J 7.8 Hz), 7.38 (2H, d, J 7.6 Hz), 7.85 (2H, d J 8.6 Hz).

R-(E)-4-(4-Amino-2-fluorobut-2-enyloxy)-N-(1-phenylethyl)benzamide hydrochloride was synthesized from (E)-tert-butyl 3-fluoro-4-hydroxybut-2-enylcarbamate and R-4-hydroxy-N-(1-phenylethyl)benzamide.

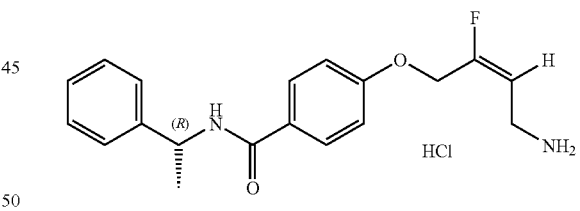

The product was obtained as an off white solid; m.p.=197-198° C.; $^1$H-NMR (400 MHz, CD$_3$OD): δppm: 1.55 (3H, d, J 7.0 Hz), 3.73 (2H, d, J 8.2 Hz), 4.86 (2H, d, obscured by H$_2$O peak), 5.21 (1H, q, J 7.0 Hz), 5.55 (1H, dt, J 18.2, 8.4 Hz), 7.05 (2H, d J 8.7 Hz), 7.22 (1H, t, J 7.3 Hz), 7.31 (2H, t, J 7.8 Hz), 7.38 (2H, d, J 7.6 Hz), 7.85 (2H, d J 8.6 Hz).

EXAMPLE 7

The following compounds were prepared according to procedures F and C described above.

(E)-3-Fluoro-4-(phenylthio)but-2-en-1-amine hydrochloride was synthesized from (E)-tert-butyl 3-fluoro-4-bromobut-2-enylcarbamate and thiophenol.

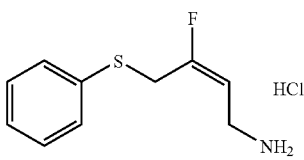 [SMILES: NC/C=C(/F)CSc1ccccc1 ; Cl]

The product was obtained as white flakes; m.p.=143-145° C.; $^1$H-NMR (400 MHz, CD$_3$OD): δppm: 3.12 (2H, d, J 8.2 Hz), 3.78 (2H, d, J 22.3 Hz), 5.24 (1H, dt, J 18.6, 7.3 Hz), 7.38 (3H, m), 7.52 (2H, m).

(E)-3-Fluoro-4-(4-isopropoxyphenoxy)but-2-en-1-amine hydrochloride was synthesized from (E)-tert-butyl 3-fluoro-4-bromobut-2-enylcarbamate and 4-isopropoxyphenol.

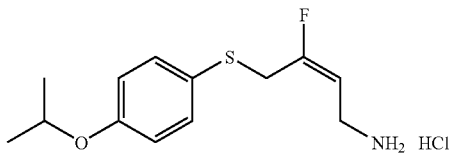 [SMILES: CC(C)Oc1ccc(SC/C(F)=C\CN)cc1 ; Cl]

The product was obtained as an oily white solid; $^1$H-NMR (400 MHz, CD$_3$OD): δppm: 1.28 (6H, d, J 6.0 Hz), 3.70 (2H, d, J 8.4 Hz), 4.48 (1H, m), 4.72 (2H, d, J 17.6 Hz), 5.50 (1H, dt, J 17.2, 8.0 Hz), 6.86 (2H, d, J 8.8 Hz), 6.92 (2H, d, 8.8 Hz).

(E)-4-(4-Amino-2-fluorobut-2-enyloxy)-N-tert-butylbenzamide hydrochloride was synthesized from (E)-tert-butyl 3-fluoro-4-bromobut-2-enylcarbamate and 4-hydroxy-N-tert-butylbenzamide.

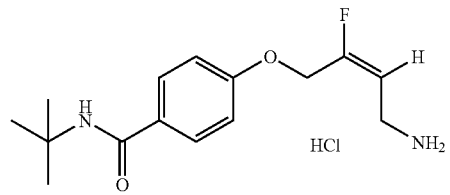 [SMILES: CC(C)(C)NC(=O)c1ccc(OC/C(F)=C\CN)cc1 ; Cl]

The product was obtained as an off white solid; m.p.=189-191° C.; $^1$H-NMR (400 MHz, CD$_3$OD): δppm: 1.46 (9H, s), 3.75 (2H, d, J 8.3 Hz), 4.86 (2H, d, obscured by H$_2$O peak), 5.56 (1H, dt, J 18.2, 8.2 Hz), 7.04 (2H, d, J 8.9 Hz), 7.76 (2H, d, J 8.8 Hz).

(E)-4-(4-(Cyclopentylsulfonyl)phenoxy)-3-fluorobut-2-en-1-amine hydrochloride was synthesized from (E)-tert-butyl 3-fluoro-4-bromobut-2-enylcarbamate and 4-(cyclopentylsulfonyl)phenol.

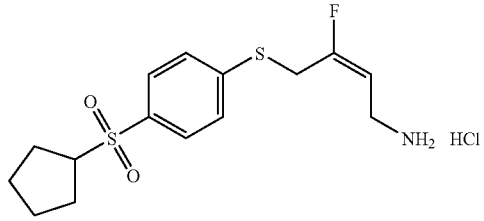 [SMILES: NC/C=C(/F)CSc1ccc(S(=O)(=O)C2CCCC2)cc1 ; Cl]

The product was obtained as an off-white powder; m.p.=136-138° C.; $^1$H-NMR (400 MHz, CD$_3$OD): δppm: 1.63-2.02 (4H, m), 2.11 (1H, m), 3.65 (1H, m), 3.75 (2H, d, J 8.3 Hz), 4.92 (2H, d, J 18.3 Hz), 5.58 (1H, dt, J 18.3, 8.3 Hz), 7.21 (2H, d, J 8.7 Hz), 7.87 (2H, d, J 8.7 Hz).

(E)-3-Fluoro-4-(4-(isobutylsulfonyl)phenoxy)but-2-en-1-amine hydrochloride was synthesized from (E)-tert-butyl -3-fluoro-4-bromobut-2-enylcarbamate and 4-(isobutylsulfonyl)phenol.

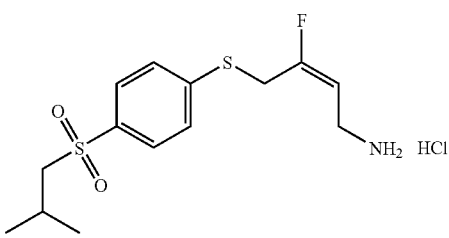 [SMILES: CC(C)CS(=O)(=O)c1ccc(SC/C(F)=C\CN)cc1 ; Cl]

The product was obtained as an off-white powder; m.p.=114-116° C.; $^1$H-NMR (400 MHz, CD$_3$OD): δppm: 1.03 (6H, d, J 6.7 Hz), 2.11 (1H, m), 3.08 (2H, d, J 6.4 Hz), 3.75 (2H, d, J 8.2 Hz), 4.92 (2H, d, J 21.8 Hz), 5.58 (1H, dt, J 18.0, 8.2 Hz), 7.21 (2H, d, J 8.9 Hz), 7.89 (2H, d, J 8.9 Hz).

(E)-3-Fluoro-4-(4-(neopentylsulfonyl)phenoxy)but-2-en-1-amine hydrochloride was synthesized from (E)-tert-butyl -3-fluoro-4-bromobut-2-enylcarbamate and 4-(neopentylsulfonyl)phenol.

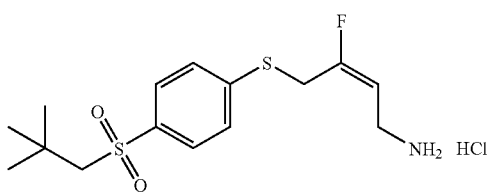 [SMILES: CC(C)(C)CS(=O)(=O)c1ccc(SC/C(F)=C\CN)cc1 ; Cl]

The product was obtained as an off-white powder; m.p.=132-134° C.; $^1$H-NMR (400 MHz, CD$_3$OD): δppm: 1.14 (9H, s), 3.16 (2H, s), 3.75 (2H, d, J 7.6 Hz), 4.91 (2H, d, J 21.6 Hz), 5.58 (1H, dt, J 17.6, 7.6 Hz), 7.20 (2H, d, J 8.2 Hz), 7.89 (2H, d, J 8.2 Hz).

(E)-3-Fluoro-4-(4-(phenethylsulfonyl)phenoxy)but-2-en-1-amine hydrochloride was synthesized from (E)-tert-butyl -3-fluoro-4-bromobut-2-enylcarbamate and 4-(phenethylsulfonyl)phenol.

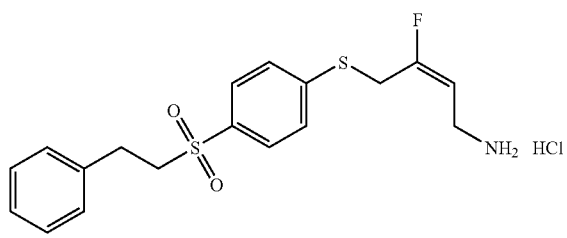 [SMILES: NC/C=C(/F)CSc1ccc(S(=O)(=O)CCc2ccccc2)cc1 ; Cl]

The product was obtained as an off-white powder; m.p.=132-134° C.; $^1$H-NMR (400 MHz, CD$_3$OD): δppm: 2.96 (2H, m), 3.47 (2H, m), 3.75 (2H, d, J 8.2 Hz), 4.92 (2H, d, J 18.3 Hz), 5.58 (1H, dt, J 18.1, 8.5 Hz), 7.19 (7H, m), 7.90 (2H, d, J 8.9 Hz).

(E)-4-(4-(sec-Butylsulfonyl)phenoxy)-3-fluorobut-2-en-1-aminehydrochloride was synthesized from (E)-tert-butyl -3-fluoro-4-bromobut-2-enylcarbamate and 4-(sec-butylsulfonyl)phenol.

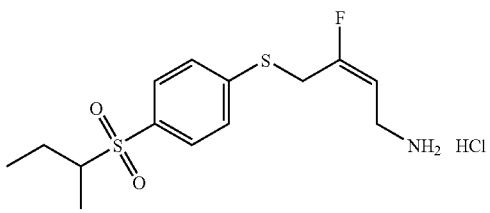 [SMILES: CCC(C)S(=O)(=O)c1ccc(SC/C(F)=C\CN)cc1 ; Cl]

The product was obtained as a white powder; m.p.=103-105° C.; ¹H-NMR (400 MHz, CD₃OD): δppm: 1.01 (3H, t, J 7.5 Hz), 1.26 (3H, d, J 6.9 Hz), 1.43 (1H, m), 1.95 (1H, m), 3.09 (1H, m), 3.78 (2H, d, J 8.2 Hz), 4.95 (2H, d, J 18.4 Hz), 5.61 (1H, dt, J 18.1, 8.3 Hz), 7.24 (2H, d, J 6.9 Hz), 7.86 (2H, d, J 6.9 Hz).

(E)-3-Fluoro-4-(3-methyl-4-(2-methylthiazol-4-yl)phenoxy)but-2-en-1-amine hydrochloride was synthesized from (E)-tert-butyl 3-fluoro-4-bromobut-2-enylcarbamate and 3-methyl-4-(2-methylthiazol-4-yl)phenol.

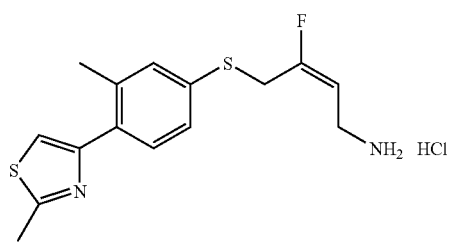 [SMILES: Cc1nc(-c2ccc(SC/C(F)=C\CN)cc2C)cs1 ; Cl]

The product was obtained as a pale yellow solid; ¹H-NMR (400 MHz, d₆-DMSO): δppm: 2.38 (3H, s), 2.70 (3H, s), 3.61 (2H, dt, J 13.6, 6.0 Hz), 4.85 (2H, d, J 20.0 Hz), 5.56 (1H, dt, obscured by H₂O), 6.87-6.92 (2H, m), 7.49 (1H, s), 7.53 (1H, d, J 8.4 Hz), 8.22 (2H, br s).

(E)-3-Fluoro-4-(4-(1-phenylethylsulfonyl)phenoxy)but-2-en-1-amine hydrochloride was synthesized from (E)-tert-butyl -3-fluoro-4-bromobut-2-enylcarbamate and 4-(1-phenylethylsulfonyl)phenol.

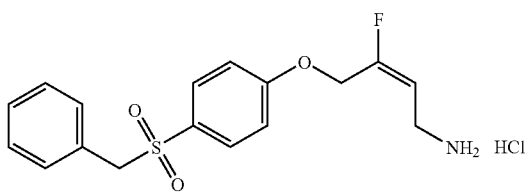 [SMILES: NC/C=C(/F)COc1ccc(S(=O)(=O)Cc2ccccc2)cc1 ; Cl]

The product was obtained as a white powder; m.p.=126-130° C.; ¹H-NMR (400 MHz, DMSO-d₆): δppm: 1.55 (3H, d, J 7.1 Hz), 3.60 (2H, d, J 8.1 Hz), 4.62 (1H, q, J 7.1 Hz), 4.91 (2H, d, J 20.0 Hz), 5.53 (1H, dt, J 18.9, 8.1 Hz), 7.09 (2H, d, J 8.8 Hz), 7.25 (5H, m), 7.53 (2H, d, J 8.7 Hz), 8.05 (3H, brs).

(E)-3-Fluoro-4-(4-(4-fluorobenzylsulfonyl)phenoxy)but-2-en-1-amine hydrochloride was synthesized from (E)-tert-butyl -3-fluoro-4-bromobut-2-enylcarbamate and 4-(4-fluorobenzylsulfonyl)phenol.

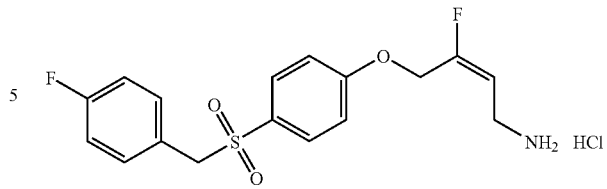

The product was obtained as an off-white powder; m.p.=223-225° C.; ¹H-NMR (400 MHz, DMSO-d₆): δppm: 3.60 (2H, d, J 8.1 Hz), 4.62 (2H, s), 4.93 (2H, d, J 19.9 Hz), 5.53 (1H, dt, J 19.0, 8.1 Hz), 7.13 (6H, m), 7.61 (2H, d, J 8.8 Hz), 8.01 (3H, m).

(E)-4-(9H-Carbazol-2-yloxy)-3-fluorobut-2-en-1-amine hydrochloride was synthesized from (E)-tert-butyl 3-fluoro-4-bromobut-2-enylcarbamate and 9H-carbazol-2-ol.

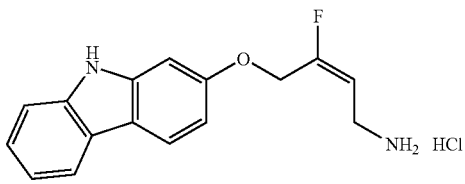 [SMILES: NC/C=C(/F)COc1ccc2c(c1)[nH]c1ccccc12 ; Cl]

The product was obtained as a grey solid; m.p.=243-245° C.; ¹H-NMR (400 MHz, CD₃OD): δppm: 3.75 (2H, d, J 8.1 Hz), 4.87 (2H, d, obscured by H₂O), 5.54 (1H, dt, J 18.4, 8.2 Hz), 6.85 (1H, dd, J 8.6, 2.2 Hz), 7.05 (1H, d, J 2.2 Hz), 7.12 (1H, ddd, 7.8, 7.6, 0.9 Hz), 7.30 (1H, ddd, J 7.9, 7.8, 1.0 Hz), 7.40 (1H, dd, J 8.4, 0.8 Hz), 7.95 (2H, d, 8.5 Hz).

(E)-4-(4-(1H-Imidazol-1-yl)phenoxy)-3-fluorobut-2-en-1-amine hydrochloride was synthesized from (E)-tert-butyl 3-fluoro-4-bromobut-2-enylcarbamate and 4-(1H-imidazol-1-yl)phenol.

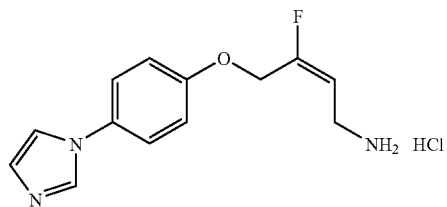 [SMILES: NC/C=C(/F)COc1ccc(-n2ccnc2)cc1 ; Cl]

The product was obtained as an off-white solid; m.p.=223-225° C.; ¹H-NMR (400 MHz, CD₃OD): δppm: 3.81 (2H, d, J 8.2 Hz), 4.95 (2H, d, J 18.4 Hz), 5.63 (1H, dt, J 18.0, 8.3 Hz), 7.30 (2H, d, J 8.9 Hz), 7.74 (2H, d, J 9.0 Hz), 7.80 (1H, s), 8.05 (1H, s), 9.42 (1H, s).

(E)-4-(4-Amino-2-fluorobut-2-enyloxy)-N-isopropylbenzamide hydrochloride was synthesized from (E)-tert-butyl 3-fluoro-4-bromobut-2-enylcarbamate and 4-hydroxy-N-isopropylbenzamide.

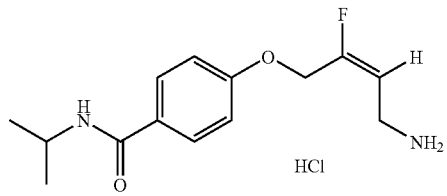 [SMILES: CC(C)NC(=O)c1ccc(OC/C(F)=C\CN)cc1 ; Cl]

The product was obtained as an off white solid; m.p.=206-208° C.; ¹H-NMR (400 MHz, (CD₃)₂SO): δppm: 1.14 (6H, d, J 6.6 Hz), 3.60 (2H, d, J 7.9 Hz), 4.06 (1H, septet, J 7.6 Hz), 4.87 (2H, d, J 20.0 Hz), 5.53 (1H, dt, J 19.1, 8.1 Hz), 7.02 (2H, d, J 8.9 Hz), 7.83 (2H, d, J 8.9 Hz), 8.02-8.14 (3H, br s, NHs).

(E)-4-(4-Amino-2-fluorobut-2-enyloxy)-N-phenylbenzamide hydrochloride was synthesized from (E)-tert-butyl 3-fluoro-4-bromobut-2-enylcarbamate and 4-hydroxy-N-phenylbenzamide.

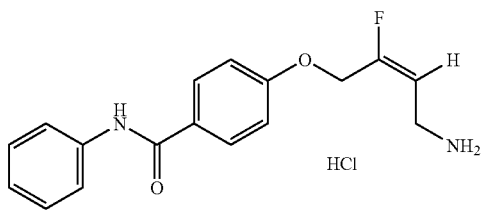 [SMILES: NC/C=C(/F)COc1ccc(C(=O)Nc2ccccc2)cc1 ; Cl]

The product was obtained as white flakes; $^1$H-NMR (400 MHz, CD$_3$OD): δppm: 3.73 (2H, d, J 8.3 Hz), 4.88 (2H, d, J 18.1 Hz), 5.56 (1H, dt, J 18.3, 8.2 Hz), 7.12 (3H, m), 7.36 (2H, t, J 7.5 Hz), 7.66 (2H, d, J 8.6 Hz), 7.96 (2H, d, J 8.9 Hz).

(E)-3-Fluoro-4-(2-methylbenzo[d]thiazol-5-yloxy)but-2-en-1-amine hydrochloride was synthesized from (E)-tert-butyl 3-fluoro-4-bromobut-2-enylcarbamate and 2-methylbenzo[d]thiazol-5-ol.

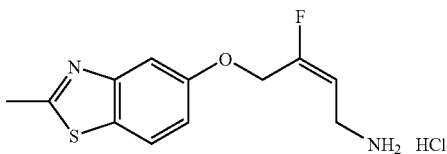 [SMILES: Cc1nc2cc(OC/C(F)=C\CN)ccc2s1 ; Cl]

The product was obtained as an off-white solid; m.p.=215-217° C.; $^1$H-NMR (400 MHz, CD$_3$OD): δppm: 3.00 (3H, s), 3.78 (2H, d, J 8.4 Hz), 4.95 (2H, d, J 18.0 Hz), 5.60 (1H, dt, J 18.0, 8.4 Hz), 7.28 (1H, dd, J 9.2, 1.2 Hz), 7.57 (1H, d, J 1.4 Hz), 8.00 (1H, d, J 8.8 Hz).

(E)-4-(Benzo[d]thiazol-2-yloxy)-3-fluorobut-2-en-1-amine hydrochloride was synthesized from (E)-tert-butyl 3-fluoro-4-bromobut-2-enylcarbamate and benzo[d]thiazol-2-ol.

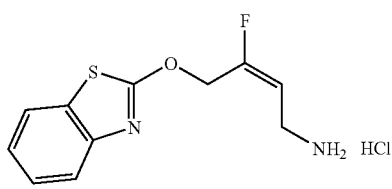 [SMILES: NC/C=C(/F)COc1nc2ccccc2s1 ; Cl]

The product was obtained as a white solid; m.p.=197-199° C.; $^1$H-NMR (400 MHz, CD$_3$OD): δppm: 3.91 (2H, d, J 8.7 Hz), 4.95 (2H, d, J 20.8 Hz), 5.54 (1H, dt, J 18.4, 8.2 Hz), 7.25 (1H, dd, J 7.0, 7.2 Hz), 7.39-7.45 (2H, m), 7.59 (1H, d, J 7.4 Hz).

(E)-N-(4-(4-Amino-2-fluorobut-2-enyloxy)phenyl)acetamide hydrochloride was synthesized from (E)-tert-butyl-3-fluoro-4-bromobut-2-enylcarbamate and N-(4-hydroxyphenyl)acetamide.

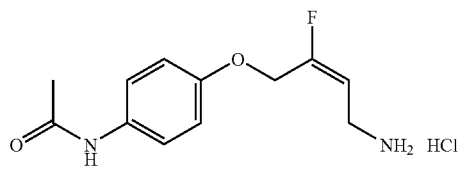 [SMILES: CC(=O)Nc1ccc(OC/C(F)=C\CN)cc1 ; Cl]

The product was obtained as an off-white powder; m.p.=218-220° C.; $^1$H-NMR (400 MHz, DMSO-d$_6$): δppm: 2.0 (3H, s), 3.58 (2H, m), 4.76 (2H, d, J 20.0 Hz), 5.49 (1H, dt, J 19.1, 8.1 Hz), 6.92 (2H, d, J 9.0 Hz), 7.51 (2H, d, J 9.0 Hz), 8.04 (3H, brs), 9.86 (1H, s).

(E)-7-(4-Amino-2-fluorobut-2-enyloxy)-3-(4-hydroxyphenyl)-4H-chromen-4-one hydrochloride was synthesized from (E)-tert-butyl-3-fluoro-4-bromobut-2-enylcarbamate and 7-hydroxy-3-(4-hydroxyphenyl)-4H-chromen-4-one.

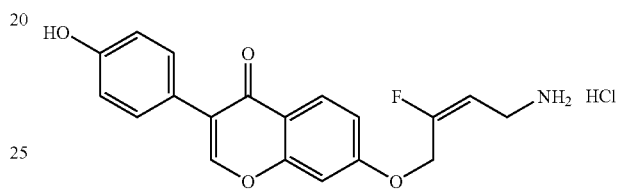

The product was obtained as an off-white powder; m.p.=274-276° C.; $^1$H-NMR (400 MHz, DMSO-d$_6$): δppm: 3.65 (2H, d, J 8.0 Hz), 5.03 (2H, d, J 20.1 Hz), 5.58 (1H, dt, J 18.9, 8.0 Hz), 6.82 (2H, d, J 8.8 Hz), 7.13 (1H, dd, J 8.8, 2.4 Hz), 7.24 (1H, d, J 2.4 Hz), 7.40 (1H, d, J 8.9 Hz), 8.07 (2H, d, J 8.9 Hz), 8.07 (3H, brs), 8.40 (1H, s), 9.57 (1H, s).

(E)-3-Fluoro-4-(pyridin-3-yloxy)but-2-en-1-amine hydrochloride was synthesized from (E)-tert-butyl 3-fluoro-4-bromobut-2-enylcarbamate and pyridin-3-ol.

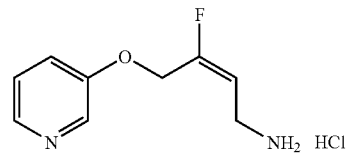 [SMILES: NC/C=C(/F)COc1cccnc1 ; Cl]

The product was obtained as a brown solid; m.p.=193-196° C.; $^1$H-NMR (400 MHz, CD$_3$OD): δppm: 3.79 (2H, d, J 8.2 Hz), 5.14 (2H, d, J 19.2 Hz), 5.68 (1H, dt, J 18.0, 8.3 Hz), 8.08 (1H, dd, J 8.8, 5.6 Hz), 8.35 (1H, dd, J 8.8, 2.8 Hz), 8.55 (1H, d, J 5.2 Hz), 8.73 (1H, d, J 2.4 Hz).

(E)-3-Fluoro-4-(2-p-tolylbenzo[d]thiazol-6-yloxy)but-2-en-1-amine hydrochloride was synthesized from (E)-tert-butyl 3-fluoro-4-bromobut-2-enylcarbamate and 2-p-tolylbenzo[d]thiazol-6-ol.

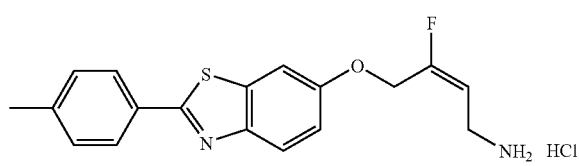 [SMILES: Cc1ccc(-c2nc3ccc(OC/C(F)=C\CN)cc3s2)cc1 ; Cl]

The product was obtained as a tan solid; m.p.=155-157° C.; $^1$H-NMR (400 MHz, d$_6$-DMSO): δppm: 2.37 (3H, s), 3.61 (2H, dt, J 11.2, 5.2 Hz), 4.93 (2H, d, J 20.1 Hz), 5.57 (1H, dt, J 18.8, 8.0 Hz), 7.18 (1H, dd, J 8.8, 2.4 Hz), 7.35 (2H, dd, J 7.6, 1.6 Hz), 7.77 (1H, d, J 1.2 Hz), 7.91-7.95 (3H, m), 8.29 (2H, br s).

(E)-2-(4-(4-Amino-2-fluorobut-2-enyloxy)phenylsulfonyl)ethanol hydrochloride was synthesized from (E)-tert-butyl 3-fluoro-4-bromobut-2-enylcarbamate and 4-(2-hydroxyethylsulfonyl)phenol.

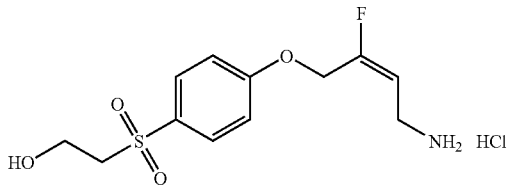 [SMILES: NC/C=C(/F)COc1ccc(S(=O)(=O)CCO)cc1 ; Cl]

The product was obtained as an off white solid; m.p.=166-168° C.; $^1$H-NMR (400 MHz, CD$_3$OD): δppm: 3.39 (2H, t, J 3.2 Hz), 3.75 (2H, d, J 8.2 Hz), 3.86 (2H, t, J 3.2 Hz), 4.92 (2H, d, J 18.3 Hz), 5.59 (1H, dt, J 15.4, 8.3 Hz), 7.21 (2H, d, J 9.0 Hz), 7.90 (2H, dd, J 9.0, 2.1 Hz).

(E)-3-Fluoro-4-(4-(2-morpholinoethylsulfonyl)phenoxy)but-2-en-1-amine hydrochloride was synthesized from (E)-tert-butyl 3-fluoro-4-bromobut-2-enylcarbamate and 4-(2-morpholinoethylsulfonyl)phenol.

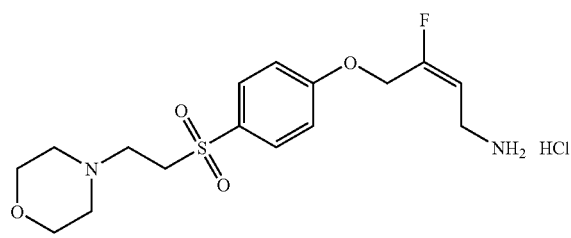 [SMILES: NC/C=C(/F)COc1ccc(S(=O)(=O)CCN2CCOCC2)cc1 ; Cl]

The product was obtained as a white solid; m.p.=200-202° C.; $^1$H-NMR (400 MHz, CD$_3$OD): δppm: 3.30 (2H, t, J 9.4 Hz), 3.59-3.71 (5H, m), 3.84-3.95 (5H, m), 4.13 (2H, d, J 12.4 Hz), 5.05 (2H, d, J 18.2 Hz), 5.70 (1H, dt, J 18.1, 8.4 Hz), 7.36 (2H, d, J 8.8 Hz), 8.05 (2H, d, 8.8 Hz).

(E)-3-Fluoro-4-(4-(2-(pyrrolidin-1-yl)ethylsulfonyl)phenoxy)but-2-en-1-amine hydrochloride was synthesized from (E)-tert-butyl 3-fluoro-4-bromobut-2-enylcarbamate and 4-(2-(pyrrolidin-1-yl)ethylsulfonyl)phenol.

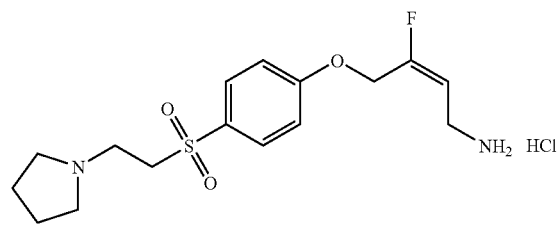 [SMILES: NC/C=C(/F)COc1ccc(S(=O)(=O)CCN2CCCC2)cc1 ; Cl]

The product was obtained as an off-white solid; m.p.=194-197° C.; $^1$H-NMR (400 MHz, CD$_3$OD): δppm: 1.99-2.16 (4H, m), 3.10-3.15 (2H, br s), 3.60 (2H, t, J 6.8 Hz), 3.70-3.77 (6H, m), 4.96 (2H, d, J 18.4 Hz), 5.61 (1H, dt, J 18.0, 8.3 Hz), 7.27 (2H, d, J 9.0 Hz), 7.96 (2H, d, J 8.9 Hz).

(E)-3-Fluoro-4-(4-(2-(piperidin-1-yl)ethylsulfonyl)phenoxy)but-2-en-1-amine hydrochloride was synthesized from (E)-tert-butyl 3-fluoro-4-bromobut-2-enylcarbamate and 4-(2-(piperidin-1-yl)ethylsulfonyl)phenol.

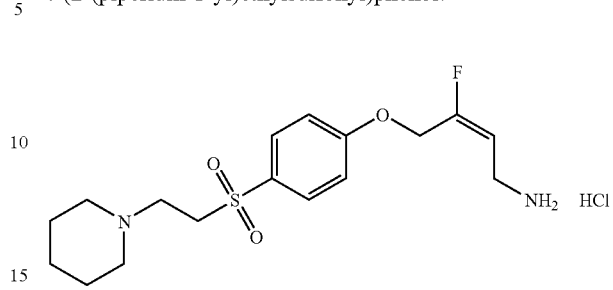

The product was obtained as an off-white solid; m.p.=215° C. (decomposes); $^1$H-NMR (400 MHz, CD$_3$OD): δppm: 1.46-1.55 (1H, m), 1.81-1.95 (5H, m), 3.00 (2H, t, J 10.8 Hz), 3.45-3.57 (4H, m), 3.77-3.85 (4H, m), 4.97 (2H, d, J 18.4 Hz), 5.62 (1H, dt, J 18.2, 9.4 Hz), 7.28 (2H, d, J 8.4 Hz), 7.97 (2H, d, J 8.4 Hz).

(E)-4-(5-Chloropyridin-3-yloxy)-3-fluorobut-2-en-1-amine dihydrochloride was synthesized from (E)-tert-butyl 3-fluoro-4-bromobut-2-enylcarbamate and 5-chloro-3-hydroxypyridine.

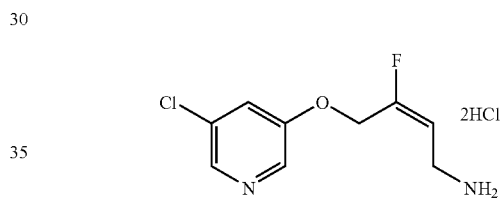

The product was obtained as an off white powder; m.p.=147-150° C.; $^1$H-NMR (400 MHz, (CD$_3$)$_2$SO): δppm: 3.61 (2H, m), 4.98 (2H, d, J 20.3 Hz), 5.59 (1H, dt, J 19.0, 8.1 Hz), 7.71 (1H, s), 8.25-8.34 (5H, m, PyH & NHs).

(E)-3-Fluoro-4-(2-methylpyridin-3-yloxy)but-2-en-1-amine dihydrochloride was synthesized from (E)-tert-butyl 3-fluoro-4-bromobut-2-enylcarbamate and 3-hydroxy-2-methylpyridine.

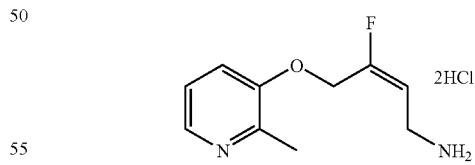

The product was obtained as an off white powder; m.p.=195-196° C.; $^1$H-NMR (400 MHz, (CD$_3$)$_2$SO): δppm: 2.58 (3H, s), 3.63 (2H, m), 5.09 (2H, d, J 19.8 Hz), 5.63 (1H, dt, J 18.9, 8.1 Hz), 7.79 (1H, dd, J 8.5, 5.6 Hz), 8.04 (1H, d, J 8.5 Hz), 8.33 (1H, d, J 5.5 Hz).

(E)-3-Fluoro-4-(6-methylpyridin-3-yloxy)but-2-en-1-amine dihydrochloride was synthesized from (E)-tert-butyl 3-fluoro-4-bromobut-2-enylcarbamate and 5-hydroxy-2-mahylpyridine.

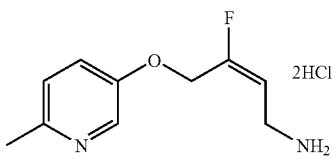

The product was obtained as an off white powder; m.p.=189-191° C.; $^1$H-NMR (400 MHz, (CD$_3$)$_2$SO): δppm: 2.63 (3H, s), 3.62 (2H, m), 5.07 (2H, d, J 20.1 Hz), 5.61 (1H, dt, J 19.1, 8.1 Hz), 7.73 (1H, d, J 8.9 Hz), 8.01 (1H, dd, J 8.8, 2.5 Hz), 8.27 (3H, br s, NHs), 8.49 (1H, d, J 2.8 Hz).

(E)-3-Fluoro-4-(2-methylbenzo[d]thiazol-6-yloxy)but-2-en-1-amine hydrochloride was synthesized from (E)-tert-butyl 3-fluoro-4-bromobut-2-enylcarbamate and 2-methylbenzo[d]thiazol-6-ol.

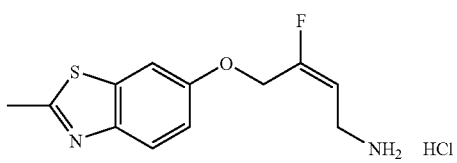 [SMILES: Cc1nc2ccc(OC/C(F)=C\CN)cc2s1 ; Cl]

The product was obtained as an off-white solid; m.p.=205-213° C.; $^1$H-NMR (400 MHz, d$_6$-DMSO): δppm: 2.74 (3H, s), 3.60 (2H, dt, J 12.0, 6.0 Hz), 4.89 (2H, d, J 20.0 Hz), 5.56 (1H, dt, J 19.2, 8.0 Hz), 7.12 (1H, dd, J 8.8, 2.4 Hz), 7.67 (1H, d, J 2.4 Hz), 7.81 (1H, d, J 8.8 Hz), 8.25 (2H, br s).

(E)-4-(4-Amino-2-fluorobut-2-enyloxy)-N-isopropylbenzenesulfonamide hydrochloride was synthesized from (E)-tert-butyl -3-fluoro-4-bromobut-2-enylcarbamate and 4-hydroxy-N-(propan-2-yl)benzenesulfonamide.

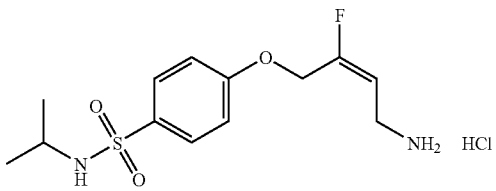 [SMILES: CC(C)NS(=O)(=O)c1ccc(OC/C(F)=C\CN)cc1 ; Cl]

The product was obtained as an off-white powder; m.p.=92-95° C.; $^1$H-NMR (400 MHz, DMSO-d$_6$): δppm: 0.93 (6H, d, J 6.5 Hz), 3.19 (1H, m), 3.62 (2H, d, J 8.1 Hz), 4.92 (2H, d, J 20.0 Hz), 5.53 (1H, dt, J 18.9, 8.1 Hz), 7.14 (2H, d, J 8.9 Hz), 7.44 (1H, d, J 7.1 Hz), 7.77 (2H, d, J 9.0 Hz), 8.00 (3H, brs).

(E)-4-(4-Amino-2-fluorobut-2-enyloxy)-N-cyclohexylbenzene-sulfonamide hydrochloride was synthesized from (E)-tert-butyl -3-fluoro-4-bromobut-2-enylcarbamate and N-cyclohexyl-4-hydroxybenzenesulfonamide.

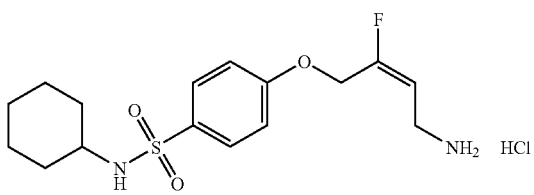 [SMILES: NC/C=C(/F)COc1ccc(S(=O)(=O)NC2CCCCC2)cc1 ; Cl]

The product was obtained as an off-white powder; m.p.=198-200° C.; $^1$H-NMR (400 MHz, DMSO-d$_6$): δppm: 1.07 (5H, m), 1.50 (5H, m), 2.86 (1H, m), 3.62 (2H, d, J 8.1 Hz), 4.92 (2H, d, J 20.1 Hz), 5.54 (1H, dt, J 19.0, 8.1 Hz), 7.13 (2H, d, J 9.0 Hz), 7.50 (1H, d, J 7.3 Hz), 7.75 (2H, d, J 9.0 Hz), 8.05 (3H, brs).

(E)-4-(4-Amino-2-fluorobut-2-enyloxy)-N-(1-phenylethyl)benzene-sulfonamide hydrochloride was synthesized from (E)-tert-butyl-3-fluoro-4-bromobut-2-enylcarbamate and 4-hydroxy-N-(1-phenylethyl)benzenesulfonamide.

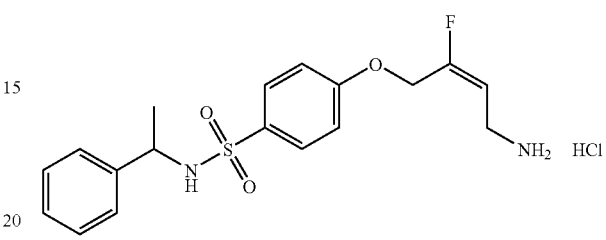

The product was obtained as a white powder; m.p.=198-200° C.; $^1$H-NMR (400 MHz, DMSO-d$_6$): δppm: 1.17 (3H, d, J 7.2 Hz), 3.61 (2H, d, J 8.0 Hz), 4.29 (1H, q, J 7.2 Hz), 4.88 (2H, d, J 19.6 Hz), 5.54 (1H, dt, J 19.6, 8.0 Hz), 7.03 (2H, d, J 8.8 Hz), 7.18 (5H, m), 7.62 (2H, d, J 8.8 Hz), 8.06 (3H, brs), 8.07 (1H, d, J 8.0 Hz).

(E)-3-Fluoro-4-(4-(4-(4-methoxyphenyl)thiazol-2-yl)phenoxy)but-2-en-1-amine hydro-chloride was synthesized from (E)-tert-butyl 3-fluoro-4-bromobut-2-enylcarbamate and 4-(4-(4-methoxyphenyl)thiazol-2-yl)phenol.

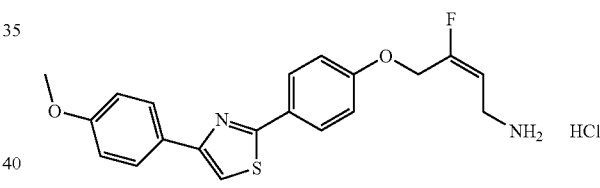

The product was obtained as a yellow solid; m.p.=230-232° C.; $^1$H-NMR (400 MHz, d$_6$-DMSO): δppm: 3.62 (2H, dt, J 12.2, 6.4 Hz), 3.79 (3H, s), 4.92 (2H, d, J 20.2 Hz), 5.55 (1H, dt, J 18.0, 8.4 Hz), 7.02 (2H, dd, J 7.6, 1.8 Hz), 7.12 (2H, dd, J 7.8, 1.6 Hz), 7.92-7.98 (5H, m), 8.13 (2H, br s).

(E)-3-Fluoro-4-(phenylsulfonyl)but-2-en-1-amine hydrochloride was synthesized from (E)-tert-butyl 3-fluoro-4-bromobut-2-enylcarbamate and sodium benzenesulfinate

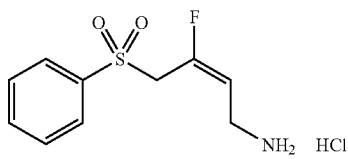 [SMILES: NC/C=C(/F)CS(=O)(=O)c1ccccc1 ; Cl]

The product was obtained as a white powder; m.p.=159-161° C.; $^1$H-NMR (400 MHz, DMSO-d$_6$): δppm: 3.09 (2H, d, J 8.0 Hz), 4.70 (2H, d, J 21.3 Hz), 5.51 (1H, dt, J 18.0, 7.9 Hz), 7.77 (5H, m), 7.91 (3H, brs).

(S,E)-4-(4-Amino-2-fluorobut-2-enyloxy)-N-(1-phenylethyl)benzenesulfonamide was synthesized from (E)-tert-butyl-3-fluoro-4-bromobut-2-enylcarbamate and (S)-4-hydroxy-N-(1-phenylethyl)benzenesulfonamide.

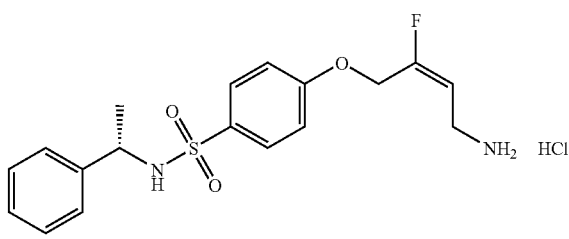 [SMILES: C[C@H](NS(=O)(=O)c1ccc(OC/C(F)=C\CN)cc1)c1ccccc1 ; Cl]

The product was obtained as a white solid. $^1$H-NMR (400 MHz, DMSO-d$_6$): δppm: 1.16 (3H, d, J 7.2 Hz), 3.60 (2H, d, J 8.0 Hz), 4.27 (1H, q, J 7.2 Hz), 4.88 (2H, d, J 19.6 Hz), 5.53 (1H, dt, J 19.2, 8.0 Hz), 7.02 (2H, d, J 8.8 Hz), 7.18 (5H, m), 7.62 (2H, d, J 8.8 Hz), 8.06 (1H, d, J 8.0 Hz), 8.11 (3H, brs).

(E)-4-(2-tert-Butylbenzo[d]thiazol-5-yloxy)-3-fluorobut-2-en-1-amine hydrochloride was synthesized from (E)-tert-butyl 3-fluoro-4-bromobut-2-enylcarbamate and 2-tert-butylbenzo[d]thiazol-5-ol.

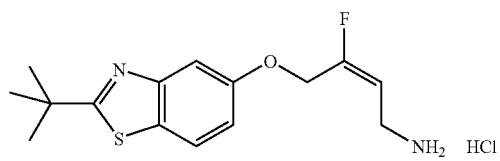 [SMILES: CC(C)(C)c1nc2cc(OC/C(F)=C\CN)ccc2s1 ; Cl]

The product was obtained as a tan solid; m.p.=132-135° C.; $^1$H-NMR (400 MHz, d$_6$-DMSO): δppm: 1.42 (9H, s), 3.61 (2H, dt, obscured by H$_2$O), 4.90 (2H, d, J 20.1 Hz), 5.50 (1H, dt, J 18.6, 8.6 Hz), 7.06 (1H, dd, J 8.8, 2.4 Hz), 7.60 (1H, d, J 2.8 Hz), 7.92 (1H, dd, J 8.8, 2.8 Hz), 8.21 (2H, br s).

(E)-3-Fluoro-4-(2-p-tolylbenzo[d]thiazol-5-yloxy)but-2-en-1-amine hydrochloride was synthesized from (E)-tert-butyl 3-fluoro-4-bromobut-2-enylcarbamate and 2-p-tolylbenzo[d]thiazol-5-ol.

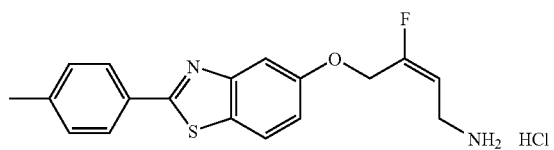

The product was obtained as a pale yellow solid; $^1$H-NMR (400 MHz, d$_6$-DMSO): δppm: 2.34 (3H, s), 4.92 (2H, d, J 20.0 Hz), 5.54 (1H, dt, J 18.8, 8.0 Hz), 7.09 (1H, d, J 8.4 Hz), 7.33 (2H, d, J 8.0 Hz), 7.64 (1H, s), 7.91 (2H, d, J 7.6 Hz), 7.98 (1H, d, J 8.8 Hz), 8.22 (2H, br s).

(E)-4-(2-Cyclohexylbenzo[d]thiazol-5-yloxy)-3-fluorobut-2-en-1-amine hydrochloride was synthesized from (E)-tert-butyl 3-fluoro-4-bromobut-2-enylcarbamate and 2-cyclohexylbenzo[d]thiazol-5-ol.

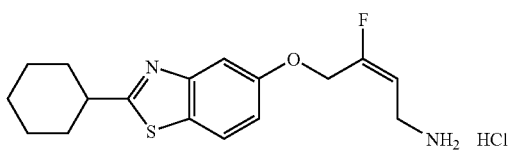 [SMILES: NC/C=C(/F)COc1ccc2sc(C3CCCCC3)nc2c1 ; Cl]

The product was obtained as an off-white solid; m.p.=123-127° C.; $^1$H-NMR (400 MHz, d$_6$-DMSO): δppm: 1.15-1.28 (1H, m), 1.32-1.43 (2H, m), 1.48-1.55 (2H, m), 1.62-1.67 (1H, m), 1.73-1.78 (2H, m), 2.05-2.08 (2H, m), 3.02-3.10 (1H, m), 4.88 (2H, d, J 20.0 Hz), 5.52 (1H, dt, J 19.2, 8.7 Hz), 7.04 (1H, dd, J 8.8, 2.4 Hz), 7.55 (1H, d, J 2.4 Hz), 7.90 (1H, d, J 8.8 Hz), 8.16 (2H, br s).

(E)-3-Fluoro-4-methoxybut-2-en-1-amine hydrochloride was synthesized from (E)-tert-butyl 3-fluoro-4-bromobut-2-enylcarbamate and methanol (co-solvent).

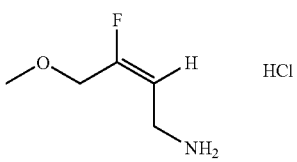

The product was obtained as white flakes; m.p.=89-91° C.; $^1$H-NMR (400 MHz, (CD$_3$)$_2$SO): δppm: 3.24 (3H, s), 3.49 (2H, d, J 8.0 Hz), 4.07 (2H, d, J 21.6 Hz), 5.40 (1H, dt, J 19.6, 8.0 Hz).

EXAMPLE 8

(Z)-4-(4-Amino-2-fluorobut-2-enyloxy)-N-cyclohexylbenzamide hydrochloride was synthesized from (Z)-tert-butyl 3-fluoro-4-hydroxybut-2-enylcarbamate and 4-hydroxy-N-cyclohexylbenzamide following procedures D, E, F and H.

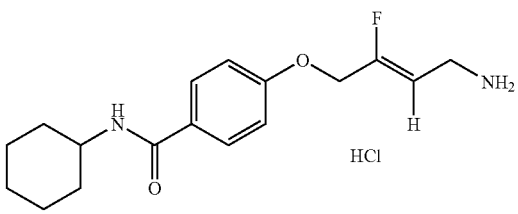 [SMILES: NC/C=C(\F)COc1ccc(C(=O)NC2CCCCC2)cc1 ; Cl]

The product was obtained as a white powder; m.p.=250-252° C.; $^1$H-NMR (400 MHz, (CD$_3$)$_2$SO): δppm: 1.09 (1H, m), 1.18-1.30 (4H, m), 1.58 (1H, m), 1.67-1.77 (4H, m), 3.50 (2H, d, J 6.0 Hz), 3.69 (1H, m), 4.75 (2H, d, J 16.0 Hz), 5.35 (1H, dt, J 35.6, 7.2 Hz), 7.00 (2H, d, J 6.8 Hz), 7.79 (2H, d, J 6.8 Hz), 7.99-8.15 (3H, br s, NHs).

EXAMPLE 9

The following compounds were prepared according to procedures F and H described above.

(E)-3-Fluoro-4-(4-(trifluoromethoxy)phenoxy)but-2-en-1-amine hydrochloride was synthesized from (E)-tert-butyl 3-fluoro-4-bromobut-2-enylcarbamate and 4-(trifluoromethoxy)phenol.

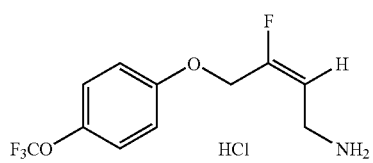 [SMILES: NC/C=C(/F)COc1ccc(OC(F)(F)F)cc1 ; Cl]

The product was obtained as an off white solid; m.p.=225-227° C.; $^1$H-NMR (400 MHz. (CD$_3$)$_2$SO): δppm: 3.60 (2H, d, J 8.0 Hz), 4.85 (2H, d, J 20.0 Hz), 5.53 (1H, dt, J 19.1, 8.1 Hz), 7.08 (2H, d, J 9.2 Hz), 7.32 (2H, d, J 9.2 Hz), 8.06-8.16 (3H, br s, NHs).

S-(E)-4-(4-Amino-2-fluorobut-2-enyloxy)-3-chloro-N-(1-phenylethyl)benzamide hydrochloride was synthesized from (E)-tert-butyl 3-fluoro-4-bromobut-2-enylcarbamate and S-3-chloro-4-hydroxy-N-(1-phenylethyl)benzamide.

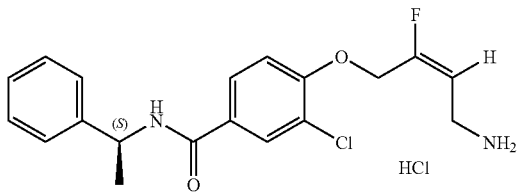

The product was obtained as a light pink solid; m.p.=116-118° C.; $^1$H-NMR (400 MHz, (CD$_3$)$_2$SO): δppm: 1.47 (3H, d, J 7.1 Hz), 3.65 (2H, m), 5.01 (2H, d, J 19.2 Hz), 5.14 (1H, quintet, J 7.4 Hz), 5.58 (1H, dt, J 19.1, 8.2 Hz), 7.22 (1H, t, J 7.2 Hz), 7.28-7.39 (5H, m), 7.91 (1H, dd, J 8.7, 2.1 Hz), 8.04 (1H, d, J 2.1 Hz), 8.07-8.15 (3H, br s, NHs), 8.81 (1H, d, J 7.9 Hz).

(E)-4-(4-Amino-2-fluorobut-2-enyloxy)-N-(adamantyl) benzamide hydrochloride was synthesized from (E)-tert-butyl 3-fluoro-4-bromobut-2-enylcarbamate and 4-hydroxy-N-(adamantyl)benzamide.

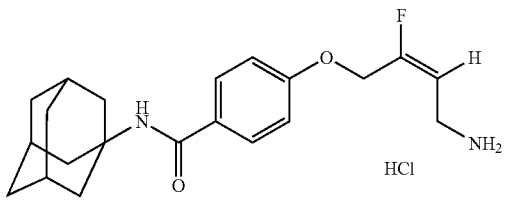 [SMILES: NC/C=C(/F)COc1ccc(C(=O)NC23CC4CC(CC(C4)C2)C3)cc1 ; Cl]

The product was obtained as white flakes; m.p.=226-228° C.; $^1$H-NMR (400 MHz, (CD$_3$)$_2$SO): δppm: 1.63 (6H, s), 2.04 (9H, s), 3.60 (2H, d, J 8.1 Hz), 4.86 (2H, d, J 19.9 Hz), 5.52 (1H, dt, J 19.1, 8.1 Hz), 6.98 (2H, d, J 9.8 Hz), 7.43 (1H, s, NH), 7.77 (2H, d, J 9.8 Hz), 8.06 (2H, br s, NHs).

(E)-4-(4-Amino-2-fluorobut-2-enyloxy)-N-(4-(trifluoromethyl)phenyl)benzamide hydrochloride was synthesized from (E)-tert-butyl 3-fluoro-4-bromobut-2-enylcarbamate and 4-hydroxy-N-(4-(trifluoromethyl)phenyl)benzamide.

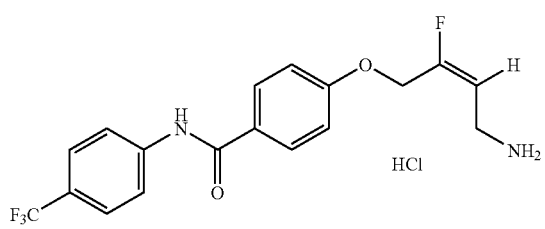 [SMILES: NC/C=C(/F)COc1ccc(C(=O)Nc2ccc(C(F)(F)F)cc2)cc1 ; Cl]

The product was obtained as a white powder; m.p.=227-229° C.; $^1$H-NMR (400 MHz, (CD$_3$)$_2$SO): δppm: 3.61 (2H, d, J 8.0 Hz), 4.94 (2H, d, J 19.9 Hz), 5.56 (1H, dt, J 19.1, 8.1 Hz), 7.14 (2H, d, J 8.8 Hz), 7.70 (2H, d, J 8.8 Hz), 7.98 (4H, m), 10.48 (1H, s, NH).

(E)-4-(4-Amino-2-fluorobut-2-enyloxy)-3,5-dichloro-N-cyclohexylbenzamide hydrochloride was synthesized from (E)-tert-butyl 3-fluoro-4-bromobut-2-enylcarbamate and 4-hydroxy-3,5-dichloro-N-cyclohexylbenzamide.

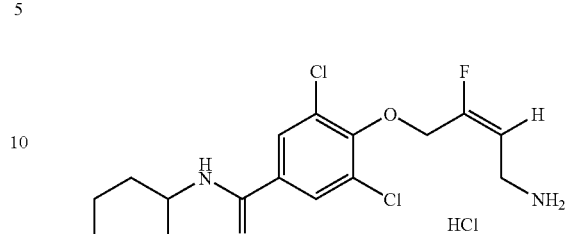

The product was obtained as an off white solid; m.p.=205-206° C.; $^1$H-NMR (400 MHz, (CD$_3$)$_2$SO): δppm: 1.09 (1H, m), 1.18-1.30 (4H, m), 1.56 (1H, m), 1.65-1.79 (4H, m), 3.48 (2H, d, J 7.6 Hz), 3.67 (1H, m), 4.80 (2H, d, J 22.8 Hz), 5.53 (1H, dt, J 18.0, 7.8 Hz), 7.95 (2H, s), 7.88-8.10 (3H, br s, NHs), 8.38 (1H, d, J 8.0 Hz, NH).

(E)-4-(4-Amino-2-fluorobut-2-enyloxy)-3-chloro-N-cyclohexyl-benzamide hydrochloride was synthesized from (E)-tert-butyl 3-fluoro-4-bromobut-2-enylcarbamate and 4-hydroxy-3-chloro-N-cyclohexylbenzamide.

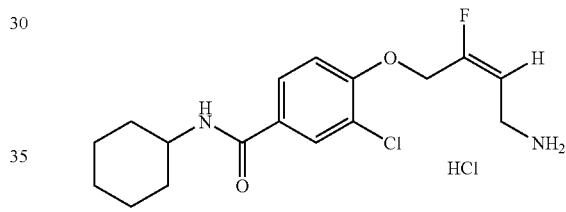

The product was obtained as a white solid; $^1$H-NMR (400 MHz, (CD$_3$)$_2$SO): δppm: 1.10 (1H, m), 1.19-1.35 (4H, m), 1.58 (1H, m), 1.70-1.79 (4H, m), 3.62 (2H, d, J 7.6 Hz), 3.71 (1H, m), 4.98 (2H, d, J 19.2 Hz), 5.56 (1H, dt, J 19.2, 8.0 Hz), 7.25 (1H, d, J 8.8 Hz), 7.84 (1H, d, J 8.8 Hz), 7.96 (1H, s), 8.20 (1H, d, J 7.6 Hz, NH).

(E)-4-(4-Amino-2-fluorobut-2-enyloxy)-N-cyclohexyl-3-fluorobenzamide hydrochloride was synthesized from (E)-tert-butyl 3-fluoro-4-bromobut-2-enylcarbamate and 4-hydroxy-N-cyclohexyl-3-fluorobenzamide.

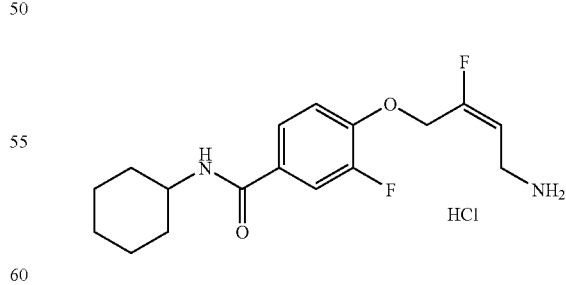

The product was obtained as a white solid; m.p.=203-206° C.; $^1$H-NMR (400 MHz, (CD$_3$)$_2$SO): δppm: 1.10 (1H, m), 1.12-1.34 (4H, m), 1.58 (1H, m), 1.71-1.80 (4H, m), 3.61 (2H, d, J 8.0 Hz), 3.72 (1H, m), 4.98 (2H, d, J 20.0 Hz), 5.57 (1H, dt, J 18.8, 8.4 Hz), 7.28 (1H, t, J 9.2 Hz), 7.74 (2H, m), 8.17 (4H, br s, NHs).

EXAMPLE 10

Preparation of tert-butyl [(2E)-3-fluoro-4-hydroxy-2-methylbut-2-en-1-yl]carbamate

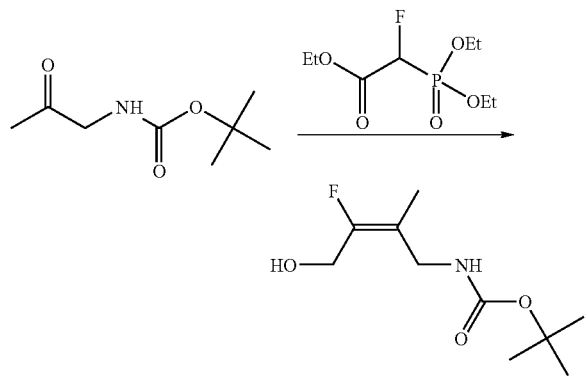

A mixture of triethyl 2-fluoro-2-phosphonoacetate (1.07 mL, 5.2 mmol), tert-butyl (2-oxopropyl)carbamate (0.865 g, 5.0 mmol) and lithium hydroxide (0.21 g, 5.0 mmol) in THF (15 mL) was at room temperature for 16 hours. The mixture was cooled to 0° C. and lithium borohydride (0.22 g, 10.0 mmol) was added in portions. Stirring was continued at 0° C. for 1 hour and at room temperature for 2 hours. Saturated ammonium chloride solution (25 mL) was added to the mixture and the organic layer extracted with ethyl acetate (50 mL) and washed with brine (20 mL), dried over MgSO$_4$, filtered and the solvent removed under reduced pressure to afford the crude product as a clear oil (0.90 g). Purification by flash chromatography eluting in 20% EtOAc in n-hexane afforded tert-butyl [(2E)-3-fluoro-4-hydroxy-2-methylbut-2-en-1-yl]carbamate (0.33 g, 30%) as white solid. $^1$H-NMR (400 MHz, CDCl$_3$): δppm: 1.42 (9H, s), 1.68 (3H, d, J 3.2 Hz), 3.67 (2H, dd, J 6.4, 1.2 Hz), 3.80 (1H, t, J 6.4 Hz), 4.26 (2H, dd, J 24.8, 6.4 Hz), 4.98 (1H, brs).

Preparation of tert-butyl [(2E)-4-bromo-3-fluoro-2-methylbut-2-en-1-yl]carbamate

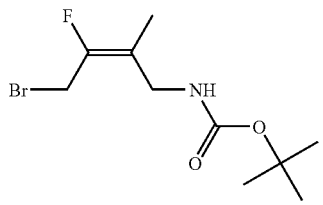

This compound was synthesized from tert-butyl [(2E)-3-fluoro-4-hydroxy-2-methylbut-2-en-1-yl]carbamate following procedures D and E; White solid, $^1$H-NMR (400 MHz, CDCl$_3$): δppm: 1.44 (9H, s), 1.72 (3H, d, J 4.0 Hz), 3.74 (2H, d, J 4.0 Hz), 4.18 (2H, dd, J 24.0, Hz), 4.66 (1H, brs).

Preparation of (E)-tert-butyl 4-(4-(cyclohexylcarbamoyl)phenoxy)-3-fluoro-2-methylbut-2-enylcarbamate

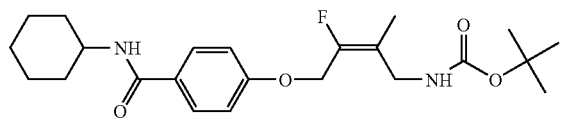

This compound was synthesized from tert-butyl [(2E)-4-bromo-3-fluoro-2-methylbut-2-en-1-yl]carbamate and N-cyclohexyl-4-hydroxybenzamide following procedure F and was obtained as a colorless solid; $^1$H-NMR (400 MHz, CDCl$_3$): δppm: 1.15-1.27 (3H, m), 1.37-1.48 (2H, m), 1.43 (9H, s), 1.62-1.67 (1H, m), 1.72-1.77 (2H, m), 1.76 (3H, d, J 4.0 Hz), 2.00-2.04 (2H, m), 3.77 (2H, d, J 5.7 Hz), 3.95 (1H, m), 4.61 (1H, br s), 4.75 (2H, d, J 21.4 Hz), 5.85 (1H, br s), 6.95 (2H, d, J 9.0 Hz), 7.72 (2H, d, J 9.0 Hz).

Preparation of (Z)-tert-butyl 4-(4-(cyclohexylcarbamoyl)phenoxy)-3-fluoro-2-methylbut-2-enylcarbamate

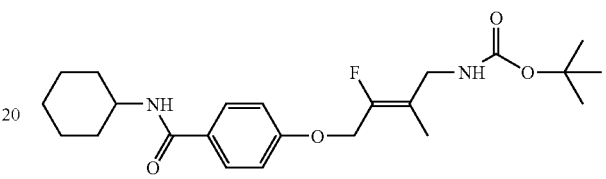

This compound was synthesized from tert-butyl [(2Z)-4-bromo-3-fluoro-2-methylbut-2-en-1-yl]carbamate and N-cyclohexyl-4-hydroxybenzamide following procedure F and was obtained as a colorless solid; $^1$H-NMR (400 MHz, CDCl$_3$): δppm: 1.14-1.30 (3H, m), 1.35-1.49 (2H, m), 1.44 (9H, s), 1.60-1.70 (1H, m), 1.70-1.79 (2H, m), 1.76 (3H, d, J 3.2 Hz), 1.98-2.04 (2H, m), 3.90 (2H, d, J 5.3 Hz), 3.96 (1H, m), 4.59 (1H, br s), 4.63 (2H, d, J 21.2 Hz), 5.86 (1H, d, J 7.9 Hz), 6.93 (2H, d, J 8.7 Hz), 7.71 (2H, d, J 8.7 Hz).

(E)-4-(4-Amino-2-fluoro-3-methylbut-2-enyloxy)-N-cyclohexylbenzamide hydrochloride

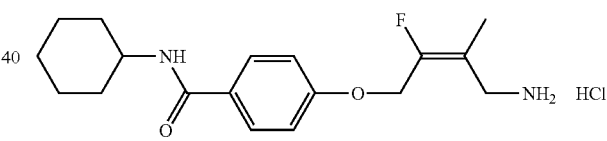

This compound was synthesized from (E)-tert-butyl 4-(4-(cyclohexyl-carbamoyl)phenoxy)-3-fluoro-2-methylbut-2-enylcarbamate following procedure H and was obtained as an off-white powder; m.p.=216-218° C.; $^1$H-NMR (400 MHz, (CD$_3$)$_2$SO): δppm: 1.10 (1H, m), 1.21-1.35 (4H, m), 1.58 (1H, m), 1.69-1.79 (4H, m), 1.78 (3H, d, J 4.3 Hz), 3.58 (2H, s), 3.71 (1H, m), 4.85 (2H, d, J 22.0 Hz), 7.00 (2H, d, J 9.0 Hz), 7.82 (2H, d, J 9.0 Hz), 8.05 (1H, d, J=8.1 Hz), 8.21 (3H, br s).

(Z)-4-(4-Amino-2-fluoro-3-methylbut-2-enyloxy)-N-cyclohexylbenzamide hydrochloride

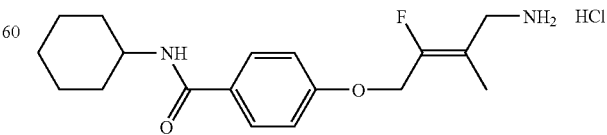

This compound was synthesized from (Z)-tert-butyl 4-(4-(cyclohexyl-carbamoyl)phenoxy)-3-fluoro-2-methylbut-2- enylcarbamate following procedure H and was obtained as an off-white powder; m.p.=236-238° C.; $^1$H-NMR (400 MHz, (CD$_3$)$_2$SO): δppm: 1.10 (1H, m), 1.20-1.31 (4H, m), 1.59 (1H, m), 1.66-1.80 (4H, m), 1.82 (3H, d, J 3.0 Hz), 3.52 (2H, d, J 2.2 Hz), 3.71 (1H, m), 4.83 (2H, d, J 22.0 Hz), 7.01 (2H, d, J 8.8 Hz), 7.81 (2H, d, J 8.8 Hz), 8.04 (1H, d, J=8.1 Hz), 8.14 (3H, br s).

EXAMPLE 11

Method to Determine the Ability of Invention Compounds to Inhibit the Amine Oxidase Activity of SSAO/VAP-1

3T3-L1 Murine fibroblasts were purchased from the American Type Culture Collection (ATCC, Rockville, Md.). Dulbecco's Modified Eagle Medium (DMEM) and fetal calf serum (FCS), antibiotics and Amplex® Red were obtained from Invitrogen (Carlsbad, Calif.). Tissue culture plastics and black clear-bottom 96 well plates were from BD Falcon (Bedford, Mass.). Bicinchoninic acid (BCA) reagent was from Pierce (Rockford, Ill.). All other materials were obtained from Sigma (St. Louis, Mo.).

3T3-L1 Fibroblasts were cultured in DMEM supplemented with 10% heat-inactivated FCS, 2 mM L-glutamine, 100 U/L penicillin and 100 µg/L streptomycin at 37° C. in 5% CO2. For differentiation into adipocytes, fibroblasts were cultured in DMEM with FCS for 1 or 2 days postconfluence, after which the cells were cultured for 3 days in DMEM containing 10% FCS, 350 nM insulin, 0.5 mM 3-isobutyl-1-methylxanthine, 250 nM dexamethasone, and 400 nM biotin and for 3 days in DMEM containing 10% FCS and 350 nM insulin. After differentiation, adipocytes were maintained in DMEM supplemented with 10% FCS. Adipocytes were used for experiments 8 to 11 days after the onset of differentiation, and the medium was renewed 2 or 3 days prior to each experiment. For culturing in black clear-bottom 96-well plates, cells were seeded at a 1:1 cell surface ratio, and differentiation was initiated 4 days postseeding. Cells were used between days 6-12 post-differentiation and between passages 7 and 20. Adipocytes were used as an SSAO source either as adherent cells or as a homogenate.

To prepare homogenate, 10 cm dishes of adipocytes were washed with HES buffer (20 mM HEPES, 1 mM EDTA, 250 mM sucrose, pH 7.4) and scraped in HES buffer containing 10 µg/mL leupeptin, 10 µM pepstatin and 1 mM PMSF. Cells were lysed by passage through a 23 G needle followed by passage through a 27 G needle. The lysate was spun at 500 g for 5 min and fat was removed. Protein concentration of the supernatant was measured using a BCA assay according to the manufacturer's instructions. The homogenate was stored at −80° C. until needed.

To measure the SSAO activity, adipocyte homogenate (0.5 mg/mL) or adipocytes (adhering cells) containing 0.5 mM pargyline, or purified human SSAO was incubated in 0.1 M sodium phosphate buffer pH 7.4 with varying concentrations of test compounds for 30 min at 37° C. The homogenate was then incubated at 37° C. with 60 µM Amplex® Red, 0.75 U/mL HRP and 40 µM benzylamine (mouse SSAO) or 300 µM benzylamine (human SSAO) and the formation of resorufin was measured (excitation range 530-560 nm and emission at 590 nm) every 10 min in either a Tecan Infinite 200 or a BMG plate reader. The IC$_{50}$ values were estimated using Graphpad Prism software. The IC$_{50}$ is an estimation of the concentration of the test compound to inhibit the amine oxidase activity of SSAO/VAP-1 by 50%. The IC$_{50}$ values of certain invention compounds are included in Table 1.

EXAMPLE 12

Method to Determine the Ability of Invention Compounds to Inhibit the Amine Oxidase Activity of SSAO/VAP-1 in an Animal In vivo inhibition was assessed in mouse genital fat, a tissue with high SSAO/VAP-1 expression. 10 BALB/C mice (5 males and 5 females) were administered 0 mg/kg, 10 mg/kg, 30 mg/kg or 100 mg/kg SSAO/VAP-1 inhibitor by intraperitoneal injection. Two hours after administration the mice were sacrificed and the genital fat was excised and frozen. The tissue was homogenized in 0.01 M sodium phosphate buffer pH 7.4 (10 mL/g) and used to measure SSAO activity using Amplex® Red. ED$_{50}$ was estimated Using Graphpad Prism software.

Results with exemplary compounds according to the invention are presented in Table 2.

TABLE 2

In vivo SSAO/VAP-1 inhibitory properties of exemplary inventive compounds and a comparative compound

| Compound Name (Using the Cambridge Soft proprietary naming algorithm) | Male Mice ED$_{50}$ (mg/kg) [ip] | Female Mice ED$_{50}$ (mg/kg) [ip] |
|---|---|---|
| (E)-3-Fluoro-4-(4-(methylsulfonyl)phenoxy)but-2-en-1-amine hydrochloride | <100 | <300 |
| (E)-4-(4-Amino-2-fluorobut-2-enyloxy)-N-cyclopentyl-benzamide hydrochloride | <50 | <50 |
| (E)-3-Fluoro-4-(4-(isopropylsulfonyl)phenoxy)but-2-en-1-amine hydrochloride | <150 | <150 |
| (E)-4-(4-(Benzylsulfonyl)phenoxy)-3-fluorobut-2-en-1-amine hydrochloride | <50 | <300 |
| S-(E)-4-(4-Amino-2-fluorobut-2-enyloxy)-N-(1-phenylethyl)benzamide hydrochloride | <50 | <50 |
| R-(E)-4-(4-Amino-2-fluorobut-2-enyloxy)-N-(1-phenylethyl)benzamide hydrochloride | <50 | <150 |
| (E)-4-(4-amino-2-fluorobut-2-enyloxy)-N-cyclohexyl-benzamide hydrochloride | <50 | <50 |
| (E)-3-Fluoro-4-(2-methylbenzo[d]thiazol-5-yloxy)but-2-en-1-amine hydrochloride | <50 | <100 |
| S-(E)-4-(4-Amino-2-fluorobut-2-enyloxy)-N-(1-phenylethyl)benzenesulfonamide hydrochloride | <50 | <50 |
| Mofegiline | <1 | <1 |

EXAMPLE 13

Methods to Determine the Ability of Invention Compounds to Inhibit an Inflammatory Response in an Animal Model Inhibition of Oxazolone-Induced Ear Edema in Mice by SSAO/VAP-1 Inhibitors The murine oxazolone-induced ear edema model is widely used as delayed type hypersensitivity (DTH) model, typically exemplified by allergic contact dermatitis such as eczema. 4 groups of 8 BALB/c mice were sensitized with a topical application of 100 mL of 5% oxazolone in acetone on the shaved ventral abdomen on day-7. SSAO/VAP-1 inhibitors were administered by intraperitoneal injection (0 mg/kg, 10 mg/kg, 30 mg/kg and 100 mg/kg) 3 hrs prior to oxazolone challenge. Five microliters of 3% oxazolone solution was applied to the dorsal and ventral surface of the left ear and 5 mL of acetone was applied to the dorsal and ventral surface of the right ear. 24 hours after the oxazolone challenge the mice were euthanized and the ears were removed. The weights of the ears were recorded on an analytical balance. The percent inhibition of oxazolone-induced edema for each of the groups was determined as follow: % Inhibition=$1-(W_{(irr+compound)}-W_{(vehicle)} \times 100)/W_{(irr)}-W_{(vehicle)})$ where: W=weight of ear and Irr=irritant (inflammatory agent, e.g. oxazolone).

Inhibition of Pulmonary LPS Induced Lymphopenia in Mice

Pulmonary neutrophil activation by LPS is used as an in vivo model for allergic asthma, bronchitis and/or chronic obstructive pulmonary disease (COPD). LPS initiates neutrophil activation and release of proinflammatory cytokines including TNF-α and IL-6, followed by neutrophil infiltration into the bronchoalveolae mediated by chemokines such as IL-8 and CXCL5. Subsequent localized pulmonary injury and inflammation is then further exacerbated by activation of p38 kinase/cJun kinase pathways, metalloproteinases, leukotrienes and iNOS resulting in pulmonary congestion. Female BALB/c mice weighing 20 to 22 g were fasted overnight prior to use. The test substance and vehicle were administered intraperitoneally (100 mg/kg) to groups of 5 animals at least 3 hours before challenge with ~80 μg/kg of $E.$ $Coli$ lipopolysaccharide (LPS in sterile saline, 2 μg in 20 μL per mouse intratracheally). Mice were anaesthetized by propofol (10 mg/mL, 50 μL/mouse, i.v.) 24 hours after LPS challenge, 0.25 mL of phosphate buffered saline (PBS) was administered twice through a tracheal cannula after which about 0.3 ml of bronchoalveolar lavage fluid (BALF) was obtained. Total cell number/mL and % neutrophils in BALF are then determined and one-way ANOVA followed by Dunnett's test is used to determine possible significant difference at $P<0.05$.

EXAMPLE 14

Method to Determine the Ability of Invention Compounds to Inhibit the MAO-A and MAO-B Recombinant MAO-B was incubated in 0.1 M sodium phosphate buffer pH 7.4 with varying concentration of test compounds for 30 min at 37° C. The homogenate/protein was then incubated at 37° C. with 60 mM Amplex® Red, 0.75 U/ml HRP and 40 μM benzylamine (mouse SSAO), 300 μM benzylamine (human SSAO), 100 μM tyramine (MAO-A) or 50 μM benzylamine (MAO-B) and the formation of resorufin was measured (excitation range 530-560 nm and emission at 590 nm) every 5 min in either a Tecan Infinite 200 or a BMG Fluorostar Optima platereader. $IC_{50}$ were estimated using Graphpad Prism software. Typical results for exemplary compounds according to the invention are presented in Table 1.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to provide additional compounds of Formula I and/or various methods of administration can be used. Thus, such additional embodiments are within the scope of the present invention and the following claims.

The invention illustratively described herein suitably may be practiced in the absence of any element or elements, limitation or limitations which is not specifically disclosed herein. The terms and expressions which have been employed are used as terms of description and not of limitation, and there is no intertion that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A compound of formula I:

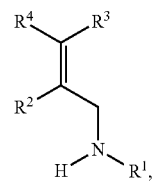

Formula 1 or stereoisomers, enantiomers, diastereoisomers, or pharmaceutically acceptable salts thereof; wherein:
$R^1$ is hydrogen or lower alkyl;
$R^2$ is hydrogen, substituted or unsubstituted lower alkyl;
$R^3$ and $R^4$ are independently fluorine or —$CH_2$—O—$R^5$—$R^6$;

provided, however, that one of $R^3$ and $R^4$ is fluorine, but both $R^3$ and $R^4$ are not fluorine at the same time;

$R^5$ is substituted or unsubstituted aryl; and $R^6$ is hydrogen or $R^6$ is selected from the group consisting of:

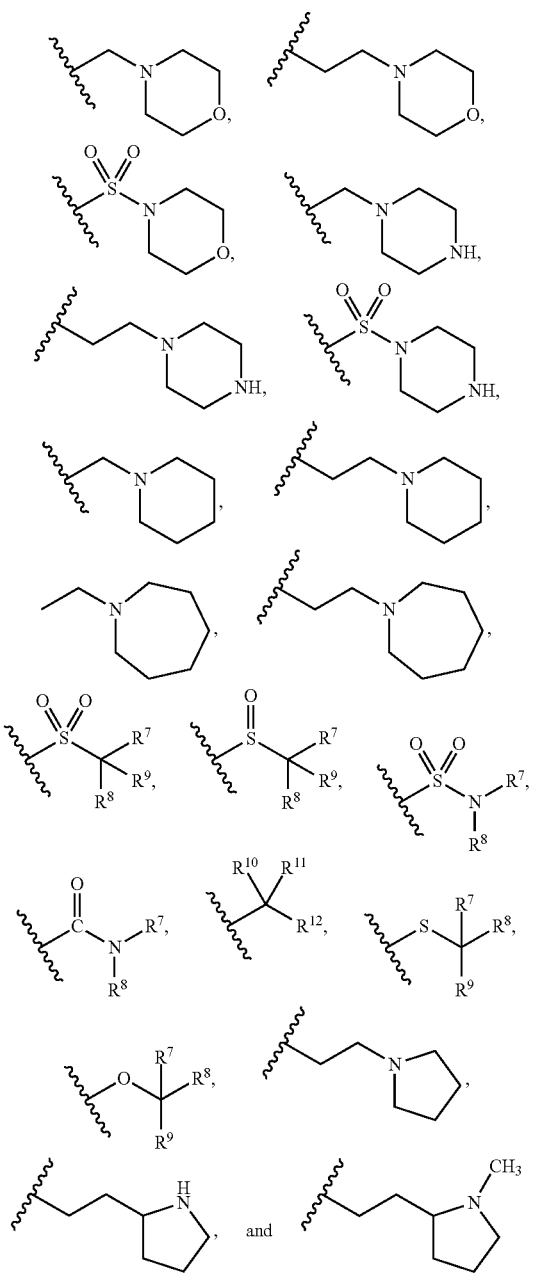

wherein:

each of $R^7$ and $R^8$ are independently hydrogen, substituted or unsubstituted aryl, substituted or unsubstituted heteroaryl, substituted or unsubstituted heterocyclyl, substituted or unsubstituted alkyl, substituted or unsubstituted cycloalkyl, substituted or unsubstituted alkenyl, substituted or unsubstituted cycloalkenyl, substituted or unsubstituted alkynyl, substituted or unsubstituted alkylaryl, or substituted or unsubstituted alkylheteroaryl; or $R^7$ and $R^8$ may cooperate to form a substituted or unsubstituted cycloalkyl, cycloalkenyl, heterocycloalkyl, or heterocycloalkenyl ring system;

$R^9$ is hydrogen, amido, carboximido, lower alkylamido, cycloalkylamido, lower alkylcarboximido, or cycloalkylcarboximido;

each of $R^{10}$ and $R^{11}$ are independently hydrogen, substituted or unsubstituted alkyl, substituted or unsubstituted alkenyl, or substituted or unsubstituted alkynyl; and $R^{12}$ is selected from substituted or unsubstituted alkyl, substituted or unsubstituted alkenyl, substituted or unsubstituted alkynyl, substituted or unsubstituted alkylaryl, substituted or unsubstituted alkylheteroaryl, amido, carboximido, lower alkylamido, cycloalkylamido, lower alkylcarboximido, or cycloalkylcarboximido.

2. A compound of claim 1, wherein $R^6$ is selected from the group consisting of:

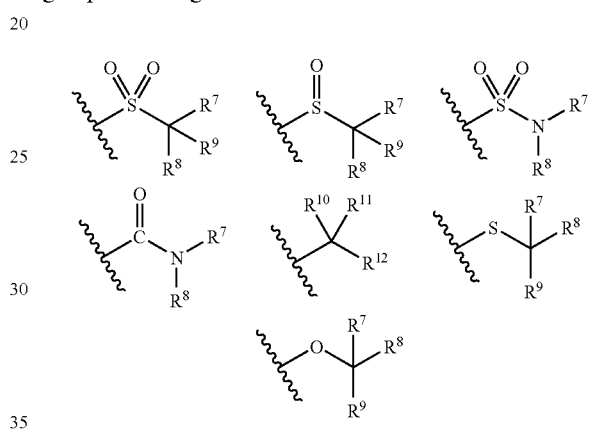

wherein:

each of $R^7$ and $R^8$ are independently hydrogen, substituted or unsubstituted aryl, substituted or unsubstituted heteroaryl, substituted or unsubstituted heterocyclyl, substituted or unsubstituted alkyl, substituted or unsubstituted cycloalkyl, substituted or unsubstituted alkenyl, substituted or unsubstituted cycloalkenyl, substituted or unsubstituted alkynyl, substituted or unsubstituted alkylaryl, or substituted or unsubstituted alkylheteroaryl; or $R^7$ and $R^8$ may cooperate to form a substituted or unsubstituted cycloalkyl, cycloalkenyl, heterocycloalkyl, or heterocycloalkenyl ring system;

$R^9$ is hydrogen, amido, carboximido, lower alkylamido, cycloalkylamido, lower alkylcarboximido, or cycloalkylcarboximido;

each of $R^{10}$ and $R^{11}$ are independently hydrogen, substituted or unsubstituted alkyl, substituted or unsubstituted alkenyl, or unsubstituted alkynyl; and $R^{12}$ is selected from substituted or unsubstituted alkyl, substituted or unsubstituted alkenyl, substituted or unsubstituted alkynyl, substituted or unsubstituted alkylaryl, or substituted or unsubstituted alkylheteroaryl, amido, carboximido, lower alkylamido, cycloalkylamido, lower alkylcarboximido, or cycloalkylcarboximido.

3. A compound of claim 1 wherein said compound is selected from the group consisting of:

(E)-3-Fluoro-4-phenoxybut-2-en-1-amine, (E)-3-Fluoro-4-(4-(trifluoromethyl)phenoxy)but-2-en-1-amine, (E)-4-(2,4-Dichlorophenoxy)-3-fluorobut-2-en-1-amine, (E)-3-Fluoro-4-(4-methoxyphenoxy)but-2-en-1-amine,
(E)-4-(3,4-Difluorophenoxy)-3-fluorobut-2-en-1-amine,
(E)-3-Fluoro-4-(4-nitrophenoxy)but-2-en-1-amine,
(E)-4-(4-tert-Butylphenoxy)-3-fluorobut-2-en-1-amine,
(Z)-3-Fluoro-4-(4-(trifluoromethyl)phenoxy)but-2-en-1-amine,
(E)-3-Fluoro-4-(3-(trifluoromethyl)phenoxy)but-2-en-1-amine,
(E)-3-Fluoro-4-(4-fluorophenoxy)but-2-en-1-amine,
(E)-3-Fluoro-4-(4-(methylsulfonyl)phenoxy)but-2-en-1-amine,
(E)-3-Fluoro-4-(4-(morpholinosulfonyl)phenoxy)but-2-en-1-amine,
(Z)-3-Fluoro-4-phenoxybut-2-en-1-amine,
(Z)-4-(2,4-Dichlorophenoxy)-3-fluorobut-2-en-1-amine,
(E)-4-(3-Chloro-4-fluorophenoxy)-3-fluorobut-2-en-1-amine,
(E)-3-Fluoro-4-(4-phenoxyphenoxy)but-2-en-1-amine,
(E)-3-Fluoro-4-(naphthalen-2-yloxy)but-2-en-1-amine,
(E)-(4-(4-Amino-2-fluorobut-2-enyloxy)phenyl)(phenyl)methanone,
(E)-4-(2-Chloro-4-nitrophenoxy)-3-fluorobut-2-en-1-amine,
(E)-4-(6-Chlorobenzo[d][1,3]dioxol-5-yloxy)-3-fluorobut-2-en-1-amine,
(E)-4-(4-Amino-2-fluorobut-2-enyloxy)-N-(3-fluoro-5-(trifluoromethyl)benzyl)benzamide,
(E)-3-Fluoro-4-(4-(morpholinosulfonyl)phenoxy)but-2-en-1-amine,
(E)-4-(4-(4,4-Dimethyl-4,5-dihydrooxazol-2-yl)phenoxy)-3-fluorobut-2-en-1-amine,
(E)-3-Fluoro-4-(4-(methylsulfonyl)phenoxy)but-2-en-1-amine,
(E)-3-Fluoro-4-(4-(methylthio)phenoxy)but-2-en-1-amine,
(E)-4-(4-tert-Butyl-2-chlorophenoxy)-3-fluorobut-2-en-1-amine,
(E)-3-Fluoro-4-(2-chloro-4-(methylsulfonyl)phenoxy)but-2-en-1-amine,
(E)-4-(4-Amino-2-fluorobut-2-enyloxy)-N-cyclopentylbenzamide,
(E)-4-(4-Amino-2-fluorobut-2-enyloxy)-N,N-dimethylbenzenesulfonamide,
(E)-4-(4-Amino-2-fluorobut-2-enyloxy)-N-benzyl-N-methylbenzamide,
(E)-3-Fluoro-4-(4-(trifluoromethylsulfonyl)phenoxy)but-2-en-1-amine,
(E)-4-(4-Amino-2-fluorobut-2-enyloxy)-N,N-dimethylbenzamide,
(E)-4-(4-Amino-2-fluorobut-2-enyloxy)-N,N-diethylbenzenesulfonamide,
(E)-3-Fluoro-4-(4-(methylsulfinyl)phenoxy)but-2-en-1-amine,
(E)-3-Fluoro-4-(3-methyl-4-(methylsulfonyl)phenoxy)but-2-en-1-amine,
(E)-(4-(4-Amino-2-fluorobut-2-enyloxy)phenyl)(pyrrolidin-1-yl)methanone,
(E)-4-(2-Chlorophenoxy)-3-fluorobut-2-en-1-amine,
(E)-4-(3,5-Dichlorophenoxy)-3-fluorobut-2-en-1-amine,
(E)-4-(4-Bromophenoxy)-3-fluorobut-2-en-1-amine,
(E)-3-Fluoro-4-(4-iodophenoxy)but-2-en-1-amine,
(E)-3-Fluoro-4-(4-(isopropylsulfonyl)phenoxy)but-2-en-1-amine,
(E)-3-Fluoro-4-(4-(pyrrolidin-1-ylsulfonyl)phenoxy)but-2-en-1-amine,
(E)-4-(4-(Ethylsulfonyl)phenoxy)-3-fluorobut-2-en-1-amine,
R/S-(E)-4-(4-Amino-2-fluorobut-2-enyloxy)-N-(1-phenylethyl)benzamide,
(E)-4-(4-(Benzylsulfonyl)phenoxy)-3-fluorobut-2-en-1-amine,
(E)-4-(Biphenyl-4-yloxy)-3-fluorobut-2-en-1-amine,
(E)-4-(4-amino-2-fluorobut-2-enyloxy)-N-cyclohexylbenzamide,
S-(E)-4-(4-Amino-2-fluorobut-2-enyloxy)-N-(1-phenylethyl)benzamide,
R-(E)-4-(4-Amino-2-fluorobut-2-enyloxy)-N-(1-phenylethyl)benzamide,
(E)-3-Fluoro-4-(phenylthio)but-2-en-1-amine,
(E)-4-(4-Amino-2-fluorobut-2-enyloxy)-N-tert-butylbenzamide,
(E)-4-(4-(Cyclopentylsulfonyl)phenoxy)-3-fluorobut-2-en-1-amine,
(E)-3-Fluoro-4-(4-(isobutylsulfonyl)phenoxy)but-2-en-1-amine,
(E)-3-Fluoro-4-(4-(neopentylsulfonyl)phenoxy)but-2-en-1-amine,
(E)-3-Fluoro-4-(4-(phenethylsulfonyl)phenoxy)but-2-en-1-amine,
(E)-4-(4-(sec-Butylsulfonyl)phenoxy)-3-fluorobut-2-en-1-amine,
(E)-3-Fluoro-4-(4-(1-phenylethylsulfonyl)phenoxy)but-2-en-1-amine,
(E)-3-Fluoro-4-(4-(4-fluorobenzylsulfonyl)phenoxy)but-2-en-1-amine,
(E)-4-(9H-Carbazol-2-yloxy)-3-fluorobut-2-en-1-amine,
(E)-4-(4-(1H-Imidazol-1-yl)phenoxy)-3-fluorobut-2-en-1-amine,
(E)-4-(4-Amino-2-fluorobut-2-enyloxy)-N-isopropylbenzamide,
(E)-4-(4-Amino-2-fluorobut-2-enyloxy)-N-phenylbenzamide,
(E)-3-Fluoro-4-(2-methylbenzo[d]thiazol-5-yloxy)but-2-en-1-amine,
(E)-4-(Benzo[d]thiazol-2-yloxy)-3-fluorobut-2-en-1-amine,
(E)-N-(4-(4-Amino-2-fluorobut-2-enyloxy)phenyl)acetamide,
(E)-7-(4-Amino-2-fluorobut-2-enyloxy)-3-(4-hydroxyphenyl)-4H-chromen-4-one,
(E)-3-Fluoro-4-(pyridin-3-yloxy)but-2-en-1-amine,
(E)-3-Fluoro-4-(2-p-tolylbenzo[d]thiazol-6-yloxy)but-2-en-1-amine,
(E)-2-(4-(4-Amino-2-fluorobut-2-enyloxy)phenylsulfonyl)ethanol,
(E)-3-Fluoro-4-(4-(2-morpholinoethylsulfonyl)phenoxy)but-2-en-1-amine,
(E)-3-Fluoro-4-(4-(2-(pyrrolidin-1-yl)ethylsulfonyl)phenoxy)but-2-en-1-amine,
(E)-3-Fluoro-4-(4-(2-(piperidin-1-yl)ethylsulfonyl)phenoxy)but-2-en-1-amine,
(E)-3-Fluoro-4-(2-methylpyridin-3-yloxy)but-2-en-1-amine,
(E)-3-Fluoro-4-(6-methylpyridin-3-yloxy)but-2-en-1-amine,
(E)-3-Fluoro-4-(2-methylbenzo[d]thiazol-6-yloxy)but-2-en-1-amine,
(E)-4-(4-Amino-2-fluorobut-2-enyloxy)-N-isopropylbenzenesulfonamide,
(E)-4-(4-Amino-2-fluorobut-2-enyloxy)-N-cyclohexylbenzenesulfonamide,
(E)-4-(4-Amino-2-fluorobut-2-enyloxy)-N-(1-phenylethyl)benzenesulfonamide, (E)-3-Fluoro-4-(4-(4-(4-methoxyphenyl)thiazol-2-yl)phenoxy)but-2-en-1-amine,
S-(E)-4-(4-Amino-2-fluorobut-2-enyloxy)-N-(1-phenylethyl)benzenesulfonamide,
(E)-4-(2-tert-Butylbenzo[d]thiazol-5-yloxy)-3-fluorobut-2-en-1-amine,
(E)-3-Fluoro-4-(2-p-tolylbenzo[d]thiazol-5-yloxy)but-2-en-1-amine,
(E)-4-(2-Cyclohexylbenzo[d]thiazol-5-yloxy)-3-fluorobut-2-en-1-amine,
(Z)-4-(4-Amino-2-fluorobut-2-enyloxy)-N-cyclohexylbenzamide,
(E)-3-Fluoro-4-(4-(trifluoromethoxy)phenoxy)but-2-en-1-amine,
S-(E)-4-(4-Amino-2-fluorobut-2-enyloxy)-3-chloro-N-(1-phenylethyl)benzamide,
(E)-4-(4-Amino-2-fluorobut-2-enyloxy)-N-(adamantyl)benzamide,
(E)-4-(4-Amino-2-fluorobut-2-enyloxy)-N-(4-(trifluoromethyl)phenyl)benzamide,
(E)-4-(4-Amino-2-fluorobut-2-enyloxy)-3,5-dichloro-N-cyclohexylbenzamide,
(E)-4-(4-Amino-2-fluorobut-2-enyloxy)-3-chloro-N-cyclohexylbenzamide,
(E)-4-(4-Amino-2-fluorobut-2-enyloxy)-N-cyclohexyl-3-fluorobenzamide,
(E)-4-(4-Amino-2-fluoro-3-methylbut-2-enyloxy)-N-cyclohexylbenzamide, and
(Z)-4-(4-Amino-2-fluoro-3-methylbut-2-enyloxy)-N-cyclohexylbenzamide.

4. A composition comprising a compound according to claim 1 and at least one pharmaceutically acceptable excipient, carrier or diluent therefor.

5. A method of inhibiting a semicarbazide-sensitive amine oxidase enzyme in a subject in need thereof, said method comprising administering to said subject an amount of a compound of claim 1 effective to elicit a positive therapeutic response.

6. A method of treating a disease or condition associated with a semicarbazide-sensitive amine oxidase enzyme comprising administering to a subject in need thereof a therapeutically effective amount of a compound of claim 1 wherein the disease or condition is inflammation associated with respiratory disease.

7. The method of claim 5 wherein the subject has inflammation associated with respiratory disease.

8. The method of claim 7 wherein said respiratory disease is asthma.

9. The method of claim 7 wherein said respiratory disease is chronic obstructive pulmonary disease.

10. The method of claim 6 wherein said respiratory disease is asthma.

11. The method of claim 6 wherein said respiratory disease is chronic obstructive pulmonary disease.

* * * * *